US008624027B2

(12) United States Patent
Shah et al.

(10) Patent No.: US 8,624,027 B2
(45) Date of Patent: *Jan. 7, 2014

(54) COMBINATION THERAPY FOR TREATING CANCER AND DIAGNOSTIC ASSAYS FOR USE THEREIN

(75) Inventors: Omar Jameel Shah, Lake Villa, IL (US); Yu Shen, Gurnee, IL (US); Xiaoyu Lin, Gurnee, IL (US); Mark Anderson, Grayslake, IL (US); Xiaoli Huang, Lake Bluff, IL (US); Junling Li, Gurnee, IL (US); Leiming Li, Buffalo Grove, IL (US)

(73) Assignee: AbbVie Inc., North Chicago, IL (US)

( * ) Notice: Subject to any disclaimer, the term of this patent is extended or adjusted under 35 U.S.C. 154(b) by 635 days.

This patent is subject to a terminal disclaimer.

(21) Appl. No.: 12/630,957

(22) Filed: Dec. 4, 2009

(65) Prior Publication Data
US 2010/0227838 A1   Sep. 9, 2010

Related U.S. Application Data

(60) Continuation-in-part of application No. 12/120,914, filed on May 15, 2008, now Pat. No. 7,709,467, which is a division of application No. 11/432,937, filed on May 12, 2006, now Pat. No. 7,390,799.

(60) Provisional application No. 60/718,618, filed on Sep. 20, 2005, provisional application No. 60/680,107, filed on May 12, 2005.

(51) Int. Cl.
*C07D 295/00* (2006.01)
*A61K 31/4965* (2006.01)

(52) U.S. Cl.
USPC ........... 544/393; 544/224; 544/336; 544/358; 544/392; 514/247; 514/252.1; 514/252.12; 514/255.03

(58) Field of Classification Search
None
See application file for complete search history.

(56) References Cited

U.S. PATENT DOCUMENTS

| 2,413,833 | A | 1/1947 | Kyrides |
| 5,138,069 | A | 8/1992 | Carini et al. |
| 6,410,584 | B1 | 6/2002 | Pamukcu et al. |
| 6,703,382 | B2 * | 3/2004 | Wang et al. ............ 514/183 |
| 6,720,338 | B2 | 4/2004 | Augeri et al. |
| 7,030,115 | B2 | 4/2006 | Elmore et al. |
| 7,358,251 | B2 | 4/2008 | Elmore et al. |
| 7,390,799 | B2 | 6/2008 | Bruncko et al. |
| 7,449,485 | B2 | 11/2008 | Elmore et al. |
| 7,504,512 | B2 | 3/2009 | Augeri et al. |
| 7,585,858 | B2 | 9/2009 | Elmore et al. |
| 7,642,260 | B2 * | 1/2010 | Bruncko et al. ........ 514/252.12 |
| 7,709,467 | B2 * | 5/2010 | Bruncko et al. ........ 514/211.15 |
| 7,767,684 | B2 | 8/2010 | Bruncko et al. |
| 7,906,505 | B2 | 3/2011 | Bruncko et al. |
| 2002/0055631 | A1 | 5/2002 | Augeri et al. |
| 2003/0119894 | A1 | 6/2003 | Murthy et al. |
| 2003/0236247 | A1 | 12/2003 | Elmore et al. |
| 2005/0159427 | A1 | 7/2005 | Bruncko et al. |
| 2006/0128706 | A1 | 6/2006 | Bruncko et al. |
| 2006/0258657 | A1 | 11/2006 | Bruncko et al. |
| 2007/0072860 | A1 | 3/2007 | Bruncko et al. |
| 2008/0076779 | A1 | 3/2008 | Elmore et al. |
| 2010/0240715 | A1 | 9/2010 | Bruncko et al. |

FOREIGN PATENT DOCUMENTS

| DE | 19922052 A1 | 11/2000 |
| EA | 200602100 A1 | 4/2007 |
| EP | 1685119 A1 | 8/2006 |
| NZ | 230136 A | 12/1991 |
| RU | 2007101276 A | 8/2008 |
| RU | 2007128959 A | 2/2009 |
| TW | 200526559 | 8/2005 |
| WO | 02024636 A2 | 3/2002 |
| WO | WO02098848 A1 | 12/2002 |
| WO | 03040107 A1 | 5/2003 |
| WO | 03080586 A1 | 10/2003 |
| WO | 2004043950 A1 | 5/2004 |
| WO | 2004048329 A1 | 6/2004 |
| WO | WO2005049593 A2 | 6/2005 |
| WO | WO2005049594 A1 | 6/2005 |
| WO | WO 2005/111039 A2 | 11/2005 |
| WO | WO 2006/009869 A1 | 1/2006 |
| WO | WO 2006/070195 A1 | 7/2006 |
| WO | WO2007038406 A1 | 4/2007 |
| WO | WO2007040650 A2 | 4/2007 |
| WO | WO2008017121 A1 | 2/2008 |
| WO | WO2008017123 A1 | 2/2008 |
| WO | WO2008082643 A2 | 7/2008 |
| WO | WO2008141145 A1 | 11/2008 |

OTHER PUBLICATIONS

Amundson et al., "An Informatics Approach Identifying Markers of Chemosensitivity in Human Cancer Cell Lines," Cancer Research, 2000, 60, pp. 6101-6110.

Applicant's Amendment and Response dated Nov. 19, 2009, pp. 1-6 in response to U.S.P.T.O. Office Action for U.S. Appl. No. 11/491,851.

Applicant's Amendment and Response dated Nov. 2, 2009, pp. 1-29, in response to U.S.P.T.O. Office Action for U.S. Appl. No. 11/127,940.

Applicant's Amendment and Response dated Oct. 8, 2009, pp. 1-7, in response to U.S.P.T.O. Restriction Requirement for U.S. Appl. No. 11/600,445.

(Continued)

*Primary Examiner* — Brandon Fetterolf
*Assistant Examiner* — Theodore R West

(57) ABSTRACT

The present disclosure relates to a combination of therapeutic agents for use in treating a patient a subject suffering from cancer. In addition, the present disclosure also relates to diagnostic assays useful in classification of patients for treatment with one or more therapeutic agents.

10 Claims, 19 Drawing Sheets

(56) References Cited

OTHER PUBLICATIONS

Cheng, et al., "Synthesis of N-Heteroaryl-7-azabicyclo[2.2.1]heptane Derivatives via Palladium-Bisimidazol-2-ylidene Complex Catalyzed Amination Reactions," Organic Letters, 2001, 3—Issue 9, pp. 1371-1374.
Gambacorta et al., "Bicyclo[3.3.1]nonane Approach to Triquinanes. Formal Synthesis of (+/−)9(12)Campnellene and (+/−)(+/−)delta 9(12)Capnellene-8β-10a-diol," Tetrahedron 1992, 48 Issue 21, pp. 4459-4464.
Holzelova et al., "Autoimmune Lymphoproliferative Syndrome with Somatic Fas Mutations," New England Journal of Medicine, 2004, 351, pp. 1409-1418.
International Search Report for application No. PCT/US2006/018799, Mailed on Mar. 22, 2007, 3 pages.
ISA/EPO, Written Opinion for International Application No. PCT/US2006/018799, dated Mar. 22, 2007.
Oltersdorf et al., "An inhibitor of Bcl-2 family proteins induces regression of solid tumours," Nature, 2005, 435.
Petros et al., Solution structure of the antiapoptotic protein bcl-2, PNAS, 2001, 98 (6), 3012-3017.
Puck, et al., "Immune Disorders Caused by Defects in the Caspase Cascade," Current Allergy and Asthma Reports, 2003, 3, pp. 378-384.
Rengan. et al., "Actin cytoskeletal function is spared, but apoptosis is increased, in WAS patient hematopoietic cells," Blood, 2000, 95—Issue 4, pp. 1283-1292.
Sattler M. et al., Structure of Bcl-xL-Bak Peptide Complex: Recognition Between Regulators of Apoptosis, Science, 1997, 275, 983-986.
Shimazaki et al., "Evaluation of apoptosis as a prognostic factor in myelodysplastic syndromes", British J Haematology, 2000, 110 Issue 3, pp. 584-590.
Tse et al., "ABT-263: A Potent and Orally Bioavailable Bcl-2 Family Inhibitor," Cancer Research, 2008, 68—Issue9, pp. 3421-3428.
U.S.P.T.O., Examiners Amendment, dated Jul. 1, 2009, pp. 2-4, for U.S. Appl. No. 11/202,827.
U.S.P.T.O., Interview Summary, dated Jul. 1, 2009, p. 1, for U.S. Appl. No. 11/202,827.
U.S.P.T.O. Non-Final Office Action dated Sep. 12, 2008, in U.S. Appl. No. 11/202,827, filed Aug. 12, 2005.
U.S.P.T.O., Notice of Allowability, dated Jul. 1, 2009, p. 1-2, for U.S. Appl. No. 11/202,827.
U.S.P.T.O., Notice of Allowance and Fee(s) Due, dated Jul. 1, 2009, p. 1, for U.S. Appl. No. 11/202,827.
U.S.P.T.O., Office Action/Restriction Requirement dated Apr. 25, 2008, cover sheet and pp. 1-7, for U.S. Appl. No. 11/127,940.
Zhang et al., "Development of a high-throughput fluorescence polarization assay for Bcl-Xl," Analytical Biochemistry, 2002, 307, pp. 70-75.
ISA/RU, PCT Supplementary International Search Report mailed Feb. 9, 2012 for application No. PCT/US2010/058549.
Harrington E.A., et al., "VX-680, A Potent and Selective Small-Molecule Inhibitor of the Aurora Kinases, Suppresses Tumor Growth in Vivo," Nature Medicine, 2004, vol. 10 (3), pp. 262-267.
Kang M.H., et al., "Bcl-2 Inhibitors: Targeting Mitochondrial Apoptotic Pathways in Cancer Therapy," Clinical Cancer Research, 2009, vol. 15 (4), pp. 1126-1132.
Mason K.D., et al., "The BH3 Mimetic Compound, ABT-737, Synergizes with a Range of Cytotoxic Chemotherapy Agents in Chronic Lymphocytic Leukemia," Leukemia, 2009, vol. 23 (11), pp. 2034-2041.
Pan C., et al., "Aurora Kinase Small Molecule Inhibitor Destroys Mitotic Spindle, Suppresses Cell Growth, and Induces Apoptosis in Oral Squamous Cancer Cells," Oral Oncology, 2008, vol. 44 (7), pp. 639-645.
Shah O.J., et al., "Bcl-XL Represents a Druggable Molecular Vulnerability During Aurora B Inhibitor-Mediated Polyploidization," Proceedings of the National Academy of Sciences, 2010, vol. 107 (28), pp. 12634-12639.
Shoemaker A.R., et al., "The Bcl-2 Family Inhibitor ABT-263 Shows Significant Anti-Tumor Efficacy in Models of B Cell Non-Hodgkin's Lymphoma," Blood, 2006, vol. 108 (11), pp. 1-3.
Wilkinson R.W., et al., "AZD1152, a Selective Inhibitor of Aurora BKinase, Inhibits Human Tumor Xenograft Growth by Inducing Apoptosis," Clinical Cancer Research, 2007, vol. 13 (12), pp. 3682-3688.
Zong Z.P., et al., "Phorbol Myristate Induces Apoptosis of Taxol-Resistant Sarcoma Cells in Vitro," European Journal of Pharmacology, 2004, vol. 489 (1-2), pp. 3-11.
Chresta C.M., et al., "Hypersensitivity of Human Testicular Tumors to Etoposide-Induced Apoptosis is Associated with Functional P53 and a High Bax:Bcl-2 Ratio," Cancer Research, 1996, vol. 56 (8), pp. 1834-1841.
International Search Report for Application No. PCT/US2010/058549, mailed on May 3, 2011, 12 pages.
Kaestner P., et al., "Determinants for the Efficiency of Anticancer Drugs Targeting Either Aurora-A or Aurora-B Kinases in Human Colon Carcinoma Cells," Molecular Cancer Therapeutics, 2009, vol. 8 (7), pp. 2046-2056.
Li M., et al., "Aurora Kinase Inhibitor Zm447439 Induces Apoptosis via Mitochondrial Pathways," Biochemical Pharmacology, 2009, vol. 79 (2), pp. 122-129.
Li M., et al., "Inducing Apoptosis in Colorectal Tumor Cells Through Inhibition of Aurora B Kinase," European Journal of Cancer Supplements, 2007, vol. 5 (4), p. 59.
McCurrach M.E., et al., "Bax-Deficiency Promotes Drug Resistance and Oncogenic Transformation by Attenuating P53-Dependent Apoptosis," Proceedings of the National Academy of Sciences, 1997, vol. 94 (6), pp. 2345-2349.
Stoetzer O.J., et al., "Association of Bcl-2, Bax, Bcl-Xl and Interleukin-1 Beta-Converting Enzyme Expression with Initial Response to Chemotherapy in Acute Myeloid Leukemia," Leukemia, 1996, vol. 10 (suppl 3), pp. S18-S22.
Weber A., et al., "Endogenous Noxa Determines the Strong Proapoptotic Synergism of the BH3-Mimetic ABT-737 with Chemotherapeutic Agents in Human Melanoma Cells," Translational Oncology, 2009, vol. 2 (2), pp. 73-83.
Banker, Gilbert S. et al., Modern Pharmaceuticals, 1996, Marcel Dekker, New York, pp. 596 and 451.
Corbett et al., "Discovery and preclinical antitumor efficacy evaluations of LY32262 and LY33169," Investigational New Drugs, 2003, vol. 21(1):33-45.
Degterev, et al., "Identification of small-molecule inhibitors of interaction between the BH3 domain and Belx, "Nature Cell Biology, 2001, vol. 3, pp. 173-182.
Enyedy, et al., "Discovery of Small-Molecule Inhibitors ofBcl-2 through Structure-Based Computer Screening," J. Med. Chem., 2001, 44(25):4313-4324.
Oltersdorf, et al., "An inhibitor of Bcl-2 Family proteins induces regression of solid tumours", Nature, 2005, 435: 677-681.
Tse et al: "Supplemental Material and Methods:ABT-263: a potent and orally bioavailable Bcl-2 family inhibitor.", Cancer Research, (May 1, 2008), pp. 1-18.
Wang, et al., "A novel small molecule inhibitor of Bcl-XL inhibits tumor growth in a human head and neck squamous cell carcinoma xenograft model," Proceedings of the American Association for Cancer Research, Jul. 2003, vol. 44, 2nd Ed., p. 942, #4740 Abstract.
Wang, et al., "An Efficient Synthesis of ABT-263, a Novel Inhibition of Anti-apoptotic Hc1-2 Proteins," Synthesis, 2008, 15: 2398-2404.
Wang, et al., "Structure-based discovery of an organic compound that binds Bcl-2 protein and induces apoptosis of tumor cells," PNAS, Jun. 20, 2000, 97(13:) 7124-7129.
Wolff, Manfred E., Burger's Medicinal Chemistry and Drug Discovery, Fifth Ed. vol. 1: Principles and Practice, John Wiley & Sons, 1995, pp. 975-977.
U.S.P.T.O., Non-final Office Action dated Nov. 28, 2008 in U.S. Appl. No. 12/120,914.
U.S.P.T.O., Final Office Action dated Aug. 12, 2009 in U.S. Appl. No. 12/120,914.
ISA, PCT International Search Report dated May 13, 2005, in International Application No. PCT/US2004/036770, filed Nov. 3, 2004.

(56) References Cited

OTHER PUBLICATIONS

ISA, PCT International Preliminary Report on Patentability dated May 15, 2006, in International Application No. PCT/ US2004/ 036770, filed Nov. 3, 2004.

ISA, PCT International Search Report dated May 13, 2005, in International Application No. PCT/US2004/037911, filed Nov. 12, 2004.
ISA, PCT International Preliminary Report on Patentability dated May 15, 2006, in International Application No. PCT/ US2004/ 037911, filed Nov. 12, 2004.

* cited by examiner

US 8,624,027 B2

COMBINATION THERAPY FOR TREATING CANCER AND DIAGNOSTIC ASSAYS FOR USE THEREIN

This application is a continuation-in-part of U.S. Ser. No. 12/120,914, filed on May 15, 2008, which is a divisional of U.S. Ser. No. 11/432,937, filed on May 12, 2006, now U.S. Pat. No. 7,390,799, which claims priority to U.S. Provisional Application Ser. No. 60/718,618, Sep. 20, 2005 and U.S. Provisional Application Ser. No. 60/680,107, May 12, 2005.

SEQUENCE LISTING

The instant application contains a Sequence Listing which has been submitted via EFS-Web and is hereby incorporated by reference in its entirety. Said ASCII copy, created on Jan. 26, 2010, is named 7920USP1.txt, and is 3,179 bytes in size.

FIELD

The present disclosure relates to a combination of therapeutic agents for use in treating a patient a subject suffering from cancer. The combination comprises (1) at least one polyploidy inducing agent; and (b) at least one Bcl-2 family protein inhibitor. In addition, the present disclosure also relates to diagnostic assays useful in classification of patients for treatment with a polyploidy inducing agent, a Bcl-2 family protein inhibitor or a combination of a polyploidy inducing agent and a Bcl-2 family protein inhibitor. In particular, the present disclosure relates to identifying the presence or absence of at least one mutation in a BAX gene, a BAK gene or a NOXA gene and then classifying patients as eligible for receiving treatment with a polyploidy inducing agent, a Bcl-2 family protein inhibitor or a combination of a polyploidy inducing agent and a Bcl-2 family protein inhibitor.

BACKGROUND

Anti-apoptotic Bcl-2 family protein members are associated with a number of diseases and thus are under investigation as potential therapeutic drug targets. These important targets for interventional therapy include, for example, the Bcl-2 family of proteins Bcl-2, Bcl-$X_L$ and Bcl-w. Recently inhibitors of Bcl-2 family members have been reported in the literature, see, for example, WO 2005/049594, Oltersdorf, et. al., Nature, 435:677-681 (2005), U.S. Pat. No. 6,720,338 and U.S. Pat. No. 7,030,115. While this art teaches inhibitors having high binding to the target protein, this is only one of many parameters that must be considered as a compound is investigated for further or continued drug development. As part of this development, it is highly desirable to produce compounds that are efficacious in animal models of cancer after oral administration. To achieve this oral efficacy, it is well known in the art that a compound must not only display potent activity against a tumor type or cell line under investigation, but must also achieve acceptable levels of systemic exposure after oral administration. A typical measure of a compound's cellular activity is the concentration eliciting 50% cellular effect ($EC_{50}$). A typical measure of systemic exposure is the area under the curve resulting from graphing the plasma compound concentration after oral administration vs. time (AUC). The ratio between these parameters (AUC/$EC_{50}$) is well known in the art to constitute a useful pharmacodynamic parameter to predict oral efficacy.

In one aspect, this disclosure is directed to a series of haloalkylsulfonylaryl analogs that demonstrate enhanced and unexpected properties with respect to cellular efficacy and systemic exposure after oral administration in animals. Specifically, compounds of this disclosure maintain potent cellular efficacy while exhibiting suitable systemic exposure after oral administration to animals. This results in AUC/$EC_{50}$ ratios significantly higher than that of the compounds taught in the art. Other aspects of the disclosure are disclosed and apparent herein.

BRIEF DESCRIPTION OF THE FIGURES

FIG. 8A shows that VX-680 was screened at a single, fixed dose (1 μM) in combination with 19 other chemotherapeutics in 6-pt dose-response in a panel of 7 cell lines derived from various solid malignancies. Cell viability was determined 3 days after exposure to the combination regimens. Synergy or antagonism of drug combinations was determined using the Bliss additivism model of drug-drug interactions (See, Berenbaum, M. C., Cancer Res 35, 269-335 (1981)). The value in excess of Bliss additivism for each dose was determined for all combinations and defined as follows: >15=synergistic, 0-15=no interaction, <−15=antagonistic. These values are expressed in a heatmap using SPOTFIRE® (TIBCO®) data analysis software where synergy is indicated in red, no interaction in gray, and antagonism in blue. Each dose response included a point for VX-680 alone (0 μM combination compound). These values are not applicable for Bliss analysis and were excluded from the heatmap. Compounds tested in combination are shown at the right. The targets/mechanisms of action of each of these agents and the corresponding dose responses for the combination screen is summarized in Table A in EXAMPLE 40. FIG. 8B shows Bliss analysis of cell viability determinations for VX-680 in combination with ABT-263 in dose-response in D54MG, HCT116, SW620, A549, PC3, and EJ1 cells. FIG. 8C shows cell viability determinations analyzed in FIG. 8B.

FIG. 9A shows HCT116 colon carcinoma cells were either not transfected or transfected with the luciferase, Aurora A, or Aurora B siRNAs respectively. 24 hours post-transfection, cells were treated with ABT-263 in dose response, and cell viability was determined 72 hours after the addition of ABT-263. FIG. 9B shows immunoblots of HCT116 lysates demonstrated knockdown of target proteins 72 hours post-transfection with siRNAs used in FIG. 9A. MLN8054 (FIG. 9C) or AZD1152 (FIG. 9D) were tested in combination with DMSO or 1 µM ABT-263 in HCT116 cells. Cell viability was determined 72 hours after treatment. FIG. 9E shows immunoblots of HCT116 lysates demonstrated knockdown of Bcl-2, Bcl-$X_L$, and Mcl-1 72 hours post-transfection. EJ1 (FIG. 9F) or HCT116 (FIG. 9G) cells were transfected with a luciferase siRNA or the same set of siRNAs against Bcl-2, Bcl-$X_L$, or Mcl-1 siRNAs as in FIG. 9E. 24 hours post-transfection, cells were treated with different amounts of AZD1152. Cell viability was determined 72 hours after exposure to AZD1152. FIG. 9H shows HCT116 cells were transfected with different amount of Aurora B or Bcl-$X_L$ siRNAs individually or in combination. Cell viability was determined 72 hours post-transfection. In all figures, cell viability was expressed as the percentage of untransfected, DMSO-treated control cells. The red viability curve represents a synergistic combination.

FIG. 10A shows that HCT116 cells were transfected with INCENP or Bcl-$X_L$ siRNAs in dose-response individually or in combination. Cell viability was determined 72 hours post-transfection. The red curve represents a synergistic combination. FIG. 10B shows immunoblots of HCT116 lysates demonstrated knockdown of INCENP 72 hours post-transfection with the same siRNA as in FIG. 10A. HCT116 cells (FIG. 10C-FIG. 10F) were treated for 24 hours with DMSO or 200 nM AZD1152. AZD1152 was then either left in the culture medium (AZD 1152) or washed out by replacing the medium with drug-free growth medium (AZD 1152 washout). Cells were cultured for an additional 72 hours before being subjected to the following treatment/analysis: Western analysis (FIG. 10C) to determine the amounts of p53, phosphorylated (pSer$^{10}$) and unphosphorylated histone H3, or Phase contrast imaging (FIG. 10D) to show morphological signs of polyploidy, such as dramatically increased cell size and multinucleation, in AZD 1152 treated cells regardless of washout, further treatment of 1 µM ABT-263 for 4 hours (FIG. 10E) and assaying for Caspase-3 activity, and further treatment with 1 µM ABT-263 (FIG. 10F) for 24 hours and assaying for cell viability.

FIG. 12A shows a focused library of siRNAs targeting Bcl-2 network components was transfected as individual oligos into HCT116 cells. EJ1 and DLD1 cells (FIG. 12B) were transfected with individual NOXA siRNAs or BAX and BAK siRNAs in combination. In both FIG. 12A and FIG. 12B, 24 hours post-transfection, cells were treated with 200 nM AZD1152 to induce polyploidy. 72 hours after the addition of AZD1152, cells were treated with 1 µM ABT-263 and cell viability was determined 24 hours after the addition of ABT-263. HCT116 cells (FIG. 12C and FIG. 12D) were transfected with a control, nontargeting siRNA or a NOXA siRNA. 24 hours post-transfection, cells were treated with 200 nM AZD1152 for 72 hours. 1 µM ABT-263 was then added for 2 hours prior to cell lysis and immunoprecipitation of Bcl-$X_L$ or Mcl-1. HCT116 (FIG. 12E) cells were transfected with the focused siRNA library as in FIG. 12A. 24 hours post-transfection, cells were treated with 200 nM AZD1152 to induce polyploidy. AZD1152 was washed out by replacing the medium with drug-free growth medium 3 and 7 days after the addition of AZD1152. Cell viability was determined 10 days after the addition of AZD1152 to assess polyploidization-induced lethality.

FIG. 13A shows the growth curve of HCT116 tumors in mice when administered vehicle, ABT-263, AZD1152, or the combination of AZD1152 and ABT-263 as indicated in Example 40. CT116 tumor-bearing mice (FIG. 13B) were treated with vehicle or AZD 1152 (100 mg/kg/day (hereinafter "mkd", IP, QD) for 3 consecutive days prior to the administration of vehicle or ABT-263 (75 mkd, PO). 4 hours and 8 hours after the administration of ABT-263, tumors were collected, and tumor lysates were analyzed for the abundance of p53 and the conformationally active BAX (IP with 6A7, an antibody specifically detect active BAX, followed by BAX immunoblotting). FIG. 13C shows a model for Bcl-$X_L$ "addiction" and sensitivity to ABT-263 in polyploid cells. Polyploidization functionally neutralizes Mcl-1 by downregulating Mcl-1 protein, inducing NOXA, increasing the interaction of NOXA with Mcl-1, or some combination of these effects. Additionally, Bcl-$X_L$ becomes burdened by BH3-only proteins, such as tBID and BIK. This renders cell survival increasingly dependent upon Bcl-$X_L$. This dependence or "addiction" represents a molecular Achilles' heel of polyploidization, as ABT-263, which disables the anti-apoptotic function of Bcl-$X_L$, elicits rapid and robust apoptosis in polyploid tumor cells.

SUMMARY

Figure 1:
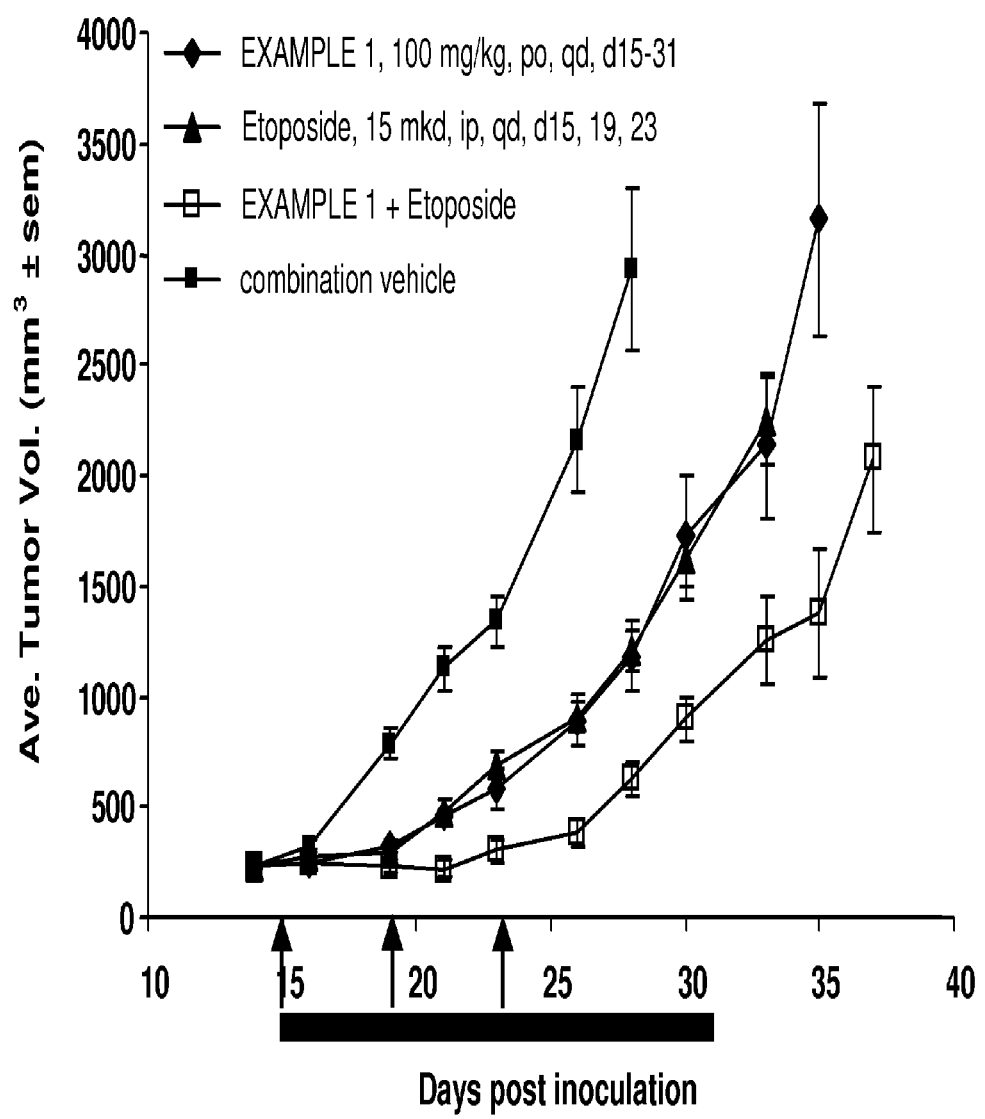
FIG. 1 shows comparative antitumorigenesis of EXAMPLE 1, etoposide and combinations thereof on B-cell lymphoma.
Figure 2:
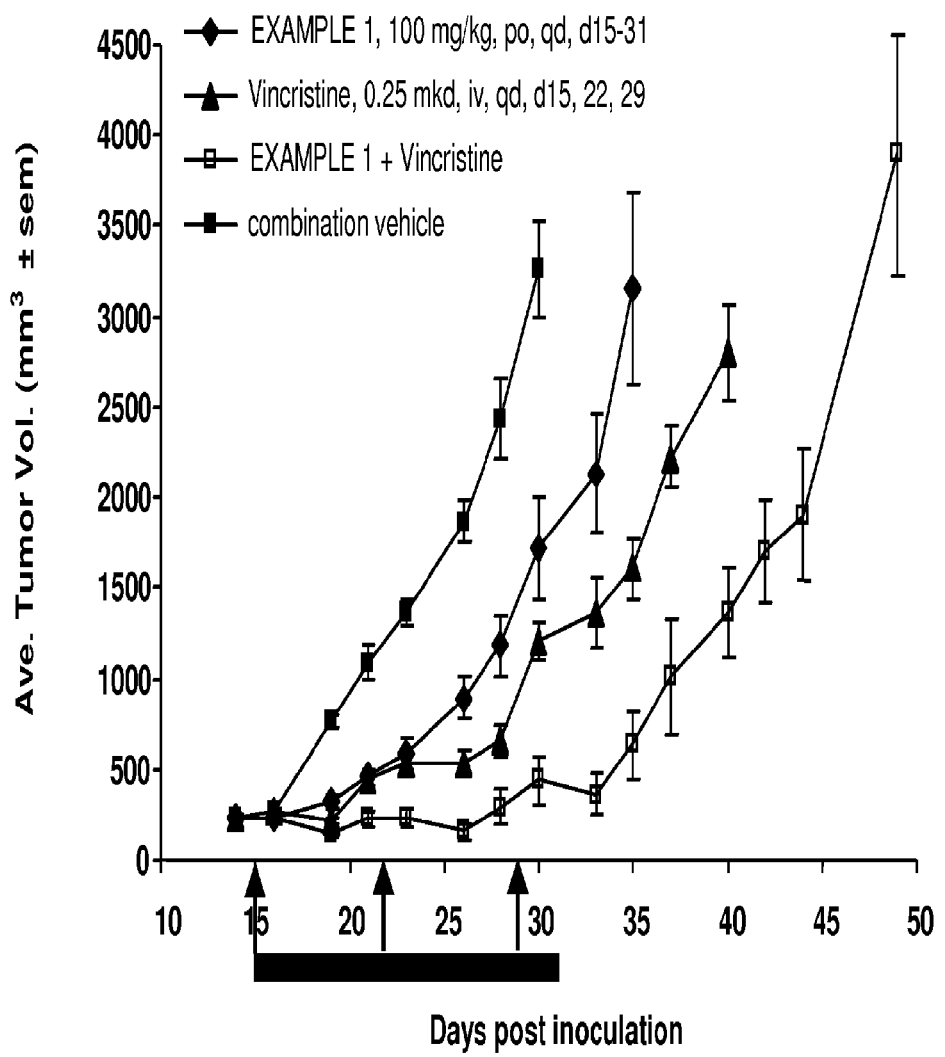
FIG. 2 shows comparative antitumorigenesis of EXAMPLE 1, vincristine and combinations thereof on B-cell lymphoma.
Figure 3:
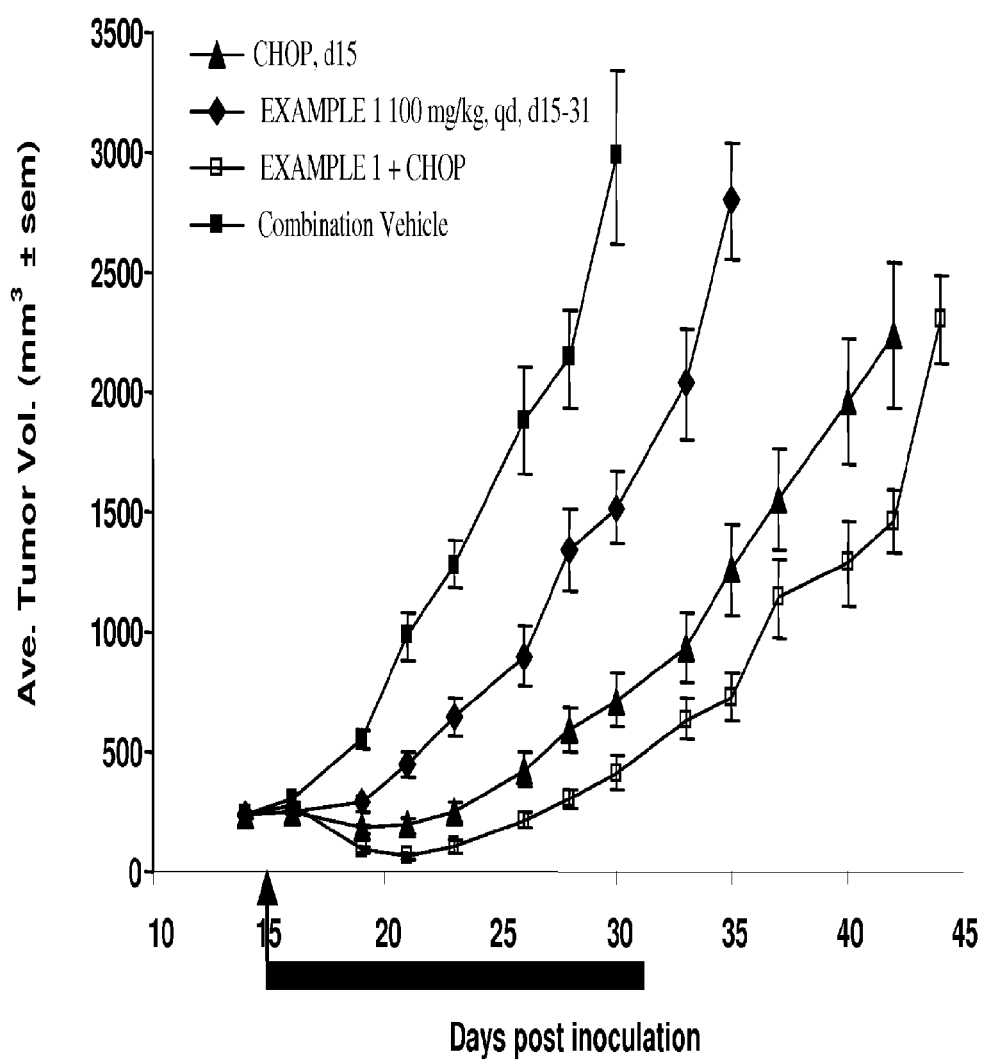
FIG. 3 shows comparative antitumorigenesis of EXAMPLE 1, CHOP and combinations thereof on B-cell lymphoma.
Figure 4:
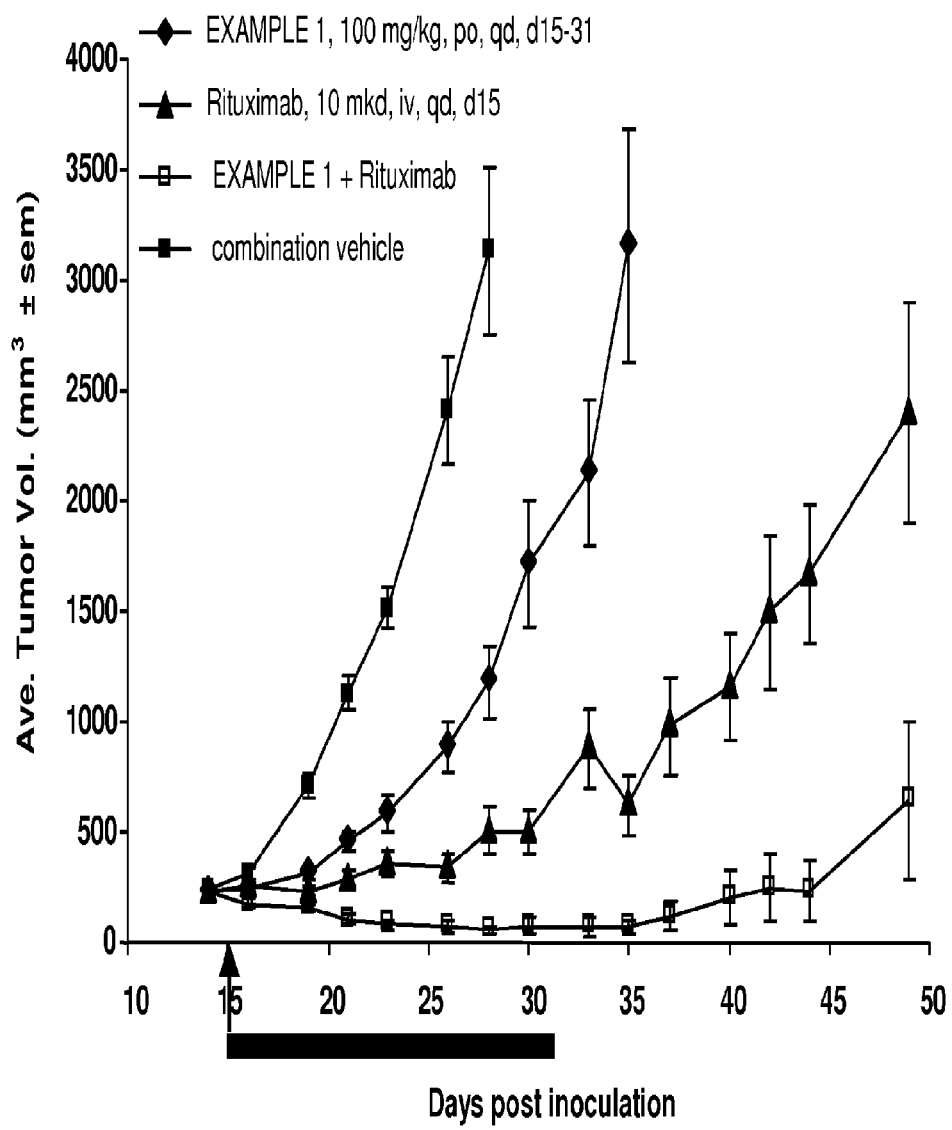
FIG. 4 shows comparative antitumorigenesis of EXAMPLE 1, rituximab and combinations thereof on B-cell lymphoma.
Figure 5:
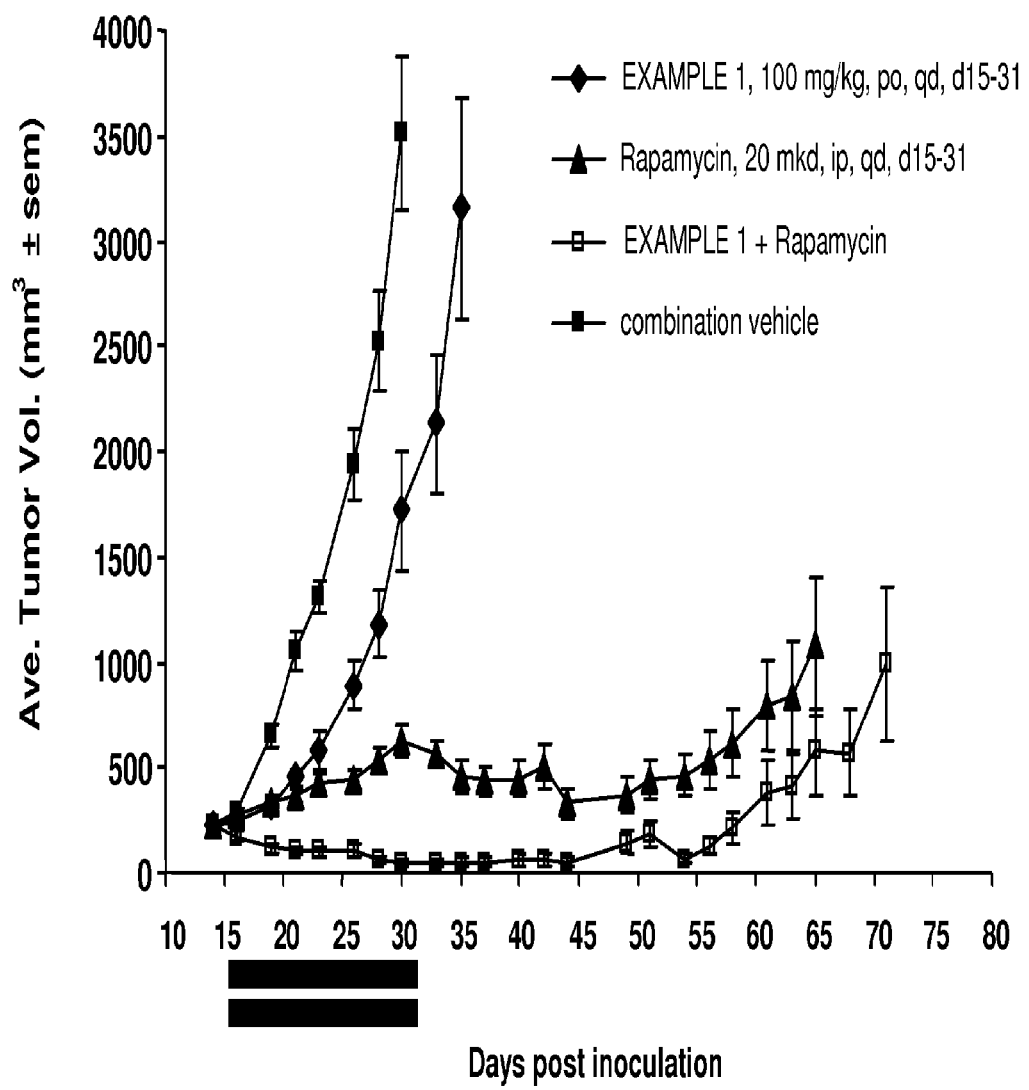
FIG. 5 shows comparative antitumorigenesis of EXAMPLE 1, rapamycin and combinations thereof on B-cell lymphoma.
Figure 6:
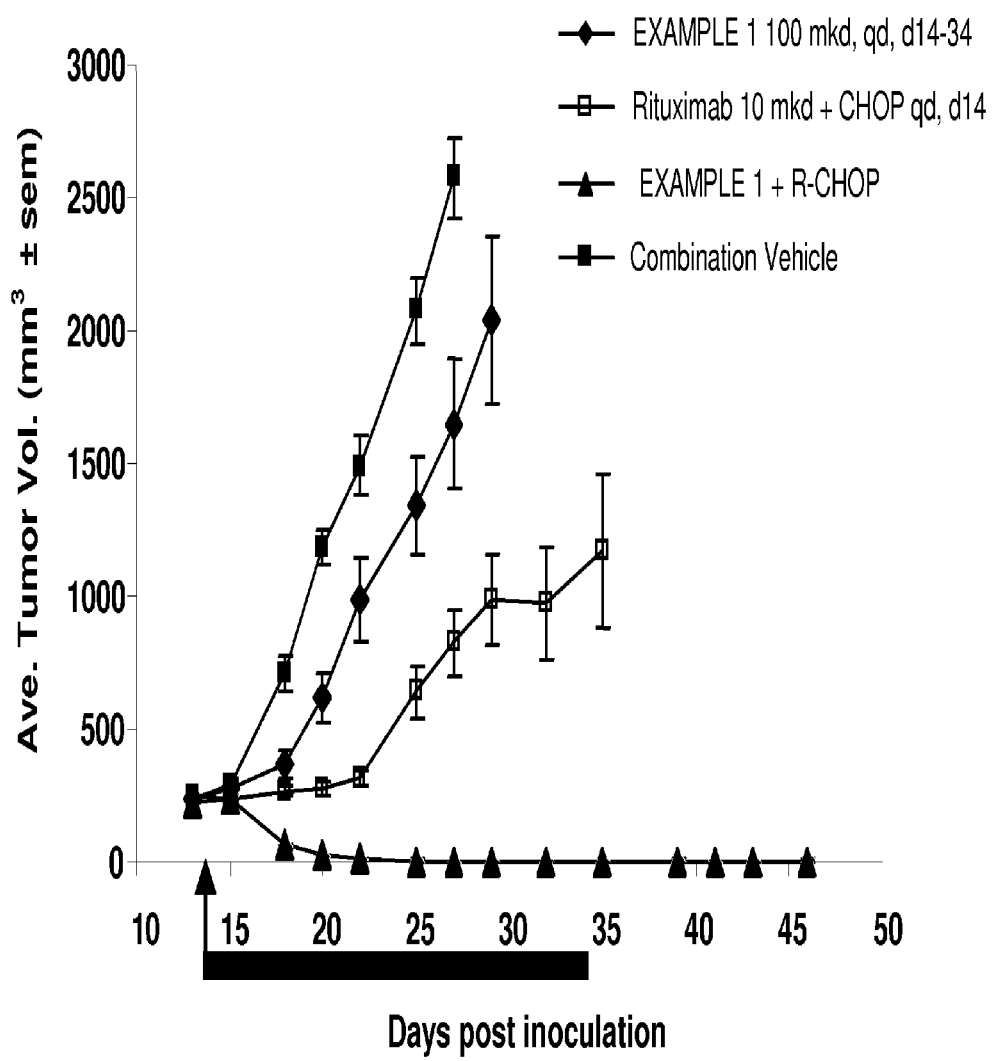
FIG. 6 shows comparative antitumorigenesis of EXAMPLE 1, R—CHOP and combinations thereof on mantle cell lymphoma.
Figure 7:
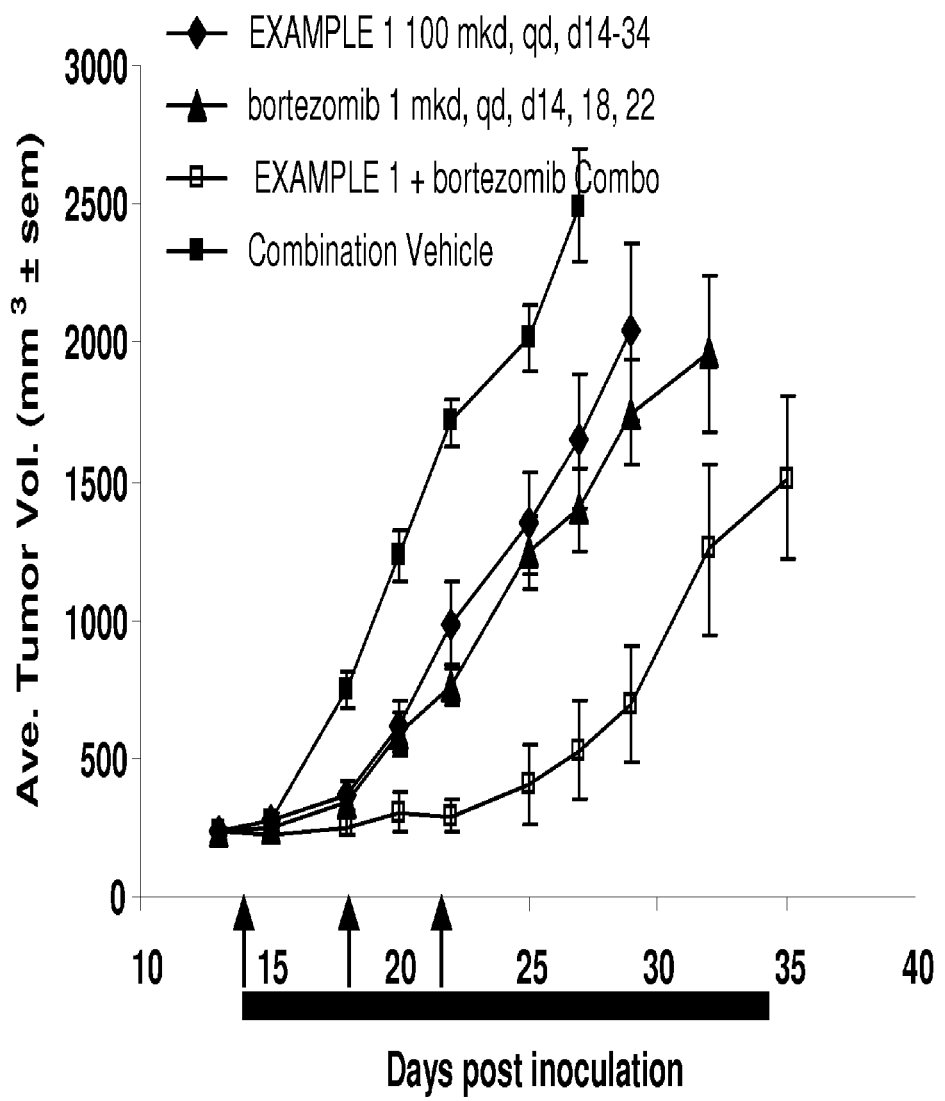
FIG. 7 shows comparative antitumorigenesis of EXAMPLE 1, bortezomib and combinations thereof on mantle cell lymphoma.

In one aspect, the present disclosure comprises compounds having formula (II)

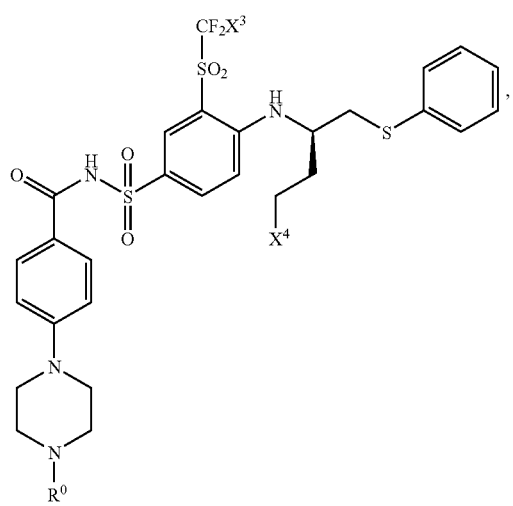

and therapeutically acceptable salts, prodrugs, salts of prodrugs and metabolites thereof, wherein $X^3$ is Cl or F;

$X^4$ is azepan-1-yl, morpholin-1-yl, 1,4-oxazepan-4-yl, pyrrolidin-1-yl, $N(CH_3)_2$, $N(CH_3)(CH(CH_3)_2)$, 7-azabicyclo[2.2.1]heptan-1-yl or 2-oxa-5-azabicyclo[2.2.1]hept-5-yl, and $R^0$ is

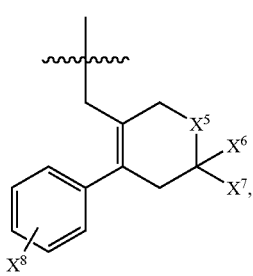

wherein
$X^5$ is $CH_2$, $C(CH_3)_2$ or $CH_2CH_2$;
$X^6$ and $X^7$ are both hydrogen or are both methyl; and
$X^8$ is F, Cl, Br or I; or $X^4$ is azepan-1-yl, morpholin-1-yl, pyrrolidin-1-yl, $N(CH_3)(CH(CH_3)_2)$ or 7-azabicyclo[2.2.1]heptan-1-yl, and $R^0$ is

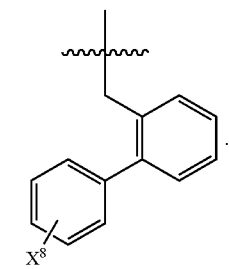

or
$X^4$ is $N(CH_3)_2$ or morpholin-1-yl, and $R^0$ is

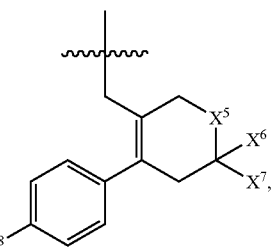

Another aspect comprises compounds having formula (II), and therapeutically acceptable salts, prodrugs, salts of prodrugs and metabolites thereof, wherein $X^3$ is Cl or F;

$X^4$ is azepan-1-yl, morpholin-1-yl, 1,4-oxazepan-4-yl, pyrrolidin-1-yl, $N(CH_3)_2$, $N(CH_3)(CH(CH_3)_2)$, 7-azabicyclo[2.2.1]heptan-1-yl or 2-oxa-5-azabicyclo[2.2.1]hept-5-yl, and $R^0$ is

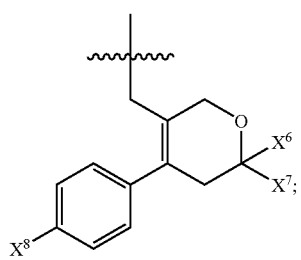

wherein
$X^5$ is $CH_2$, $C(CH_3)_2$ or $CH_2CH_2$;
$X^6$ and $X^7$ are both hydrogen or are both methyl; and
$X^8$ is F, Cl, Br or I; or $X^4$ is azepan-1-yl, morpholin-1-yl, pyrrolidin-1-yl, $N(CH_3)(CH(CH_3)_2)$ or 7-azabicyclo[2.2.1]heptan-1-yl, and $R^0$ is or X⁴ is N(CH₃)₂ or morpholin-1-yl, and R⁰ is

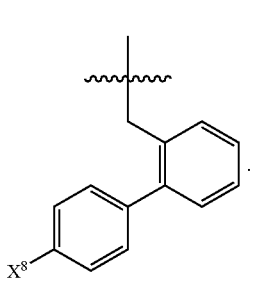

Still another aspect comprises compounds having formula (II), and therapeutically acceptable salts, prodrugs, salts of prodrugs and metabolites thereof, wherein X³ is Cl or F;

X⁴ is azepan-1-yl, morpholin-1-yl, 1,4-oxazepan-4-yl, pyrrolidin-1-yl, N(CH₃)₂, N(CH₃)(CH(CH₃)₂), 7-azabicyclo[2.2.1]heptan-1-yl or 2-oxa-5-azabicyclo[2.2.1]hept-5-yl, and R⁰ is

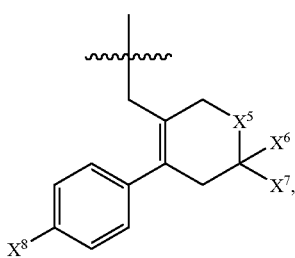

wherein X⁵ is CH₂, C(CH₃)₂ or CH₂CH₂, and X⁶ and X⁷ are both hydrogen or are both methyl; and X⁸ is F, Cl, Br or I.

Still another aspect comprises compounds having formula (II), and therapeutically acceptable salts, prodrugs, salts of prodrugs and metabolites thereof, wherein X³ is Cl or F;

X⁴ is azepan-1-yl, morpholin-1-yl, pyrrolidin-1-yl, N(CH₃)(CH(CH₃)₂) or 7-azabicyclo[2.2.1]heptan-1-yl;

R⁰ is

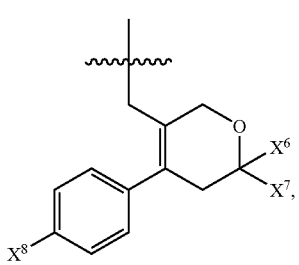

wherein X⁶ and X⁷ are both hydrogen or are both methyl; and

X⁸ is F, Cl, Br or I.

Still another aspect comprises compounds having formula (II), and therapeutically acceptable salts, prodrugs, salts of prodrugs and metabolites thereof, wherein X³ is Cl or F;

X⁴ is N(CH₃)₂ or morpholin-1-yl;

R⁰ is

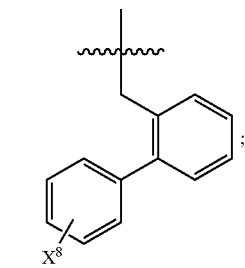

and

X⁸ is F, Cl, Br or I.

Still another aspect comprises a compound having formula (II), and therapeutically acceptable salts, prodrugs, salts of prodrugs and metabolites thereof, wherein X³ is F; X⁴ is morpholin-1-yl;

R⁰ is

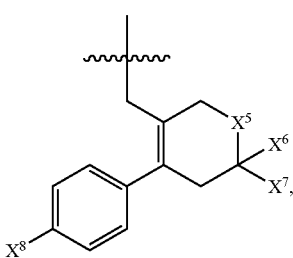

wherein X⁵ is C(CH₃)₂; X⁶ and X⁷ are both methyl; and

X⁸ is Cl.

Still another aspect comprises
N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide (alternatively referred to herein as ABT-263), 3-((chloro(difluoro)methyl)sulfonyl)-N-(4-(4-((2-(4-chlorophenyl)-4,4-dimethylcyclohex-1-en-1-yl)methyl)piperazin-1-yl)benzoyl)-4-(((1R)-3-(morpholin-4-yl)-1-((phenylsulfanyl)methyl)propyl)amino)benzenesulfonamide, 3-((chloro(difluoro)methyl)sulfonyl)-N-(4-(4-((2-(4-chlorophenyl)-1-cyclohex-1-en-1-yl)methyl)piperazin-1-yl)benzoyl)-4-(((1R)-3-(morpholin-4-yl)-1-((phenylsulfanyl)methyl)propyl)amino)benzenesulfonamide, N-(4-(4-((2-(4-chlorophenyl)-5,5-dimethylcyclohex-1-en-1-yl)methyl)piperazin-1-yl)benzoyl)-4-(((1R)-3-(isopropyl(methyl)amino)-1-((phenylsulfanyl)methyl)propyl)amino)-3-((trifluoromethyl)sulfonyl)benzenesulfonamide, N-(4-(4-((2-(4-chlorophenyl)-1-cyclohepten-1-yl)methyl)piperazin-1-yl)benzoyl)-4-(((1R)-3-(isopropyl(methyl)amino)-1-((phenylsulfanyl)methyl)propyl)amino)-3-((trifluoromethyl)sulfonyl)benzenesulfonamide, 3-((chloro(difluoro)methyl)sulfonyl)-N-(4-(4-((2-(4-chlorophenyl)cyclohex-1-en-1-yl)methyl)piperazin-1-yl)benzoyl)-4-(((1R)-3-((1S,4S)-2-oxa-5-azabicyclo[2.2.1]hept-5-yl)-1-((phenylsulfanyl)methyl)propyl)amino)benzenesulfonamide, N-(4-(4-((2-(4-chlorophenyl)cyclohex-1-en-1-yl)methyl)piperazin-1-yl)benzoyl)-4-((((1R)-3-(morpholin-4-yl)-1-

((phenylsulfanyl)methyl)propyl)amino)-3-((trifluoromethyl)sulfonyl)benzenesulfonamide, 4-(((1R)-3-(7-azabicyclo[2.2.1]hept-7-yl)-1-((phenylsulfanyl)methyl)propyl)amino)-N-(4-(4-((2-(4-chlorophenyl)cyclohex-1-en-1-yl)methyl)piperazin-1-yl)benzoyl)-3-((trifluoromethyl)sulfonyl)benzenesulfonamide, N-(4-(4-((2-(4-chlorophenyl)cyclohex-1-en-1-yl)methyl)piperazin-1-yl)benzoyl)-4-(((1R)-3-(2-oxa-5-azabicyclo[2.2.1]hept-5-yl)-1-((phenylsulfanyl)methyl)propyl)amino)-3-((trifluoromethyl)sulfonyl)benzenesulfonamide, N-(4-(4-((2-(4-chlorophenyl)-5,5-dimethylcyclohex-1-en-1-yl)methyl)piperazin-1-yl)benzoyl)-4-(((1R)-3-(2-oxa-5-azabicyclo[2.2.1]hept-5-yl)-1-((phenylsulfanyl)methyl)propyl)amino)-3-((trifluoromethyl)sulfonyl)benzenesulfonamide, 3-((chloro(difluoro)methyl)sulfonyl)-N-(4-(4-((2-(4-chlorophenyl)-5,5-dimethylcyclohex-1-en-1-yl)methyl)piperazin-1-yl)benzoyl)-4-(((1R)-3-(2-oxa-5-azabicyclo[2.2.1]hept-5-yl)-1-((phenylsulfanyl)methyl)propyl)amino)benzenesulfonamide, N-(4-(4-((2-(4-chlorophenyl)cyclohept-1-en-1-yl)methyl)piperazin-1-yl)benzoyl)-4-(((1R)-3-(2-oxa-5-azabicyclo[2.2.1]hept-5-yl)-1-((phenylsulfanyl)methyl)propyl)amino)-3-((trifluoromethyl)sulfonyl)benzenesulfonamide, 3-((chloro(difluoro)methyl)sulfonyl)-N-(4-(4-((2-(4-chlorophenyl)cyclohept-1-en-1-yl)methyl)piperazin-1-yl)benzoyl)-4-(((1R)-3-(2-oxa-5-azabicyclo[2.2.1]hept-5-yl)-1-((phenylsulfanyl)methyl)propyl)amino)benzenesulfonamide, N-(4-(4-((2-(4-chlorophenyl)-4,4-dimethylcyclohex-1-en-1-yl)methyl)piperazin-1-yl)benzoyl)-4-(((1R)-3-(isopropyl(methyl)amino)-1-((phenylsulfanyl)methyl)propyl)amino)-3-((trifluoromethyl)sulfonyl)benzenesulfonamide, N-(4-(4-((2-(4-chlorophenyl)cyclohex-1-en-1-yl)methyl)piperazin-1-yl)benzoyl)-4-(((1R)-3-(1,4-oxazepan-4-yl)-1-((phenylsulfanyl)methyl)propyl)amino)-3-((trifluoromethyl)sulfonyl)benzenesulfonamide, 4-(((1R)-3-(azepan-1-yl)-1-((phenylsulfanyl)methyl)propyl)amino)-N-(4-(4-((2-(4-chlorophenyl)-1-cyclohex-1-en-1-yl)methyl)piperazin-1-yl)benzoyl)-3-((trifluoromethyl)sulfonyl)benzenesulfonamide, N-(4-(4-((2-(4-chlorophenyl)cyclohept-1-en-1-yl)methyl)piperazin-1-yl)benzoyl)-4-(((1R)-3-(dimethylamino)-1-((phenylsulfanyl)methyl)propyl)amino)-3-((trifluoromethyl)sulfonyl)benzenesulfonamide, 3-((chloro(difluoro)methyl)sulfonyl)-N-(4-(4-((2-(4-chlorophenyl)cyclohex-1-en-1-yl)methyl)piperazin-1-yl)benzoyl)-4-(((1R)-3-(dimethylamino)-1-((phenylsulfanyl)methyl)propyl)amino)benzenesulfonamide, 3-((chloro(difluoro)methyl)sulfonyl)-N-(4-(4-((2-(4-chlorophenyl)-5,5-dimethylcyclohex-1-en-1-yl)methyl)piperazin-1-yl)benzoyl)-4-(((1R)-3-(morpholin-4-yl)-1-((phenylsulfanyl)methyl)propyl)amino)benzenesulfonamide, N-(4-(4-((2-(4-chlorophenyl)-5,5-dimethyl-1-cyclohex-1-en-1-yl)methyl)piperazin-1-yl)benzoyl)-4-(((1R)-3-(dimethylamino)-1-((phenylsulfanyl)methyl)propyl)amino)-3-((trifluoromethyl)sulfonyl)benzenesulfonamide, N-(4-(4-((4-(4-chlorophenyl)-5,6-dihydro-2H-pyran-3-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide, 3-((chloro(difluoro)methyl)sulfonyl)-N-(4-(4-((2-(4-chlorophenyl)-4,4-dimethylcyclohex-1-en-1-yl)methyl)piperazin-1-yl)benzoyl)-4-(((1R)-3-(isopropyl(methyl)amino)-1-((phenylsulfanyl)methyl)propyl)amino)benzenesulfonamide, 3-((chloro(difluoro)methyl)sulfonyl)-N-(4-(4-((2-(4-chlorophenyl)-5,5-dimethylcyclohex-1-en-1-yl)methyl)piperazin-1-yl)benzoyl)-4-(((1R)-3-(isopropyl(methyl)amino)-1-((phenylsulfanyl)methyl)propyl)amino)benzenesulfonamide, N-(4-(4-((2-(4-chlorophenyl)-4,4-dimethylcyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide, 3-((chloro(difluoro)methyl)sulfonyl)-N-(4-(4-((2-(4-chlorophenyl)-4,4-dimethylcyclohex-1-en-1-yl)methyl)piperazin-1-yl)benzoyl)-4-(((1R)-3-((1S,4S)-2-oxa-5-azabicyclo[2.2.1]hept-5-yl)-1-((phenylsulfanyl)methyl)propyl)amino)benzenesulfonamide, N-(4-(4-((2-(4-chlorophenyl)cyclohex-1-en-1-yl)methyl)piperazin-1-yl)benzoyl)-4-(((1R)-3-(dimethylamino)-1-((phenylsulfanyl)methyl)propyl)amino)-3-((trifluoromethyl)sulfonyl)benzenesulfonamide, N-(4-(4-((2-(4-chlorophenyl)cyclohex-1-en-1-yl)methyl)piperazin-1-yl)benzoyl)-4-(((1R)-1-((phenylsulfanyl)methyl)-3-(pyrrolidin-1-yl)propyl)amino)-3-((trifluoromethyl)sulfonyl)benzenesulfonamide, 3-((chloro(difluoro)methyl)sulfonyl)-N-(4-(4-((2-(4-chlorophenyl)-4,4-dimethylcyclohex-1-en-1-yl)methyl)piperazin-1-yl)benzoyl)-4-(((1R)-3-(dimethylamino)-1-((phenylsulfanyl)methyl)propyl)amino)benzenesulfonamide, N-(4-(4-((2-(4-chlorophenyl)cyclohept-1-en-1-yl)methyl)piperazin-1-yl)benzoyl)-4-(((1R)-1-((phenylsulfanyl)methyl)-3-(pyrrolidin-1-yl)propyl)amino)-3-((trifluoromethyl)sulfonyl)benzenesulfonamide, 3-((chloro(difluoro)methyl)sulfonyl)-N-(4-(4-((2-(4-chlorophenyl)-5,5-dimethylcyclohex-1-en-1-yl)methyl)piperazin-1-yl)benzoyl)-4-(((1R)-1-((phenylsulfanyl)methyl)-3-(pyrrolidin-1-yl)propyl)amino)benzenesulfonamide, 3-((chloro(difluoro)methyl)sulfonyl)-N-(4-(4-((2-(4-chlorophenyl)-4,4-dimethylcyclohex-1-en-1-yl)methyl)piperazin-1-yl)benzoyl)-4-(((1R)-1-((phenylsulfanyl)methyl)-3-(pyrrolidin-1-yl)propyl)amino)benzenesulfonamide, 3-((chloro(difluoro)methyl)sulfonyl)-N-(4-(4-((2-(4-chlorophenyl)cyclohept-1-en-1-yl)methyl)piperazin-1-yl)benzoyl)-4-(((1R)-1-((phenylsulfanyl)methyl)-3-(pyrrolidin-1-yl)propyl)amino)benzenesulfonamide, N-(4-(4-((2-(4-chlorophenyl)cyclohex-1-en-1-yl)methyl)piperazin-1-yl)benzoyl)-4-(((1R)-3-(isopropyl(methyl)amino)-1-((phenylsulfanyl)methyl)propyl)amino)-3-((trifluoromethyl)sulfonyl)benzenesulfonamide, N-(4-(4-((2-(4-chlorophenyl)-4,4-dimethylcyclohex-1-en-1-yl)methyl)piperazin-1-yl)benzoyl)-4-(((1R)-1-((phenylsulfanyl)methyl)-3-(pyrrolidin-1-yl)propyl)amino)-3-((trifluoromethyl)sulfonyl)benzenesulfonamide, 3-((chloro(difluoro)methyl) sulfonyl)-N-(4-(4-((2-(4-chlorophenyl)cyclohex-1-en-1-yl)methyl)piperazin-1-yl)benzoyl)-4-(((1R)-1-((phenylsulfanyl)methyl)-3-(pyrrolidin-1-yl)propyl)amino)benzenesulfonamide, N-(4-(4-((2-(4-chlorophenyl)-4,4-dimethylcyclohex-1-en-1-yl)methyl)piperazin-1-yl)benzoyl)-4-(((1R)-3-(dimethylamino)-1-((phenylsulfanyl)methyl)propyl)amino)-3-((trifluoromethyl)sulfonyl)benzenesulfonamide, N-(4-(4-((2-(4-chlorophenyl)-4,4-dimethylcyclohex-1-en-1-yl)methyl)piperazin-1-yl)benzoyl)-4-(((1R)-3-((1S,4S)-2-oxa-5-azabicyclo[2.2.1]hept-5-yl)-1-((phenylsulfanyl)methyl)propyl)amino)-3-((trifluoromethyl)sulfonyl)benzenesulfonamide, N-(4-(4-(((4'-chloro(1,1'-biphenyl)-2-yl)methyl)-1-piperazinyl)benzoyl)-4-(((1R)-3-(dimethylamino)-1-((phenylsulfanyl)methyl)propyl)amino)-3-((trifluoromethyl)sulfonyl)benzenesulfonamide, and N-(4-(4-(((4'-chloro(1,1'-biphenyl)-2-yl)methyl)-1-piperazinyl)benzoyl)-4-(((1R)-3-(4-morpholinyl)-1-((phenylsulfanyl)methyl)propyl)amino)-3-((trifluoromethyl)sulfonyl)benzenesulfonamide, and therapeutically acceptable salts, prodrugs, salts of prodrugs and metabolites thereof.

Still another aspect comprises compositions for treating diseases during which are expressed one or more than one of antiapoptotic Bcl-$X_L$ protein, antiapoptotic Bcl-2 protein or antiapoptotic Bcl-w protein, said compositions comprising an excipient and a therapeutically effective amount of the compound having formula (II).

Still another aspect comprises methods of treating diseases in a patient during which are expressed one or more than one of antiapoptotic Bcl-$X_L$ protein, antiapoptotic Bcl-2 protein or antiapoptotic Bcl-w protein, said methods comprising administering to the patient a therapeutically effective amount of a compound having formula (II).

Still another aspect comprises compositions comprising an excipient and a therapeutically effective amount of the compound having formula (II) for treating diseases of abnormal cell growth and/or dysregulated apoptosis, such as cancer, including, for example, mesothioloma, bladder cancer, pancreatic cancer, skin cancer, cancer of the head or neck, cutaneous or intraocular melanoma, ovarian cancer, breast cancer, uterine cancer, carcinoma of the fallopian tubes, carcinoma of the endometrium, carcinoma of the cervix, carcinoma of the vagina, carcinoma of the vulva, bone cancer, ovarian cancer, cervical cancer, colon cancer, rectal cancer, cancer of the anal region, stomach cancer, gastrointestinal (gastric, colorectal, and duodenal), chronic lymphocytic leukemia, esophageal cancer, cancer of the small intestine, cancer of the endocrine system, cancer of the thyroid gland, cancer of the parathyroid gland, cancer of the adrenal gland, sarcoma of soft tissue, cancer of the urethra, cancer of the penis, testicular cancer, hepatocellular cancer (hepatic and billiary duct), primary or secondary central nervous system tumor, primary or secondary brain tumor, Hodgkin's disease, chronic or acute leukemia, chronic myeloid leukemia, lymphocytic lymphomas, lymphoblastic leukemia, follicular lymphoma, lymphoid malignancies of T-cell or B-cell origin, melanoma, multiple myeloma, oral cancer, ovarian cancer, non-small cell lung cancer, prostate cancer, small cell lung cancer, cancer of the kidney and ureter, renal cell carcinoma, carcinoma of the renal pelvis, neoplasms of the central nervous system, primary central nervous system lymphoma, non Hodgkin's lymphoma, spinal axis tumors, brain stem glioma, pituitary adenoma, adrenocortical cancer, gall bladder cancer, cancer of the spleen, cholangiocarcinoma, fibrosarcoma, neuroblastoma, retinoblastoma, or a combination thereof.

Still another aspect comprises methods of treating mesothioloma, bladder cancer, pancreatic cancer, skin cancer, cancer of the head or neck, cutaneous or intraocular melanoma, ovarian cancer, breast cancer, uterine cancer, carcinoma of the fallopian tubes, carcinoma of the endometrium, carcinoma of the cervix, carcinoma of the vagina, carcinoma of the vulva, bone cancer, ovarian cancer, cervical cancer, colon cancer, rectal cancer, cancer of the anal region, stomach cancer, gastrointestinal (gastric, colorectal, and duodenal), chronic lymphocytic leukemia, esophageal cancer, cancer of the small intestine, cancer of the endocrine system, cancer of the thyroid gland, cancer of the parathyroid gland, cancer of the adrenal gland, sarcoma of soft tissue, cancer of the urethra, cancer of the penis, testicular cancer, hepatocellular cancer (hepatic and billiary duct), primary or secondary central nervous system tumor, primary or secondary brain tumor, Hodgkin's disease, chronic or acute leukemia, chronic myeloid leukemia, lymphocytic lymphomas, lymphoblastic leukemia, follicular lymphoma, lymphoid malignancies of T-cell or B-cell origin, melanoma, multiple myeloma, oral cancer, ovarian cancer, non-small cell lung cancer, prostate cancer, small cell lung cancer, cancer of the kidney and ureter, renal cell carcinoma, carcinoma of the renal pelvis, neoplasms of the central nervous system, primary central nervous system lymphoma, non Hodgkin's lymphoma, spinal axis tumors, brain stem glioma, pituitary adenoma, adrenocortical cancer, gall bladder cancer, cancer of the spleen, cholangiocarcinoma, fibrosarcoma, neuroblastoma, retinoblastoma, or a combination of one or more of the above cancers in a patient, said methods comprising administering thereto a therapeutically effective amount of a compound having formula (II).

Still another aspect comprises compositions for treating bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, prostate cancer, small cell lung cancer and spleen cancer, said compositions comprising an excipient and a therapeutically effective amount of the compound having formula (II).

Still another aspect comprises methods of treating bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, prostate cancer, small cell lung cancer and spleen cancer in a patient, said methods comprising administering to the patient a therapeutically effective amount of a compound having formula (II).

Still another aspect comprises compositions for treating diseases in a patient during which are expressed one or more than one of antiapoptotic Bcl-$X_L$ protein, antiapoptotic Bcl-2 protein or antiapoptotic Bcl-w protein, said compositions comprising an excipient and a therapeutically effective amount of the compound having formula (II) and a therapeutically effective amount of one additional therapeutic agent or more than one additional therapeutic agent.

Still another aspect comprises methods of treating diseases in a patient during which is expressed one or more than one of antiapoptotic Bcl-$X_L$ protein, antiapoptotic Bcl-2 protein or antiapoptotic Bcl-w protein, said methods comprising administering to the patient a therapeutically effective amount of a compound having formula (II) and a therapeutically effective amount of one additional therapeutic agent or more than one additional therapeutic agent.

Still another aspect comprises compositions for treating mesothioloma, bladder cancer, pancreatic cancer, skin cancer, cancer of the head or neck, cutaneous or intraocular melanoma, ovarian cancer, breast cancer, uterine cancer, carcinoma of the fallopian tubes, carcinoma of the endometrium, carcinoma of the cervix, carcinoma of the vagina, carcinoma of the vulva, bone cancer, ovarian cancer, cervical cancer, colon cancer, rectal cancer, cancer of the anal region, stomach cancer, gastrointestinal (gastric, colorectal, and duodenal), chronic lymphocytic leukemia, esophageal cancer, cancer of the small intestine, cancer of the endocrine system, cancer of the thyroid gland, cancer of the parathyroid gland, cancer of the adrenal gland, sarcoma of soft tissue, cancer of the urethra, cancer of the penis, testicular cancer, hepatocellular cancer (hepatic and billiary duct), primary or secondary central nervous system tumor, primary or secondary brain tumor, Hodgkin's disease, chronic or acute leukemia, chronic myeloid leukemia, lymphocytic lymphomas, lymphoblastic leukemia, follicular lymphoma, lymphoid malignancies of T-cell or B-cell origin, melanoma, multiple myeloma, oral cancer, ovarian cancer, non-small cell lung cancer, prostate cancer, small cell lung cancer, cancer of the kidney and ureter, renal cell carcinoma, carcinoma of the renal pelvis, neoplasms of the central nervous system, primary central nervous system lymphoma, non Hodgkin's lymphoma, spinal axis tumors, brain stem glioma, pituitary adenoma, adrenocortical cancer, gall bladder cancer, cancer of the spleen, cholangiocarcinoma, fibrosarcoma, neuroblastoma, retinoblastoma, or a combination of one or more of the above cancers, said compositions comprising an excipient and therapeutically effective amount of a compound having formula (II) and one additional therapeutic agent or more than one additional therapeutic agent.

Still another aspect comprises methods of treating mesothioloma, bladder cancer, pancreatic cancer, skin cancer, cancer of the head or neck, cutaneous or intraocular melanoma, ovarian cancer, breast cancer, uterine cancer, carcinoma of the fallopian tubes, carcinoma of the endometrium, carcinoma of the cervix, carcinoma of the vagina, carcinoma of the vulva, bone cancer, ovarian cancer, cervical cancer, colon cancer, rectal cancer, cancer of the anal region, stomach cancer, gastrointestinal (gastric, colorectal, and duodenal), chronic lymphocytic leukemia, esophageal cancer, cancer of the small intestine, cancer of the endocrine system, cancer of the thyroid gland, cancer of the parathyroid gland, cancer of the adrenal gland, sarcoma of soft tissue, cancer of the urethra, cancer of the penis, testicular cancer, hepatocellular cancer (hepatic and billiary duct), primary or secondary central nervous system tumor, primary or secondary brain tumor, Hodgkin's disease, chronic or acute leukemia, chronic myeloid leukemia, lymphocytic lymphomas, lymphoblastic leukemia, follicular lymphoma, lymphoid malignancies of T-cell or B-cell origin, melanoma, multiple myeloma, oral cancer, ovarian cancer, non-small cell lung cancer, prostate cancer, small cell lung cancer, cancer of the kidney and ureter, renal cell carcinoma, carcinoma of the renal pelvis, neoplasms of the central nervous system, primary central nervous system lymphoma, non Hodgkin's lymphoma, spinal axis tumors, brain stem glioma, pituitary adenoma, adrenocortical cancer, gall bladder cancer, cancer of the spleen, cholangiocarcinoma, fibrosarcoma, neuroblastoma, retinoblastoma, or a combination of one or more of the above cancers in a patient, said methods comprising administering thereto therapeutically effective amounts of a compound having formula (II) and one additional therapeutic agent or more than one additional therapeutic agent.

Still another aspect comprises methods of treating mesothioloma, bladder cancer, pancreatic cancer, skin cancer, cancer of the head or neck, cutaneous or intraocular melanoma, ovarian cancer, breast cancer, uterine cancer, carcinoma of the fallopian tubes, carcinoma of the endometrium, carcinoma of the cervix, carcinoma of the vagina, carcinoma of the vulva, bone cancer, ovarian cancer, cervical cancer, colon cancer, rectal cancer, cancer of the anal region, stomach cancer, gastrointestinal (gastric, colorectal, and duodenal), chronic lymphocytic leukemia, esophageal cancer, cancer of the small intestine, cancer of the endocrine system, cancer of the thyroid gland, cancer of the parathyroid gland, cancer of the adrenal gland, sarcoma of soft tissue, cancer of the urethra, cancer of the penis, testicular cancer, hepatocellular cancer (hepatic and billiary duct), primary or secondary central nervous system tumor, primary or secondary brain tumor, Hodgkin's disease, chronic or acute leukemia, chronic myeloid leukemia, lymphocytic lymphomas, lymphoblastic leukemia, follicular lymphoma, lymphoid malignancies of T-cell or B-cell origin, melanoma, multiple myeloma, oral cancer, ovarian cancer, non-small cell lung cancer, prostate cancer, small cell lung cancer, cancer of the kidney and ureter, renal cell carcinoma, carcinoma of the renal pelvis, neoplasms of the central nervous system, primary central nervous system lymphoma, non Hodgkin's lymphoma, spinal axis tumors, brain stem glioma, pituitary adenoma, adrenocortical cancer, gall bladder cancer, cancer of the spleen, cholangiocarcinoma, fibrosarcoma, neuroblastoma, retinoblastoma, or a combination of one or more of the above cancers in a patient, said methods comprising administering thereto therapeutically effective amounts of a compound having formula (II) and one or more than one of etoposide, vincristine, CHOP, rituximab, rapamycin, R—CHOP, bortezomib, MLN8237, tozasertib (also known as VX-680 or MK-0457), PHA-739358, AT9283, AZD1152, BI811283, ENMD-2076, CYC116, AMG900, PF-03814735, R763, SNS-314 or TAK-901.

Still another aspect comprises methods of treating B-cell lymphoma in a patient comprising administering thereto a therapeutically effective amount of a compound having formula (II) and etoposide.

Still another aspect comprises methods of treating B-cell lymphoma in a patient comprising administering thereto therapeutically effective amounts of a compound having formula (II) and vincristine.

Still another aspect comprises methods of treating B-cell lymphoma in a patient comprising administering thereto therapeutically effective amounts of a compound having formula (II) and CHOP.

Still another aspect comprises methods of treating B-cell lymphoma in a patient comprising administering thereto therapeutically effective amounts of a compound having formula (II) and rituximab.

Still another aspect comprises methods of treating B-cell lymphoma in a patient comprising administering thereto therapeutically acceptable amounts of a compound having formula (II) and rapamycin.

Still another aspect comprises methods of treating mantle cell lymphoma in a patient comprising administering thereto therapeutically acceptable amounts of a compound having formula (II) and R—CHOP.

Still another aspect comprises methods of treating mantle cell lymphoma in a patient comprising administering thereto therapeutically effective amounts of a compound having formula (II) and bortezomib.

In still yet another aspect, the present disclosure relates to a method of treating a patient suffering from cancer. The method comprises the steps of:

a) administering to a patient suffering from cancer a therapeutically effective amount of at least one polyploidy inducing agent; and b) administering to the patient a therapeutically effective amount of at least one Bcl-2 family protein inhibitor.

In the above method, the polyploidy inducing agent can be an Aurora Kinase inhibitor. The Aurora Kinase inhibitor can be an Aurora Kinase A inhibitor, an Aurora Kinase B inhibitor, an Aurora Kinase C inhibitor or combinations thereof. More specifically, the Aurora Kinase inhibitor is an Aurora Kinase B inhibitor. For example, the Aurora Kinase B inhibitor is AZD1152, ZM447439, VX-680/MK0457 or Hersperadin.

In the above method, the Bcl-2 family protein inhibitor can be ABT-263, ABT-737, a Bcl-X$_L$ selective inhibitor or combinations thereof.

In another aspect, the present disclosure relates to a combination of therapeutic agents for use in treating a patient suffering from cancer. The combination comprises:

a) at least one polyploidy inducing agent for use in inducing polyploidization in one or more cancer cells in the patient; and b) at least one Bcl-2 family protein inhibitor.

In the above combination, the polyploidy inducing agent can be an Aurora Kinase inhibitor. The Aurora Kinase inhibitor can be an Aurora Kinase A inhibitor, an Aurora Kinase B inhibitor, an Aurora Kinase C inhibitor or combinations thereof. More specifically, the Aurora Kinase inhibitor is an Aurora Kinase B inhibitor. For example, the Aurora Kinase B inhibitor is AZD1152, ZM447439, VX-680/MK0457 or Hersperadin.

In the above combination, the Bcl-2 family protein inhibitor can be ABT-263, ABT-737, a Bcl-X$_L$ selective inhibitor or combinations thereof.

In yet another aspect, the present disclosure relates to a method of classifying a patient for eligibility for treatment with a polyploidy inducing agent, a Bcl-2 family protein inhibitor or a combination of a polyploidy inducing agent and a Bcl-2 family protein inhibitor. The method comprising the steps of:

a) providing a test sample from a patient;

b) determining the presence or absence of at least one mutation in at least one gene selected from the group consisting of: a BAX gene, a BAK gene or a NOXA gene in the test sample; and c) classifying the patient as being eligible for receiving treatment with a polyploidy inducing agent, a Bcl-2 family protein inhibitor or a combination of a polyploidy inducing agent and a Bcl-2 family protein inhibitor based on the presence or absence of at least one mutation as determined in step b).

In the above method, the polyploidy inducing agent can be an Aurora Kinase inhibitor. The Aurora Kinase inhibitor can be an Aurora Kinase A inhibitor, an Aurora Kinase B inhibitor, an Aurora Kinase C inhibitor or combinations thereof. More specifically, the Aurora Kinase inhibitor is an Aurora Kinase B inhibitor. For example, the Aurora Kinase B inhibitor is AZD1152, ZM447439, VX-680/MK0457 or Hersperadin.

In the above method, the Bcl-2 family protein inhibitor can be ABT-263, ABT-737, a Bcl-X$_L$ selective inhibitor or combinations thereof.

In the above method, the test sample can comprise a tissue sample. For example, the tissue sample comprises a peripheral blood sample, a tumor tissue or a suspected tumor tissue, a thin layer cytological sample, a fine needle aspirate sample, a bone marrow sample, a lymph node sample, a urine sample, an ascites sample, a lavage sample, an esophageal brushing sample, a bladder or lung wash sample, a spinal fluid sample, a brain fluid sample, a ductal aspirate sample, a nipple discharge sample, a pleural effusion sample, a fresh frozen tissue sample, a paraffin embedded tissue sample or an extract or processed sample produced from any of a peripheral blood sample, a tumor tissue or a suspected tumor tissue, a thin layer cytological sample, a fine needle aspirate sample, a bone marrow sample, a urine sample, an ascites sample, a lavage sample, an esophageal brushing sample, a bladder or lung wash sample, a spinal fluid sample, a brain fluid sample, a ductal aspirate sample, a nipple discharge sample, a pleural effusion sample, a fresh frozen tissue sample or a paraffin embedded tissue sample.

Moreover, in the above method, the determination step (b) can be performed by in situ hybridization. For example, the in situ hybridization can be performed with a nucleic acid probe that is fluorescently labeled. Alternatively, the in situ hybridization is performed with at least two nucleic acid probes. In still yet another alternative, the in situ hybridization is performed with a peptide nucleic acid probe.

Alternatively, in the above method, the determination step (b) can be performed by polymerase chain reaction.

In the above method, the patient may also, contemporaneously therewith, be receiving treatment with chemotherapy, radiation or combinations thereof.

In another aspect, the present disclosure relates to a method of monitoring a patient suffering from cancer and being treated with a polyploidy inducing agent, a Bcl-2 family protein inhibitor or a combination of a polyploidy inducing agent and a Bcl-2 family protein inhibitor. The method comprises the steps of:

a) providing a test sample from a patient suffering from cancer and currently being treated with at least one polyploidy inducing agent, a Bcl-2 family protein inhibitor or a combination of a polyploidy inducing agent and a Bcl-2 family protein inhibitor;

b) determining the presence or absence of at least one mutation in at least one gene selected from the group consisting of: a BAX gene, a BAK gene or a NOXA gene in the test sample; and c) determining whether the patient should continue to be treated with a polyploidy inducing agent, a Bcl-2 family protein inhibitor or a combination of a polyploidy inducing agent and a Bcl-2 family protein inhibitor based on the presence or absence of at least one mutation as determined in step b).

In the above method, the polyploidy inducing agent can be an Aurora Kinase inhibitor. The Aurora Kinase inhibitor can be an Aurora Kinase A inhibitor, an Aurora Kinase B inhibitor, an Aurora Kinase C inhibitor or combinations thereof. More specifically, the Aurora Kinase inhibitor is an Aurora Kinase B inhibitor. For example, the Aurora Kinase B inhibitor is AZD1152, ZM447439, VX-680/MK0457 or Hersperadin.

In the above method, the Bcl-2 family protein inhibitor can be ABT-263, ABT-737, a Bcl-X$_L$ selective inhibitor or combinations thereof.

In the above method, the test sample can comprise a tissue sample. For example, the tissue sample comprises a peripheral blood sample, a tumor tissue or a suspected tumor tissue, a thin layer cytological sample, a fine needle aspirate sample, a bone marrow sample, a lymph node sample, a urine sample, an ascites sample, a lavage sample, an esophageal brushing sample, a bladder or lung wash sample, a spinal fluid sample, a brain fluid sample, a ductal aspirate sample, a nipple discharge sample, a pleural effusion sample, a fresh frozen tissue sample, a paraffin embedded tissue sample or an extract or processed sample produced from any of a peripheral blood sample, a tumor tissue or a suspected tumor tissue, a thin layer cytological sample, a fine needle aspirate sample, a bone marrow sample, a urine sample, an ascites sample, a lavage sample, an esophageal brushing sample, a bladder or lung wash sample, a spinal fluid sample, a brain fluid sample, a ductal aspirate sample, a nipple discharge sample, a pleural effusion sample, a fresh frozen tissue sample or a paraffin embedded tissue sample.

Moreover, in the above method, the determination step (b) can be performed by in situ hybridization. For example, the in situ hybridization can be performed with a nucleic acid probe that is fluorescently labeled. Alternatively, the in situ hybridization is performed with at least two nucleic acid probes. In still yet another alternative, the in situ hybridization is performed with a peptide nucleic acid probe.

Alternatively, in the above method, the determination step (b) can be performed by polymerase chain reaction.

In the above method, the patient may also, contemporaneously therewith, be receiving treatment with chemotherapy, radiation or combinations thereof.

In still yet another aspect, the present disclosure relates to a method of classifying a patient as having a cancer that is resistant to treatment with a polyploidy inducing agent, a Bcl-2 family protein inhibitor or a combination of a polyploidy inducing agent and a Bcl-2 family protein inhibitor, the method comprising the steps of:

a) providing a test sample from a patient suffering from cancer;

b) determining the presence or absence of at least one mutation in at least one gene selected from the group consisting of: a BAX gene, a BAK gene or a NOXA gene in the test sample; and c) classifying the patient as having a cancer that is resistant to treatment with a polyploidy inducing agent, a Bcl-2 family protein inhibitor or a combination of a polyploidy inducing agent and a Bcl-2 family protein inhibitor based on the presence or absence of at least one mutation determined in step b).

In the above method, the polyploidy inducing agent can be an Aurora Kinase inhibitor. The Aurora Kinase inhibitor can be an Aurora Kinase A inhibitor, an Aurora Kinase B inhibitor, an Aurora Kinase C inhibitor or combinations thereof. More specifically, the Aurora Kinase inhibitor is an Aurora Kinase B inhibitor. For example, the Aurora Kinase B inhibitor is AZD1152, ZM447439, VX-680/MK0457 or Hersperadin.

In the above method, the Bcl-2 family protein inhibitor can be ABT-263, ABT-737, a Bcl-$X_L$ selective inhibitor or combinations thereof. In the above method, the test sample can comprise a tissue sample. For example, the tissue sample comprises a peripheral blood sample, a tumor tissue or a suspected tumor tissue, a thin layer cytological sample, a fine needle aspirate sample, a bone marrow sample, a lymph node sample, a urine sample, an ascites sample, a lavage sample, an esophageal brushing sample, a bladder or lung wash sample, a spinal fluid sample, a brain fluid sample, a ductal aspirate sample, a nipple discharge sample, a pleural effusion sample, a fresh frozen tissue sample, a paraffin embedded tissue sample or an extract or processed sample produced from any of a peripheral blood sample, a tumor tissue or a suspected tumor tissue, a thin layer cytological sample, a fine needle aspirate sample, a bone marrow sample, a urine sample, an ascites sample, a lavage sample, an esophageal brushing sample, a bladder or lung wash sample, a spinal fluid sample, a brain fluid sample, a ductal aspirate sample, a nipple discharge sample, a pleural effusion sample, a fresh frozen tissue sample or a paraffin embedded tissue sample.

Moreover, in the above method, the determination step (b) can be performed by in situ hybridization. For example, the in situ hybridization can be performed with a nucleic acid probe that is fluorescently labeled. Alternatively, the in situ hybridization is performed with at least two nucleic acid probes. In still yet another alternative, the in situ hybridization is performed with a peptide nucleic acid probe.

Alternatively, in the above method, the determination step (b) can be performed by polymerase chain reaction.

In the above method, the patient may also, contemporaneously therewith, be receiving treatment with chemotherapy, radiation or combinations thereof.

DETAILED DESCRIPTION

In one aspect, the present disclosure relates to the discovery of a synergistic effect that occurs in tumor and cancer cells when these cells are administered a therapeutically effective amount of at least one polyploidy inducing agent and a therapeutically effective amount of at least one Bcl-2 family protein inhibitor. Specifically, the inventors of the present disclosure discovered that the induction of polyploidization in certain tumor and cancer cells makes or renders the survival of these resulting polyploidy cells dependent on the anti-apoptotic activity of Bcl-$X_L$. More specifically, inducing polyploidy in these tumor and cancer cells sensitizes these cells to Bcl-$X_L$ inhibition. Thus, the inventors have discovered a polyploidy-mediated method for inducing apoptosis or cell death in these cells. This method involves administering to a patient suffering from cancer a combination of therapeutic agents. Specifically, the patient is administered at least one polyploidy inducing agent. The purpose of the polyploidy inducing agent is to induce polyploidy in one or more cancer cells. As mentioned previously herein, after induction of polyploidy, the survival of these polyploid tumor and cancer cells is dependent on Bcl-$X_L$. Apoptosis or death of these polyploidy tumor and cancer cells can be obtained or achieved by administering to the patient at least one Bcl-2 family protein inhibitor. The order in which the at least one polyploidy inducing agent and the at least one Bcl-2 family protein inhibitor are administered is not critical. However, because tumor and cancer cells do not become sensitized to Bcl-2 family protein inhibitors until after the induction of polyploidy, it is preferred to administer the at least one polyploidy inducing agent to the patient prior to or along with the at least one Bcl-2 family protein inhibitor. In connection with the above discovery, the inventors of the present disclosure also discovered that tumor and cancer cells (regardless of whether or not these cells are induced to be polyploid or not) which contain at least one mutation in (i) a human Bcl-2 pro-apoptotic encoding gene (such as a human BAX gene and a human BAK gene), (ii) a human NOXA gene, or (iii) a human Bcl-2 pro-apoptotic encoding gene (such as a human BAX gene and a human BAK gene) and a human NOXA gene are immune or exhibit resistance to treatment with a Bcl-2 family protein inhibitor after induction of polyploidy (such as with at least one polyploidy inducing agent). In other words, polyploid tumor and cancer cells which contain at least one mutation in (i) a human Bcl-2 pro-apoptotic encoding gene (such as a human BAX gene and a human BAK gene), (ii) a human NOXA gene, or (iii) a human Bcl-2 pro-apoptotic encoding gene (such as a human BAX gene and a human BAK gene) and human NOXA gene do not exhibit or experience apoptosis or cell death when simultaneously or subsequently treated with at least one Bcl-2 family protein inhibitor.

Thus, in view of this further discovery, in another aspect, the present disclosure also provides methods and compositions for monitoring cancer and tumor cells for resistance to polyploidy inducing agent (such as an Aurora Kinase inhibitor) therapy, Bcl-2 family protein inhibitor therapy or a combination of polyploidy inducing agent and Bcl-2 family protein inhibitor therapy. The disclosure provides diagnostic assays for identifying, classifying and monitoring cancer patients which comprises assessing a test sample for the presence or absence of at least one mutation in (i) a human Bcl-2 pro-apoptotic encoding gene (such as a human BAX gene and a human BAK gene), (ii) a human NOXA gene, or (iii) a human Bcl-2 pro-apoptotic encoding gene (such as a human BAX gene and a human BAK gene) and a human NOXA gene. The inventive assays include assay methods for identifying patients eligible to receive a polyploidy inducing agent, Bcl-2 family protein inhibitor therapy or a polyploidy inducing agent and Bcl-2 family protein inhibitor therapy (as a combination therapy together or together with yet another therapy (e.g., such as with chemotherapy, radiation or combinations thereof) and for monitoring patient response to such therapy. The disclosure comprises, for example, determining by fluorescent in situ hybridization the presence or absence of at least one mutation in (i) a human Bcl-2 pro-apoptotic encoding gene (such as a human BAX gene and a human BAK gene), (ii) a human NOXA gene, or (iii) a human Bcl-2 pro-apoptotic encoding gene (such as a human BAX gene and a human BAK gene) and a human NOXA gene. The methods herein can be performed prior to the induction of polyploidy or after the induction of polyploidy. Patients classified as having one or mutations or an increase in one or more mutations over a baseline (or predetermined) level in (i) a human Bcl-2 pro-apoptotic encoding gene (such as a human BAX gene and a human BAK gene), (ii) a human NOXA gene, or (iii) a human Bcl-2 pro-apoptotic encoding gene (such as a human BAX gene and a human BAK gene) and a human NOXA gene would be considered to be ineligible to receive at least one polyploidy inducing agent, at least one Bcl-2 family protein inhibitor or the combination therapy of a polyploidy inducing agent and Bcl-2 family protein inhibitor therapy because such patients would be considered to be less likely to respond to each of these therapies. Specifically, patients who are identified as having one or more mutations in (i) a human Bcl-2 pro-apoptotic encoding gene (such as a human BAX gene and a human BAK gene), (ii) a human NOXA gene, or (iii) a human Bcl-2 pro-apoptotic encoding gene (such as a human BAX gene and a human BAK gene) and a human NOXA gene are believed to be immune, resistant or less sensitized to treatment with at least one Bcl-2 family protein inhibitor before treatment with or after treatment with at least one polyploidy inducing agent (to induce polyploidization).

In one aspect, the disclosure comprises a method for identifying or classifying a patient as eligible for treatment with a polyploidy inducing agent, a Bcl-2 family protein inhibitor or with a polyploidy inducing agent and a Bcl-2 family protein inhibitor (either together or in combination with a third therapy). The method comprising the steps of:

(a) providing a tissue sample from a patient;

(b) determining the presence or absence of at least one mutation in (i) a human Bcl-2 pro-apoptotic encoding gene (such as a human BAX gene and a human BAK gene), (ii) a human NOXA gene, or (iii) a human Bcl-2 pro-apoptotic encoding gene (such as a human BAX gene and a human BAK gene) and a human NOXA gene; and (c) classifying the patient as being eligible for treatment with a polyploidy inducing agent, a Bcl-2 family protein inhibitor or both a polyploidy inducing agent and Bcl-2 family protein inhibitor based on the presence or absence of at least one mutation in a (i) a human Bcl-2 pro-apoptotic encoding gene (such as a human BAX gene and a human BAK gene), (ii) a human NOXA gene, or (iii) a human Bcl-2 pro-apoptotic encoding gene (such as a human BAX gene and a human BAK gene) and a human NOXA gene. In the above method, a patient would be ineligible for treatment with a polyploidy inducing agent, a Bcl-2 family protein inhibitor or both a polyploidy inducing agent and a Bcl-2 family protein inhibitor based on the presence of at least one mutation or an increase in the number of one or more mutations over a baseline (or predetermined) level in a (i) a human Bcl-2 pro-apoptotic encoding gene (such as a human BAX gene and a human BAK gene), (ii) a human NOXA gene, or (iii) a human Bcl-2 pro-apoptotic encoding gene (such as a human BAX gene and a human BAK gene) and a human NOXA gene. As with the methods mentioned previously herein, this method can be performed before or after induction of polyploidy in the patient.

In this aspect, the cancer can be any type of cancer, such as colorectal carcinoma or pancreatic cancer. Moreover, in this aspect, the gene amplification can be determined by a multi-color fluorescent in situ hybridization (FISH) assay, for example, performed on a lung cancer tumor biopsy sample. In other aspects, the quantitative polymerase chain reaction (Q-PCR) method is used.

In yet another aspect, the disclosure comprises a method for identifying or classifying a patient having a cancer that is resistant to therapy with a polyploidy inducing agent, a Bcl-2 family protein inhibitor, or a combination of a polyploidy inducing agent and a Bcl-2 family protein inhibitor, the method comprising the steps of:

(a) providing a test sample (e.g., such as a tissue sample) from a patient;

(b) determining the presence or absence of at least one mutation in a (i) a human Bcl-2 pro-apoptotic encoding gene (such as a human BAX gene and a human BAK gene), (ii) a human NOXA gene, or (iii) a human Bcl-2 pro-apoptotic encoding gene (such as a human BAX gene and a human BAK gene) and a human NOXA gene; and (c) classifying the patient as having a cancer that is resistant to a polyploidy inducing agent, a Bcl-2 family protein inhibitor or a combination of a polyploidy inducing agent and a Bcl-2 family protein inhibitor based on the presence of at least one mutation in a (i) a human Bcl-2 pro-apoptotic encoding gene (such as a human BAX gene and a human BAK gene), (ii) a human NOXA gene, or (iii) a human Bcl-2 pro-apoptotic encoding gene (such as a human BAX gene and a human BAK gene) and a human NOXA gene. As with the methods mentioned previously herein, this method can be performed before or after induction of polyploidy in the patient.

In this aspect, the cancer can be any type of cancer, such as colorectal carcinoma or pancreatic cancer. Moreover, in this aspect, the gene amplification can be determined by a multi-color fluorescent in situ hybridization (FISH) assay, for example, performed on a lung cancer tumor biopsy sample. In other aspects, the polymerase chain reaction (PCR) is used.

In still yet another aspect, the disclosure is directed to methods for monitoring a patient being treated with a polyploidy inducing agent, a Bcl-2 family protein inhibitor or a combination of a polyploidy inducing agent and a Bcl-2 family protein inhibitor, the method comprising the steps of:

(a) providing a test sample from a cancer patient being treated with at least one polyploidy inducing agent, a Bcl-2 family protein inhibitor or a combination of a polyploidy inducing agent and a Bcl-2 family protein inhibitor (optionally, tumor or cancer cells obtained from a tissue sample can be identified or extracted);

(b) determining in the test sample (for example, in the tumor or cancer cells) the presence or absence of at least one mutation in (i) a human Bcl-2 pro-apoptotic encoding gene (such as a human BAX gene and a human BAK gene), (ii) a human NOXA gene, or (iii) a human Bcl-2 pro-apoptotic encoding gene (such as a human BAX gene and a human BAK gene) and a human NOXA gene; and (c) comparing the number of mutations in (i) a human Bcl-2 pro-apoptotic encoding gene (such as a human BAX gene and a human BAK gene), (ii) a human NOXA gene, or (iii) a human Bcl-2 pro-apoptotic encoding gene (such as a human BAX gene and a human BAK gene) and a human NOXA gene from the test sample (such as in the tumor or cancer cells) against a baseline level or a predetermined level; and (d) determining whether the patient should continue to be treated with the polyploidy inducing agent, Bcl-2 family protein inhibitor or a combination of a polyploidy inducing agent and Bcl-2 family protein inhibitor based on the comparison in step (c). As with the methods mentioned previously herein, this method can be performed before or after induction of polyploidy in the patient.

The comparison (or informational analysis) of the number of one or more mutations determined from the test sample with the baseline or predetermined level can be done by an automated system, such as a software program or intelligence system that is part of, or compatible with, the equipment (e.g., computer platform) on which the assay is carried out. Alternatively, this comparison or informational analysis can be done by a physician.

Specifically, if the test sample (e.g., the tumor or cancer cells) having at least one mutation in (i) a human Bcl-2 pro-apoptotic encoding gene (such as a human BAX gene and a human BAK gene), (ii) a human NOXA gene, or (iii) a human Bcl-2 pro-apoptotic encoding gene (such as a human BAX gene and a human BAK gene) and a human NOXA gene is the same as or higher then the baseline level or predetermined level, then treatment with the polyploidy inducing agent, Bcl-2 family protein inhibitor or combination of a polyploidy inducing agent and a Bcl-2 family protein inhibitor can be discontinued, stopped or terminated. Alternatively, the treating physician may decide to combine the polyploidy inducing agent with at least a second therapy (for example, treatment with a second small molecule) as a combination therapy. Still further alternatively, the treating physician may decide to combine the Bcl-2 family protein inhibitor with at least a second therapy (for example, treatment with a second small molecule) as a combination therapy. However, if at least one mutation in (i) a human Bcl-2 pro-apoptotic encoding gene (such as a human BAX gene and a human BAK gene), (ii) a human NOXA gene, or (iii) a human Bcl-2 pro-apoptotic encoding gene (such as a human BAX gene and a human BAK gene) and a human NOXA gene is less then the baseline level or the predetermined level or if no mutations are detected in (i) a human Bcl-2 pro-apoptotic encoding gene (such as a human BAX gene and a human BAK gene), (ii) a human NOXA gene, or (iii) a human Bcl-2 pro-apoptotic encoding gene (such as a human BAX gene and a human BAK gene) and a human NOXA gene then treatment with the polyploidy inducing agent, a Bcl-2 family protein inhibitor or a combination of a polyploidy inducing agent and a Bcl-2 family protein inhibitor can be continued. Again, depending on the results obtained with said treatment, the treating physician may decide to combine the polyploidy inducing agent with at least a second therapy (for example, treatment with a second small molecule) as a combination therapy. Alternatively, depending on the results obtained with said treatment, the treating physician may decide to combine the Bcl-2 family protein inhibitor therapy with at least a second therapy (for example, treatment with a second small molecule).

Again, FISH and PCR methods can be used to detect the presence or absence of at least one mutation in (i) a human Bcl-2 pro-apoptotic encoding gene (such as a human BAX gene and a human BAK gene), (ii) a human NOXA gene, or (iii) a human Bcl-2 pro-apoptotic encoding gene (such as a human BAX gene and a human BAK gene) and a human NOXA gene in a test sample obtained from a patient.

The disclosure is also directed to kits that package, for example, oligo- or polynucleotides engineered to be used as PCR primers, FISH probes, etc.

The disclosure has significant capability to provide improved stratification of patients for cancer therapy, and in particular for polyploidy inducing agent therapy, Bcl-2 family protein inhibitor therapy or a combination of polyploidy inducing agent therapy and Bcl-2 family protein inhibitor therapy. The assessment of these biomarkers according to the present disclosure also allows tracking of individual patient response to the therapy.

A. Definitions

Section headings as used in this section and the entire disclosure herein are not intended to be limiting.

As used herein, the singular forms "a," "an" and "the" include plural referents unless the context clearly dictates otherwise. For the recitation of numeric ranges herein, each intervening number there between with the same degree of precision is explicitly contemplated. For example, for the range 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9 and 7.0 are explicitly contemplated.

a) Antitumorigenesis

As used herein, the term "antitumorigenesis," refers to a reduction of tumor growth.

b) Aurora Kinase Inhibitor

An "Aurora Kinase inhibitor" refers to a therapeutic compound of any type (e.g., non-selective or selective), including small molecule, antibody, antisense, small interfering RNA, or microRNA-based compounds, that binds to at least one of Aurora Kinase A, Aurora A, Aurora Kinase B, Aurora B, Aurora Kinase C or Aurora C, and antagonizes the activity of at least one Aurora Kinase A, Aurora A, Aurora Kinase B, Aurora B, Aurora Kinase C or Aurora C related nucleic acid or protein.

c) Aurora Kinase A Inhibitor

An "Aurora Kinase A inhibitor" refers to a therapeutic compound of any type (e.g., non-selective or selective), including small molecule, antibody, antisense, small interfering RNA, or microRNA-based compounds, that binds to at least one of Aurora Kinase A or Aurora A, and antagonizes the activity of the Aurora Kinase A or Aurora A related nucleic acid or protein. The methods of the present disclosure are useful with any known or hereafter developed Aurora Kinase A inhibitor. Examples of an Aurora Kinase A inhibitor are PHA-739358, MLN-8054, R-763, JNJ-7706621, MP-529 and MP-235.

d) Aurora Kinase B Inhibitor

An "Aurora Kinase B inhibitor" refers to a therapeutic compound of any type (e.g., non-selective or selective), including small molecule, antibody, antisense, small interfering RNA, or microRNA-based compounds, that binds to at least one of Aurora Kinase B or Aurora B, and antagonizes the activity of the Aurora Kinase B or Aurora B related nucleic acid or protein. For example, a number of Aurora Kinase B inhibitors are known to inhibit at least one of histone H3 phosphorylation or cell division. In addition, a number of Aurora Kinase B inhibitors are known to induce apoptosis in at least one cell system (such as an acute myeloid leukemia cell line, a primary acute myeloid leukemia culture, etc.). The methods of the present disclosure are useful with any known or hereafter developed Aurora Kinase B inhibitor. Examples of an Aurora Kinase B inhibitor are AZD1152, ZM447439, VX-680/MK0457 and Hesperadin.

AZD1152, also known as, 2-[[3-({4-[(5-{2-[(3-Fluorophenyl)amino]-2-oxoethyl}-1H-pyrazol-3-yl)amino]-quinazolin-7-yl}oxy)propyl](ethyl)amino]ethyl dihydrogen phosphate, is a prodrug of a pyrazoloquinazoline Aurora Kinase inhibitor (AZD1152-hydroxyquinazoline pyrazol anilide (HQPA)) and is converted rapidly to the active AZD1152-HQPA in plasma (See, Mortlock, A A, et al., *J. Med. Chem.*, 50:2213-24 (2007)). AZD1152-HQPA is a highly potent and selective inhibitor of Aurora B.

ZM447439, also known as 4-(4-(N-benzoylamino) anilino)-6-methoxy-7-(3-(1-morpholino)propoxy)quinazoline, is a quinazoline derivative, inhibits Aurora A and Aurora B. The chemical structure of ZM447439 is provided in Ditchfield, C., et al., *J. Cell Bio.*, 161(2):267-280 (2003) and Montembault, E., et al., *Drugs of the Future*, 30(1):1-9 (2005).

VX-680/MK0457 is a cyclopropane carboxylic acid of {4-[4-(4-methyl-piperazin-1-yl)-6-(5-methyl-2H-pyrazol-3-ylamino)-pyrimidin-2-ylsulphanyl]-phenyl}-amide and inhibits Aurora A, Aurora B and Aurora C. The chemical structure of VX-680/MK0457 is provided in Montembault, E., et al., *Drugs of the Future*, 30(1):1-9 (2005).

Hesperadin, an indolinone, inhibits Aurora B. The chemical structure of Hesperadin is provided in Hauf, S., et al., *J. Cell Bio.*, 161(2):281-294 (2003) and Montembault, E., et al., *Drugs of the Future*, 30(1):1-9 (2005).

e) Aurora Kinase C Inhibitor

An "Aurora Kinase C inhibitor" refers to a therapeutic compound of any type (e.g., non-selective or selective), including small molecule, antibody, antisense, small interfering RNA, or microRNA-based compounds, that binds to at least one of Aurora Kinase C or Aurora C, and antagonizes the activity of the Aurora Kinase C or Aurora C related nucleic acid or protein. The methods of the present disclosure are useful with any known or hereafter developed Aurora Kinase C inhibitor. Examples of an Aurora Kinase C inhibitor are AZD1152 and VX-680/MK-0457.

f) Consisting Essentially of a Polynucleotide Having a % Sequence Identity

"Consisting essentially of a polynucleotide having a % sequence identity" means that the polynucleotide does not substantially differ in length, but may differ substantially in sequence. Thus, a polynucleotide "A" consisting essentially of a polynucleotide having at least 80% sequence identity to a known sequence "B" of 100 nucleotides means that polynucleotide "A" is about 100 nucleotides (nts) long, but up to 20 nts can vary from the "B" sequence. The polynucleotide sequence in question can be longer or shorter due to modification of the termini, such as, for example, the addition of 1-15 nucleotides to produce specific types of probes, primers and other molecular tools, etc., such as the case of when substantially non-identical sequences are added to create intended secondary structures. Such non-identical nucleotides are not considered in the calculation of sequence identity when the sequence is modified by "consisting essentially of."

g) Bcl-2

As used herein, the term "Bcl-2" refers to a family of pro- and anti-apoptotic proteins that constitute a critical control point for apoptosis. Members of this family include both pro- and anti-apoptotic proteins and share homology in up to four conserved regions termed Bcl-2 homology (BH) 1-4 domains. The family can be divided into three main subclasses: anti-apoptotic proteins, pro-apoptotic proteins, "BH3-only" proteins.

The anti-apoptotic proteins, which include Bcl-2 and Bcl-$X_L$, are all "multidomain," sharing homology throughout all four BH domains. However, the pro-apoptotic proteins can be further subdivided and include multidomain proteins, such as BAX and BAK, which possess sequence homology in BH1-3 domains. The more distantly related "BH3-only" proteins are to date all pro-apoptotic and share sequence homology within the amphipathic α-helical BH3 region, which is required for their apoptotic function.

The human BAK gene encoding human BAK has Accession no. U23765, and is described in Chittenden et al. *Nature* 374:733-736 (1995). The human BAK-2 gene has Accession no. U16812, and is described in Kiefer et al., *Nature* 374:736-739 (1995). The human BAX genes encoding human BAX have Accession nos. L22475, L22474 and L22473, and are described in Oltvai et al., *Cell* 74:609-619 (1993).

As used herein, the phrase "human Bcl-2 pro-apoptotic encoding gene" refers to a gene that encodes at least one human Bcl-2 pro-apoptotic protein or fragment thereof such as, for example, human BAK or human BAX.

The "BH3-only proteins" constitute the third subset of the Bcl-2 family and include, for example, BID, NOXA, PUMA, BIK, BIM and BAD. These proteins share sequence homology only in the amphipathic-helical BH3 region which mutation analysis indicated is required in pro-apoptotic members for their death activity.

The human BID gene encoding human BID has Accession no. NM_197966, NM_197967, NM_001196 and is described in Genbank. The human NOXA gene encoding human NOXA has Accession no. NM_021127 and is described in Genbank. The human PUMA gene encoding human PUMA has Accession no. NM_001127242, NM_001127241, NM_001127240, NM_014417 and is described in Genbank. The human BIK gene encoding human BIK has Accession no. NM_001197 and is described in Genbank. The human BIM gene encoding human BIM has Accession no. NM_138621, NM_207002, NM_006538, BC033694, AY305714, AY305716, AY423443, AY423442, AY423441 and is described in Genbank. The human BAD gene encoding human BAD has Accession no. NM_032989, NM_004322, BC095431 and is described in Genbank.

As used herein, the phrase, "human BH3 encoding gene" refers to a gene that encodes at least one human Bcl-2 BH3-only protein or fragment thereof, such as, for example, human BID, human NOXA, human PUMA, human BIK, human BIM and human BAD.

h) Bcl-2 Family Protein Inhibitor, Bcl-2 Family Inhibitor or Inhibitor of a Bcl-2 Family Protein As used herein, the phrases "Bcl-2 Family Protein Inhibitor", "Bcl-2 Family Inhibitor" or "Inhibitor of a Bcl-2 Family Protein" as used interchangeably herein, refer to a therapeutic compound of any type (e.g., non-selective or selective), including small molecule-, antibody-, antisense-, small interfering RNA, or microRNA-based compounds, that binds and antagonizes or inhibits the activity of at least one gene or protein of the Bcl-2 family that governs mitochondrial outer membrane permeabilization (MOMP) and is anti-apoptotic (such as Bcl-2, Bcl-$X_L$, Bcl-w, Bcl-B, BFL-1 and MCl-1). Examples of Bcl-2 family protein inhibitors include the compounds described in Section B herein (namely, ABT-263 (which is N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl) amino)-3-((trifluoromethyl)sulfonyl)benzenesulfonamide)), ABT-737 (N-(4-(4-((4'-chloro(1,1'-biphenyl)-2-yl)methyl) piperazin-1-yl)benzoyl)-4-(((1R)-3-(dimethylamino)-1-((phenylsulfanyl)methyl)propyl)amino)-3-nitrobenzenesulfonamide, described in published US Patent Application Nos. 20050159427 and 20060128706, Bcl-$X_L$ inhibitors \ and combinations thereof.

i) Bcl-$X_L$ Selective Inhibitor(s)

As used herein, the phrase "Bcl-$X_L$ selective inhibitor(s)", refers to a Bcl-$X_L$ inhibitor that exhibits a selectivity for Bcl-$X_L$ over Bcl-2. Methods for determining whether a Bcl-$X_L$ inhibitor is a Bcl-$X_L$ selective inhibitor are well known in the art. Specifically, such methods involve determining the inhibition constants (Ki) for the Bcl-$X_L$ inhibitor compounds and the binding selectivity ratio (for example, Bcl-$X_L$ $K_i$:Bcl-2 $K_i$). The inhibition constant (Ki) is the dissociation constant of an enzyme-inhibitor complex or a protein/small molecule complex, wherein the small molecule is inhibiting binding of one protein to another protein or peptide. Inhibition constants can be determined using Time Resolved-Fluorescence Resonance Energy Transfer (TR-FRET) assay. Where the $K_i$ for a compound is represented as ">" (greater than) a certain numerical value, it is intended to mean that the binding affinity value (e.g., for Bcl-$X_L$) is greater than that determined in the assay. Where the binding selectivity ratio for a compound is represented as ">" (greater than) a certain numerical value, it is intended to mean that the selectivity of a particular compound for Bcl-XL over Bcl-2 is at least as great as the number indicated. Where the $K_i$ for a compound is represented as "<" (less than) a certain numerical value, it is intended to mean that the binding affinity value (e.g., for Bcl-2) is lower than the limit of detection of the assay used. Inhibition constants were determined using Wang's equation (Wang Zx., An Exact Mathematical Expression For Describing Competitive Binding Of Two Different Ligands To A Protein Molecule. *FEBS Lett.* 1995, 360:111-4).

j) Expression, Antisense Inhibition and Co-Suppression

"Expression" refers to the production of a functional end-product. Expression of a gene involves transcription of the gene and translation of the mRNA into a precursor or mature protein. "Antisense inhibition" refers to the production of antisense RNA transcripts capable of suppressing the expression of the target protein. "Co-suppression" refers to the production of sense RNA transcripts capable of suppressing the expression of identical or substantially similar foreign or endogenous genes (U.S. Pat. No. 5,231,020).

k) Isolated

As used herein, the term "isolated" in the context of nucleic acid molecules or polynucleotides refers to a nucleic acid molecule or polynucleotide which is separated from other nucleic acid molecules or polynucleotides which are present in the natural source of the nucleic acid molecule or polynucleotide. Moreover, an "isolated" nucleic acid molecule or polynucleotide, such as a cDNA molecule, can be substantially free of other cellular material, or culture medium when produced by recombinant techniques, or substantially free of chemical precursors or other chemicals when chemically synthesized. In one aspect, nucleic acid molecules or polynucleotides are isolated.

l) Gene

"Gene" refers to a nucleic acid fragment that expresses a specific protein, including regulatory sequences preceding (5' non-coding sequences) and following (3' non-coding sequences) the coding sequence.

m) Inhibition Constant or Ki

As used herein, "inhibition constant" or "Ki" refers the dissociation constant of an enzyme-inhibitor complex or a protein/small molecule complex, wherein the small molecule is inhibiting binding of one protein to another protein. A large Ki value indicates a low binding affinity, and a small Ki value indicates a high binding affinity. Ki can be determined using any method known in the art, such as by using Wang's equation (Wang Z X., An Exact Mathematical Expression For Describing Competitive Binding Of Two Different Ligands To A Protein Molecule. *FEBS Lett.* 1995; 360:111-4). A typical measure of binding affinity of an anti-apoptotic protein inhibitor is the balance between the binding and dissociation processes between the protein and the inhibitor (Ki).

n) Native Gene and Chimeric Construct

"Native gene" refers to a gene as found in nature with its own regulatory sequences. In contrast, "chimeric construct" refers to a combination of nucleic acid fragments that are not normally found together in nature. Accordingly, a chimeric construct may comprise regulatory sequences and coding sequences that are derived from different sources, or regulatory sequences and coding sequences derived from the same source, but arranged in a manner different than that normally found in nature.

o) Percent (%) Nucleic Acid Sequence Identity

"Percent (%) nucleic acid sequence identity" with respect to nucleic acid sequences is defined as the percentage of nucleotides in a candidate sequence that are identical with the nucleotides in the sequence of interest, after aligning the sequences and introducing gaps, if necessary, to achieve the maximum percent sequence identity. Alignment for purposes of determining % nucleic acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared.

When nucleotide sequences are aligned, the % nucleic acid sequence identity of a given nucleic acid sequence C to, with, or against a given nucleic acid sequence D (which can alternatively be phrased as a given nucleic acid sequence C that has or comprises a certain % nucleic acid sequence identity to, with, or against a given nucleic acid sequence D) can be calculated as follows:

% nucleic acid sequence identity=$W/Z*100$ where

W is the number of nucleotides scored as identical matches by the sequence alignment program's or algorithm's alignment of C and D and Z is the total number of nucleotides in D.

When the length of nucleic acid sequence C is not equal to the length of nucleic acid sequence D, the % nucleic acid sequence identity of C to D will not equal the % nucleic acid sequence identity of D to C.

p) Polymerase Chain Reaction or PCR

"Polymerase Chain Reaction" or "PCR", a technique for the synthesis of large quantities of specific DNA segments, consists of a series of repetitive cycles (Perkin Elmer Cetus Instruments, Norwalk, Conn.). Typically, the double stranded DNA is heat-denatured, the two primers complementary to the 3' boundaries of the target segment are annealed at low temperature and then extended at an intermediate temperature. One set of these three consecutive steps is referred to as a cycle.

PCR is a powerful technique used to amplify DNA millions of fold, by repeated replication of a template, in a short period of time. ((Mullis, K., et al., *Cold Spring Harb Symp Quant Biol.* 51 Pt 1:263-73 (1986)); European Patent Application No. 50,424; European Patent Application No. 84,796; European Patent Application No. 258,017, European Patent Application No. 237,362; European Patent Application No. 201,184, U.S. Pat. No. 4,683,202; U.S. Pat. No. 4,582,788; and U.S. Pat. No. 4,683,194). The process uses sets of specific in vitro synthesized oligonucleotides to prime DNA synthesis. The design of the primers is dependent upon the sequences of DNA that are to be analyzed. The technique is carried out through many cycles (usually 20-50) of melting the template at high temperature, allowing the primers to anneal to complementary sequences within the template and then replicating the template with DNA polymerase.

The products of PCR reactions can be analyzed by separation in agarose gels followed by ethidium bromide staining and visualization with UV transillumination. Alternatively, radioactive dNTPs can be added to the PCR in order to incorporate label into the products. In this case the products of PCR are visualized by exposure of the gel to x-ray film. The added advantage of radiolabeling PCR products is that the levels of individual amplification products can be quantitated.

q) Polynucleotide

A "polynucleotide" is a nucleic acid polymer of ribonucleic acid (RNA), deoxyribonucleic acid (DNA), modified RNA or DNA, or RNA or DNA mimetics (such as PNAs), and derivatives thereof, and homologues thereof. Thus, polynucleotides include polymers composed of naturally occurring nucleic bases, sugars and covalent inter-nucleoside (backbone) linkages as well as polymers having non-naturally-occurring portions that function similarly. Such modified or substituted nucleic acid polymers are well known in the art and are referred to as "analogues." Oligonucleotides are generally short polynucleotides from about 10 to up to about 160 or 200 nucleotides.

Polynucleotides also comprise primers that specifically hybridize to target sequences, including analogues and/or derivatives of the nucleic acid sequences, and homologues thereof.

Polynucleotides can be prepared by conventional techniques, such as solid-phase synthesis using commercially available equipment, such as that available from Applied Biosystems USA Inc. (Foster City, Calif.; USA), DuPont, (Wilmington, Del.; USA), or Milligen (Bedford, Mass.; USA). Modified polynucleotides, such as phosphorothioates and alkylated derivatives, can also be readily prepared by similar methods known in the art (See, U.S. Pat. Nos. 4,948,882, 5,464,746, and 5,424,414).

r) Polynucleotide Analogues

As used herein, the term "polynucleotide analogues" refers to polymers having modified backbones or non-natural internucleoside linkages. Modified backbones include those retaining a phosphorus atom in the backbone, such as phosphorothioates, chiral phosphorothioates, phosphorodithioates, phosphotriesters, aminoalkylphosphotriesters, methyl and other alkyl phosphonates, as well as those no longer having a phosphorus atom, such as backbones formed by short chain alkyl or cycloalkyl inter-nucleoside linkages, mixed heteroatom and alkyl or cycloalkyl inter-nucleoside linkages, or one or more short chain heteroatomic or heterocyclic inter-nucleoside linkages. Modified nucleic acid polymers (analogues) can contain one or more modified sugar moieties.

Analogs that are RNA or DNA mimetics, in which both the sugar and the inter-nucleoside linkage of the nucleotide units are replaced with novel groups, are also useful. In these mimetics, the base units are maintained for hybridization with the target sequence. An example of such a mimetic, which has been shown to have excellent hybridization properties, is a peptide nucleic acid (PNA) (See, Buchardt, O., P. Nielsen, and R. Berg. 1992. *Peptide Nucleic Acids*).

s) Polyploidy Inducing Agent

As used herein, the phrase "polyploidy inducing agent" refers to a therapeutic compound of any type (e.g., non-selective or selective), including small molecule, antibody, antisense, small interfering RNA, or microRNA-based compounds, that induce polyploidy in one or more cells. Methods for determining the induction or evidence of polyploidy in one or more cells can be obtained using routine techniques known in the art. For example, evidence of polyploidy can be determined by detecting elevated expression of p53. p53 is a surrogate for polyploidization in cells harboring wildtype p53 (See, Gizatullin, F. et al., "The Aurora Kinase inhibitor VX-680 induces endoreduplication and apoptosis preferentially in cells with compromised p53-dependent postmitotic checkpoint function," *Cancer Res.* 66, 7668-77. (2006)). Additionally, cells in which polyploidy has been induced exhibit a gross morphological increase in cell size and multinucleation, both of which can be detected using routine techniques known in the art.

Examples of polyploidy inducing agents, include, but are not limited to, Aurora Kinase inhibitors, microtubule inhibitors (such as, for example, Taxotere, vincristine, nocodazole, paclitaxel or colcemid), pan-kinase inhibitors (such as, for example, staurosporine), oncolytic viruses (such as, for example, ONYX-015), Acridine orange, Dolastain-10, Noscapine, topoisomerase II inhibitors (such as, for example, ICRF-187 or ICRF-193), 2-{4-[(7-chloro-2-quinoxalinyl)oxy]phenoxy}propionic acid, 2-{4-[(7-bromo-2-quinolinyl)oxy]phenoxy}propionic acid, Platycodin D, microtubule poisons (such as, for example, JG-03-14), actin polymerization inhibitors (such as, for example, Cytochalasin B), Bistramide A or antitumor antibiotics (such as, for example, Mithramycin SKI).

t) Predetermined Level

As used herein, the term "predetermined level" refers generally to an assay cut-off value that is used to assess diagnostic results by comparing the assay results against the predetermined level, and where the predetermined level already has been linked or associated with various clinical parameters (e.g., assessing risk, severity of disease, progression/non-progression/improvement, determining the age of a test sample, determining whether a test sample (e.g., serum or plasma) has hemolyzed, etc.). An example of a predetermined level that can be used is a baseline level obtained from one or more subjects that may optionally be suffering from one or more diseases or conditions. It is well known that cutoff values may vary dependent on the nature of the assay. It further is well within the ordinary skill in the art to adapt the disclosure herein for other assays to obtain assay-specific cut-off values for those other assays based on this description.

u) Primer or Probe

A "probe" or "primer" as used herein is a polynucleotide that is at least 8 nucleotides in length and forms a hybrid structure with a target sequence, due to complementarity of at least one sequence in the probe or primer with a sequence in the target region. The polynucleotide regions of the probe can be composed of DNA and/or RNA and/or synthetic nucleotide analogs. Preferably, the probe does not contain a sequence that is complementary to the sequence or sequences used to prime for a target sequence during the polymerase chain reaction.

v) Recombinant

"Recombinant" refers to an artificial combination of two otherwise separated segments of sequence, e.g., by chemical synthesis or by the manipulation of isolated segments of nucleic acids by genetic engineering techniques.

w) Specifically Hybridize

"Specifically hybridize" refers to the ability of a nucleic acid to bind detectably and specifically to a second nucleic acid. Polynucleotides specifically hybridize with target nucleic acid strands under hybridization and wash conditions that minimize appreciable amounts of detectable binding by non-specific nucleic acids.

x) Stringency or Stringent Conditions

The specificity of single stranded DNA to hybridize complementary fragments is determined by the stringency of the reaction conditions. Hybridization stringency increases as the propensity to form DNA duplexes decreases. In nucleic acid hybridization reactions, the stringency can be chosen to favor specific hybridizations (high stringency). Less-specific hybridizations (low stringency) can be used to identify related, but not exact, DNA molecules (homologous, but not identical) or segments.

DNA duplexes are stabilized by: (1) the number of complementary base pairs, (2) the type of base pairs, (3) salt concentration (ionic strength) of the reaction mixture, (4) the temperature of the reaction, and (5) the presence of certain organic solvents, such as formamide, which decrease DNA duplex stability. A common approach is to vary the temperature: higher relative temperatures result in more stringent reaction conditions (See, Ausubel, F. M., R. Brent, R. E. Kingston, et al. 1987. *Current Protocols in Molecular Biology*. John Wiley & Sons, New York) provide an excellent explanation of stringency of hybridization reactions.

Hybridization under "stringent conditions" means hybridization protocols in which nucleotide sequences at least 60% homologous to each other remain hybridized. Polynucleotides can include other appended groups such as peptides (e.g., for targeting host cell receptors in vivo), or agents facilitating transport across the cell membrane. In addition, oligonucleotides can be modified with hybridization-triggered cleavage agents (See, van der Krol et al., *Biotechniques*. 6:958-76 (1988) or intercalculating agents (Zon, G., *Pharm Res.* 5:539-49 (1988)). The oligonucleotide can be conjugated to another molecule, e.g., a peptide, a hybridization triggered cross-linking agent, a transport agent, a hybridization-triggered cleavage agent, and the like.

y) Subject(s) or Patient(s)

As used herein, the terms "subject" and "patient" are used interchangeably irrespective of whether the subject has or is currently undergoing any form of treatment. As used herein, the terms "subject" and "subjects" refer to any vertebrate, including, but not limited to, a mammal (e.g., cow, pig, camel, llama, horse, goat, rabbit, sheep, hamsters, guinea pig, cat, dog, rat, and mouse, a non-human primate (for example, a monkey, such as a cynomolgous monkey, chimpanzee, etc) and a human). Preferably, the subject is a human. Subjects or patients can be living or expired.

z) Target Sequence or Target Nucleic Acid Sequence

"Target sequence" or "target nucleic acid sequence" means a nucleic acid sequence encompassing, for example, a gene, or complements or fragments thereof, that is amplified, detected, or both using a polynucleotide primer or probe. Additionally, while the term target sequence sometimes refers to a double stranded nucleic acid sequence; a target sequence can also be single-stranded. In cases where the target is double-stranded, polynucleotide primer sequences preferably amplify both strands of the target sequence. A target sequence can be selected that is more or less specific for a particular organism. For example, the target sequence can be specific to an entire genus, to more than one genus, to a species or subspecies, serogroup, auxotype, serotype, strain, isolate or other subset of organisms.

aa) Test Sample

"Test sample" means a sample taken from a subject, or a biological fluid, wherein the sample may contain a target sequence. A test sample can be taken from any source, for example, tissue, blood, saliva, sputa, mucus, sweat, urine, urethral swabs, cervical swabs, urogenital or anal swabs, conjunctival swabs, ocular lens fluid, cerebral spinal fluid, etc. A test sample can be used (i) directly as obtained from the source; or (ii) following a pre-treatment to modify the character of the sample. Thus, a test sample can be pre-treated prior to use by, for example, preparing plasma or serum from blood, disrupting cells or viral particles, preparing liquids from solid materials, diluting viscous fluids, filtering liquids, adding reagents, purifying nucleic acids, etc.

bb) Therapeutically Effective Amount

The term "therapeutically effective amount" means an amount of drug, which is effective for producing a desired therapeutic effect upon administration to a patient, for example, to stem the growth, or result in the shrinkage, of a cancerous tumor or to produce the death of a cancerous cell or tumor.

cc) "Time Resolved-Fluorescence Resonance Energy Transfer"

As used herein, the phrase "Time Resolved-Fluorescence Resonance Energy Transfer" or "TR-FRET" refers to an assay that unites the principles of TRF (Time-Resolved Fluorescence) and FRET (Fluorescence Resonance Energy Transfer). A number of TR-FRET assays are known and commercially available in the art. An example of a TR-FRET that can be used in the present invention is described below.

Probe Synthesis

All reagents described below for use can be obtained from the vendor unless otherwise specified. Peptide synthesis reagents including diisopropylethylamine (DIEA), dichloromethane (DCM), N-methylpyrrolidone (NMP), 2-(1H-benzotriazole-1-yl)-1,1,3,3-tetramethyluronium hexafluorophosphate (HBTU), N-hydroxybenzotriazole (HOBt) and piperidine can be obtained from Applied Biosystems, Inc. (ABI), Foster City, Calif. or American Bioanalytical, Natick, Mass. Preloaded 9-Fluorenylmethyloxycarbonyl (Fmoc) amino acid cartridges (Fmoc-Ala-OH, Fmoc-Cys(Trt)-OH, Fmoc-Asp(tBu)-OH, Fmoc-Glu(tBu)-OH, Fmoc-Phe-OH, Fmoc-Gly-OH, Fmoc-His(Trt)-OH, Fmoc-Ile-OH, Fmoc-Leu-OH, Fmoc-Lys(Boc)-OH, Fmoc-Met-OH, Fmoc-Asn(Trt)-OH, Fmoc-Pro-OH, Fmor-Gln(Trt)-OH, Fmoc-Arg(Pbf)-OH, Fmoc-Ser(tBu)-OH, Fmoc-Thr(tBu)-OH, Fmoc-Val-OH, Fmoc-Trp(Boc)-OH, Fmoc-Tyr(tBu)-OH) can be obtained from ABI or Anaspec, San Jose, Calif. The peptide synthesis resin (Fmoc-Rink amide MBHA resin) and Fmoc-Lys(Mtt)-OH can be obtained from Novabiochem, San Diego, Calif. Single-isomer 6-carboxyfluorescein succinimidyl ester (6-FAM-NHS) can be obtained from Anaspec. Trifluoroacetic acid (TFA) can be obtained from Oakwood Products, West Columbia, S.C. Thioanisole, phenol, triisopropylsilane (TIS), 3,6-dioxa-1,8-octanedithiol (DODT) and isopropanol can be obtained from Aldrich Chemical Co., Milwaukee, Wis. Matrix-assisted laser desorption ionization mass-spectra (MALDI-MS) can be recorded on an Applied Biosystems Voyager DE-PRO MS). Electrospray mass-spectra (ESI-MS) can be recorded on Finnigan SSQ7000 (Finnigan Corp., San Jose, Calif.) in both positive and negative ion mode.

General Procedure For Solid-Phase Peptide Synthesis (SPPS)

Peptides can be synthesized with, at most, 250 µmol pre-loaded Wang resin/vessel on an ABI 433A peptide synthesizer using 250 µmol scale Fastmoc™ coupling cycles. Pre-loaded cartridges containing 1 mmol standard Fmoc-amino acids, except for the position of attachment of the fluorophore, where 1 mmol Fmoc-Lys(Mtt)-OH can be placed in the cartridge, and used with conductivity feedback monitoring. N-terminal acetylation can be accomplished by using 1 mmol acetic acid in a cartridge under standard coupling conditions.

Removal of 4-Methyltrityl (Mtt) From Lysine

The resin from the synthesizer can be washed thrice with DCM and kept wet. 150 mL of 95:4:1 dichloromethane:triisopropylsilane:trifluoroacetic acid can be flowed through the resin bed over 30 minutes. The mixture should turn deep yellow and then fad to pale yellow. 100 mL of DMF can be flowed through the bed over 15 minutes. The resin can then be washed thrice with DMF and filtered. Ninhydrin tests should show a strong signal for primary amine.

Resin Labeling With 6-Carboxyfluorescein-NHS (6-FAM-NHS)

The resin can be treated with 2 equivalents 6-FAM-NHS in 1% DIEA/DMF and stirred or shaken at ambient temperature overnight. When completed, the resin can be drained, washed thrice with DMF, thrice with (1% DCM and 1% methanol) and dried to provide an orange resin that was negative by ninhydrin test.

General Procedure for Cleavage and Deprotection of Resin-Bound Peptide

Peptides can be cleaved from the resin by shaking for 3 hours at ambient temperature in a cleavage cocktail consisting of 80% TFA, 5% water, 5% thioanisole, 5% phenol, 2.5% TIS, and 2.5% EDT (1 mL/0.1 g resin). The resin can be removed by filtration and rinsing twice with TFA. The TFA can be evaporated from the filtrates, and product precipitated with ether (10 mL/0.1 g resin), recovered by centrifugation, washed twice with ether (10 mL/0.1 g resin) and dried to give the crude peptide.

General Procedure For Purification Of Peptides

The crude peptides can be purified on a Gilson preparative HPLC system running Unipoint® analysis software (Gilson, Inc., Middleton, Wis.) on a radial compression column containing two 25×100 mm segments packed with Delta-Pak™ C18 15 µm particles with 100 Å pore size and eluted with one of the gradient methods listed below. One to two milliliters of crude peptide solution (10 mg/mL in 90% DMSO/water) can be purified per injection. The peaks containing the product(s) from each run can be pooled and lyophilized. All preparative runs can be run at 20 mL/min with eluents as buffer A: 0.1% TFA-water and buffer B: acetonitrile.

General Procedure For Analytical HPLC

Analytical HPLC was performed on a Hewlett-Packard 1200 series system with a diode-array detector and a Hewlett-Packard 1046A fluorescence detector running HPLC 3D ChemStation software version A.03.04 (Hewlett-Packard. Palo Alto, Calif.) on a 4.6×250 mm YMC column packed with ODS-AQ 5 µm particles with a 120 Å pore size and eluted with one of the gradient methods listed below after preequilibrating at the starting conditions for 7 minutes. Eluents were buffer A: 0.1% TFA-water and buffer B: acetonitrile. The flow rate for all gradients was 1 mL/min.

F-Bak: Peptide Probe: Acetyl-GQVGRQLAIIGDK(6-FAM)INR-NH$_2$ (SEQ ID NO:1).

Fmoc-Rink amide MBHA resin can be extended using the general peptide synthesis procedure to provide the protected resin-bound peptide (1.020 g). The Mtt group can be removed, labeled with 6-FAM-NHS and cleaved and deprotected as described hereinabove to provide the crude product as an orange solid (0.37 g). This product can be purified by RP-HPLC. Fractions across the main peak can be tested by analytical RP-HPLC, and the pure fractions can be isolated and lyophilized, with the major peak providing the title compound (0.0802 g) as a yellow solid; MALDI-MS m/z=2137.1 ((M+H)$^+$).

Alternative Synthesis of Peptide Probe F-Bak: Acetyl-GQVGRQLAIIGDK(6-FAM)INR—NH$_2$ (SEQ ID NO:1)

The protected peptide can be assembled on 0.25 mmol Fmoc-Rink amide MBHA resin (Novabiochem) on an Applied Biosystems 433A automated peptide synthesizer running Fastmoc™ coupling cycles using pre-loaded 1 mmol amino acid cartridges, except for the fluorescein(6-FAM)-labeled lysine, where 1 mmol Fmoc-Lys(4-methyltrityl) can be weighed into the cartridge. The N-terminal acetyl group can be incorporated by putting 1 mmol acetic acid in a cartridge and coupled as described hereinabove. Selective removal of the 4-methyltrityl group can be accomplished with a solution of 95:4:1 DCM:TIS:TFA (v/v/v) flowing through the resin over 15 minutes, followed by quenching with a flow of dimethylformamide. Single-isomer 6-carboxyfluorescein-NHS can be reacted with the lysine side-chain in 1% DIEA in DMF and confirmed complete by ninhydrin testing. The peptide can be cleaved from the resin and side-chains deprotected by treating with 80:5:5:5:2.5:2.5 TFA:water:phenol:thioanisole:triisopropylsilane: 3,6-dioxa-1,8-octanedithiol (v/v/v/v/v/v), and the crude peptide recovered by precipitation with diethyl ether. The crude peptide can be purified by reverse-phase high-performance liquid chromatography, and its purity and identity confirmed by analytical reverse-phase high-performance liquid chromatography and matrix-assisted laser-desorption mass-spectrometry (m/z=2137.1 ((M+H)$^+$)).

Time Resolved-Fluorescence Resonance Energy Transfer (TR-FRET) Assay

Representative compounds can be serially diluted in dimethyl sulfoxide (DMSO) starting at 50 µM (2× starting concentration; 10% DMSO) and 10 µL transferred into a 384-well plate. Then 10 µL of a protein/probe/antibody mix can be added to each well at final concentrations listed in the below Table AA

TABLE AA

Protein, Probe And Antibody For Use in TR-FRET Assays

| Protein | Probe | Protein (nM) | Probe (nM) | Antibody | Antibody (nM) |
|---|---|---|---|---|---|
| GST-Bcl-2 | F-Bak (SEQ. ID. No. 1) (GQVGRQLAIIGDK(6-FAM) (SEQ ID No. 2) INR-amide) | 1 | 100 | Tb-anti-GST | 1 |
| GST-Bcl-XL | F-Bak (SEQ. ID. No. 1) (GQVGRQLAIIGDK(6-FAM) (SEQ ID No. 2) INR-amide) | 1 | 100 | Tb-anti-GST | 1 |

6-FAM = 6-carboxyfluorescein.; Tb = terbium; GST = glutathione S-transferase

The samples can then mixed on a shaker for 1 minute and incubated for an additional 3 hours at room temperature. For each assay, the probe/antibody and protein/probe/antibody can be included on each assay plate as negative and positive controls, respectively. Fluorescence can be measured on the Envision (Perkin Elmer) using a 340/35 nm excitation filter and 520/525 (F-Bak peptide) and 495/510 nm (Tb-labeled anti-Histidine antibody) emission filters.

dd) Treat, Treating or Treatment

The terms "treat", "treating" or "treatment" as used herein refer to administering one or more active agents or compounds to a subject in an effort to (i) prevent a pathologic condition from occurring (e.g. prophylaxis); (ii) inhibit the pathologic condition or arrest its development; (iii) relieve a pathologic condition and/or prevent or reduce the severity one or more symptoms associated with such a pathologic condition, regardless of whether any of items (i) through (iii) are successful in a subject.

ee) Variant Polynucleotide or Variant Nucleic Acid Sequence

A "variant polynucleotide" or a "variant nucleic acid sequence" means a polynucleotide having at least about 60% nucleic acid sequence identity, more preferably at least about 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% nucleic acid sequence identity and yet more preferably at least about 99% nucleic acid sequence identity with a given nucleic acid sequence. Variants do not encompass the native nucleotide sequence.

Ordinarily, variant polynucleotides are at least about 8 nucleotides in length, often at least about 9, 10, 11, 12, 13, 14, 15, 16, 17, 18, 19, 20, 21, 22, 23, 24, 25, 26, 27, 28, 29 30, 35, 40, 45, 50, 55, 60 nucleotides in length, or even about 75-200 nucleotides in length, or more.

The realm of nucleotides includes derivatives wherein the nucleic acid molecule has been covalently modified by substitution, chemical, enzymatic, or other appropriate means with a moiety other than a naturally occurring nucleotide.

B. Bcl-2 Family Protein Inhibitors

In one aspect, the present disclosure relates to certain Bcl-2 family protein inhibitor compounds.

Variable moieties of compounds herein are represented by identifiers (capital letters with numerical and/or alphabetical superscripts) and may be specifically embodied.

It is meant to be understood that proper valences are maintained for all moieties and combinations thereof and that monovalent moieties having more than one atom are attached through their left ends.

It is also meant to be understood that a specific aspect of a variable moiety may be the same or different as another specific aspect having the same identifier.

Compounds of this disclosure may contain asymmetrically substituted carbon atoms in the R or S configuration, wherein the terms "R" and "S" are as defined in Pure Appl. Chem. (1976) 45, 13-10. Compounds having asymmetrically substituted carbon atoms with equal amounts of R and S configurations are racemic at those atoms. Atoms having excess of one configuration over the other are assigned the configuration in excess, preferably an excess of about 85%-90%, more preferably an excess of about 95%-99%, and still more preferably an excess greater than about 99%. Accordingly, this disclosure is meant to embrace racemic mixtures and relative and absolute diastereoisomers of the compounds thereof.

Compounds of this disclosure may also contain carbon-carbon double bonds or carbon-nitrogen double bonds in the Z or E configuration, in which the term "Z" represents the larger two substituents on the same side of a carbon-carbon or carbon-nitrogen double bond and the term "E" represents the larger two substituents on opposite sides of a carbon-carbon or carbon-nitrogen double bond. The compounds of this disclosure may also exist as a mixture of "Z" and "E" isomers.

Compounds of this disclosure may also exist as tautomers or equilibrium mixtures thereof wherein a proton of a compound shifts from one atom to another. Examples of tautomers include, but are not limited to, keto-enol, phenol-keto, oxime-nitroso, nitro-acid, imine-enamine and the like.

Compounds having formula (II) having NH, C(O)OH, OH or SH moieties may have attached thereto prodrug-forming moieties. The prodrug-forming moieties are removed by metabolic processes and release the compounds having the freed NH, C(O)OH, OH or SH in vivo. Prodrugs are useful for adjusting such pharmacokinetic properties of the compounds as solubility and/or hydrophobicity, absorption in the gastrointestinal tract, bioavailability, tissue penetration, and rate of clearance.

Metabolites of compounds having formula (II), produced by in vitro or in vivo metabolic processes, may also have utility for treating diseases associated with expression of an anti-apoptotic family protein member such as of Bcl-$X_L$ protein, Bcl-2 protein or Bcl-w protein.

Certain precursor compounds which may be metabolized in vitro or in vivo to form compounds having formula (II) may also have utility for treating diseases associated with expression of an anti-apoptotic family protein member such as of Bcl-$X_L$ protein, Bcl-2 protein or Bcl-w protein.

Compounds having formula (II) may exist as acid addition salts, basic addition salts or zwitterions. Salts of compounds having formula (II) are prepared during their isolation or following their purification. Acid addition salts are those derived from the reaction of a compound having formula (II) with acid. Accordingly, salts including the acetate, adipate, alginate, bicarbonate, citrate, aspartate, benzoate, benzenesulfonate (besylate), bisulfate, butyrate, camphorate, camphorsulfonate, digluconate, formate, fumarate, glycerophosphate, glutamate, hemisulfate, heptanoate, hexanoate, hydrochloride, hydrobromide, hydroiodide, lactobionate, lactate, maleate, mesitylenesulfonate, methanesulfonate, naphthylenesulfonate, nicotinate, oxalate, pamoate, pectinate, persulfate, phosphate, picrate, propionate, succinate, tartrate, thiocyanate, trichloroacetic, trifluoroacetic, paratoluenesulfonate and undecanoate salts of the compounds having formula (II) are meant to be embraced by this disclosure. Basic addition salts of compounds are those derived from the reaction of the compounds having formula (II) with the bicarbonate, carbonate, hydroxide or phosphate of cations such as lithium, sodium, potassium, calcium and magnesium.

Compounds having formula (II) may be administered, for example, bucally, ophthalmically, orally, osmotically, parenterally (intramuscularly, intraperitoneally intrasternally, intravenously, subcutaneously), rectally, topically, transdermally, vaginally and intraarterially as well as by intraarticular injection, infusion, and placement in the body, such as, for example, the vasculature by means of, for example, a stent.

Therapeutically effective amounts of a compound having formula (II) depend on recipient of treatment, disease treated and severity thereof, composition comprising it, time of administration, route of administration, duration of treatment, potency, rate of clearance and whether or not another drug is co-administered. The amount of a compound having formula (II) used to make a composition to be administered daily to a patient in a single dose or in divided doses is from about 0.03 to about 200 mg/kg body weight. Single dose compositions contain these amounts or a combination of submultiples thereof.

Compounds having formula (II) may be administered with or without an excipient. Excipients include, but are not limited to, encapsulators and additives such as absorption accelerators, antioxidants, binders, buffers, coating agents, coloring agents, diluents, disintegrating agents, emulsifiers, extenders, fillers, flavoring agents, humectants, lubricants, perfumes, preservatives, propellants, releasing agents, sterilizing agents, sweeteners, solubilizers, wetting agents, mixtures thereof and the like.

Excipients for preparation of compositions comprising a compound having formula (II) to be administered orally include, but are not limited to, agar, alginic acid, aluminum hydroxide, benzyl alcohol, benzyl benzoate, 1,3-butylene glycol, carbomers, castor oil, cellulose, cellulose acetate, cocoa butter, corn starch, corn oil, cottonseed oil, cross-povidone, diglycerides, ethanol, ethyl cellulose, ethyl laureate, ethyl oleate, fatty acid esters, gelatin, germ oil, glucose, glycerol, groundnut oil, hydroxypropylmethyl celluose, isopropanol, isotonic saline, lactose, magnesium hydroxide, magnesium stearate, malt, mannitol, monoglycerides, olive oil, peanut oil, potassium phosphate salts, potato starch, povidone, propylene glycol, Ringer's solution, safflower oil, sesame oil, sodium carboxymethyl cellulose, sodium phosphate salts, sodium lauryl sulfate, sodium sorbitol, soybean oil, stearic acids, stearyl fumarate, sucrose, surfactants, talc, tragacanth, tetrahydrofurfuryl alcohol, triglycerides, water, mixtures thereof and the like. Excipients for preparation of compositions comprising a compound having formula (II) to be administered ophthalmically or orally include, but are not limited to, 1,3-butylene glycol, castor oil, corn oil, cottonseed oil, ethanol, fatty acid esters of sorbitan, germ oil, groundnut oil, glycerol, isopropanol, olive oil, polyethylene glycols, propylene glycol, sesame oil, water, mixtures thereof and the like. Excipients for preparation of compositions comprising a compound having formula (II) to be administered osmotically include, but are not limited to, chlorofluorohydrocarbons, ethanol, water, mixtures thereof and the like. Excipients for preparation of compositions comprising a compound having formula (II) to be administered parenterally include, but are not limited to, 1,3-butanediol, castor oil, corn oil, cottonseed oil, dextrose, germ oil, groundnut oil, liposomes, oleic acid, olive oil, peanut oil, Ringer's solution, safflower oil, sesame oil, soybean oil, U.S.P. or isotonic sodium chloride solution, water, mixtures thereof and the like. Excipients for preparation of compositions comprising a compound having formula (II) to be administered rectally or vaginally include, but are not limited to, cocoa butter, polyethylene glycol, wax, mixtures thereof and the like.

This disclosure also comprises combination therapeutic methods of treating disease conditions involving abnormal cell growth and/or dysregulated apoptosis, such as cancer, in a patient comprising administering thereto a therapeutically effective amount of a pharmaceutical composition comprising a compound having formula (II) and a therapeutically effective amount of one or more than one additional therapeutic agents and/or ionizing radiation.

The combination therapeutic methods include administering compositions of a compound having formula (II) and one or more than one additional therapeutic agents or ionizing radiation to a patient using any desired dosing and/or scheduling regimen.

Compounds having formula (II) are expected to be useful when used with alkylating agents, angiogenesis inhibitors, antibodies, antimetabolites, antimitotics, antiproliferatives, antivirals, aurora kinase inhibitors, other apoptosis promoters (for example, Bcl-xL, Bcl-w and Bfl-1) inhibitors, activators of death receptor pathway, Bcr-Abl kinase inhibitors, BiTE (Bi-Specific T cell Engager) antibodies, antibody drug conjugates, biologic response modifiers, cyclin-dependent kinase inhibitors, cell cycle inhibitors, cyclooxygenase-2 inhibitors, DVDs, leukemia viral oncogene homolog (ErbB2) receptor inhibitors, growth factor inhibitors, heat shock protein (HSP)-90 inhibitors, histone deacetylase (HDAC) inhibitors, hormonal therapies, immunologicals, inhibitors of inhibitors of apoptosis proteins (IAPs), intercalating antibiotics, kinase inhibitors, kinesin inhibitors, Jak2 inhibitors, mammalian target of rapamycin inhibitors, microRNA's, mitogen-activated extracellular signal-regulated kinase inhibitors, multivalent binding proteins, non-steroidal anti-inflammatory drugs (NSAIDs), poly ADP (adenosine diphosphate)-ribose polymerase (PARP) inhibitors, platinum chemotherapeutics, polo-like kinase (Plk) inhibitors, phosphoinositide-3 kinase (PI3K) inhibitors, proteosome inhibitors, purine analogs, pyrimidine analogs, receptor tyrosine kinase inhibitors, etinoids/deltoids plant alkaloids, small inhibitory ribonucleic acids (siRNAs), topoisomerase inhibitors, ubiquitin ligase inhibitors, and the like, and in combination with one or more of these agents.

BiTE antibodies are bi-specific antibodies that direct T-cells to attack cancer cells by simultaneously binding the two cells. The T-cell then attacks the target cancer cell.

Examples of BiTE antibodies include adecatumumab (Micromet MT201), blinatumomab (Micromet MT103) and the like. Without being limited by theory, one of the mechanisms by which T-cells elicit apoptosis of the target cancer cell is by exocytosis of cytolytic granule components, which include perforin and granzyme B. In this regard, Bcl-2 has been shown to attenuate the induction of apoptosis by both perforin and granzyme B. These data suggest that inhibition of Bcl-2 could enhance the cytotoxic effects elicited by T-cells when targeted to cancer cells (V. R. Sutton, D. L. Vaux and J. A. Trapani (1997) *J. of Immunology.* 158 (12): 5783).

SiRNAs are molecules having endogenous RNA bases or chemically modified nucleotides. The modifications do not abolish cellular activity, but rather impart increased stability and/or increased cellular potency. Examples of chemical modifications include phosphorothioate groups, 2'-deoxynucleotide, 2'-OCH3-containing ribonucleotides, 2'-F-ribonucleotides, 2'-methoxyethyl ribonucleotides, combinations thereof and the like. The siRNA can have varying lengths (e.g., 10-200 bps) and structures (e.g., hairpins, single/double strands, bulges, nicks/gaps, mismatches) and are processed in cells to provide active gene silencing. A double-stranded siRNA (dsRNA) can have the same number of nucleotides on each strand (blunt ends) or asymmetric ends (overhangs). The overhang of 1-2 nucleotides can be present on the sense and/or the antisense strand, as well as present on the 5'- and/or the 3'-ends of a given strand. For example, siRNAs targeting Mcl-1 have been shown to enhance the activity of ABT-263, (i.e., N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide) or ABT-737 (i.e., N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide) in multiple tumor cell lines (Tse et. al (2008) *Cancer Research.* 68(9): 3421 and references therein).

Multivalent binding proteins are binding proteins comprising two or more antigen binding sites. Multivalent binding proteins are engineered to have the three or more antigen binding sites and are generally not naturally occurring antibodies. The term "multispecific binding protein" means a binding protein capable of binding two or more related or unrelated targets. Dual variable domain (DVD) binding proteins are tetravalent or multivalent binding proteins binding proteins comprising two or more antigen binding sites. Such DVDs may be monospecific (i.e., capable of binding one antigen) or multispecific (i.e., capable of binding two or more antigens). DVD binding proteins comprising two heavy chain DVD polypeptides and two light chain DVD polypeptides are referred to as DVD Ig's. Each half of a DVD Ig comprises a heavy chain DVD polypeptide, a light chain DVD polypeptide, and two antigen binding sites. Each binding site comprises a heavy chain variable domain and a light chain variable domain with a total of 6 CDRs involved in antigen binding per antigen binding site.

Alkylating agents include altretamine, AMD-473, AP-5280, apaziquone, bendamustine, brostallicin, busulfan, carboquone, carmustine (BCNU), chlorambucil, CLORETAZINE® (laromustine, VNP 40101M), cyclophosphamide, decarbazine, estramustine, fotemustine, glufosfamide, ifosfamide, KW-2170, lomustine (CCNU), mafosfamide, melphalan, mitobronitol, mitolactol, nimustine, nitrogen mustard N-oxide, ranimustine, temozolomide, thiotepa, TREANDA® (bendamustine), treosulfan, rofosfamide and the like.

Angiogenesis inhibitors include endothelial-specific receptor tyrosine kinase (Tie-2) inhibitors, epidermal growth factor receptor (EGFR) inhibitors, insulin growth factor-2 receptor (IGFR-2) inhibitors, matrix metalloproteinase-2 (MMP-2) inhibitors, matrix metalloproteinase-9 (MMP-9) inhibitors, platelet-derived growth factor receptor (PDGFR) inhibitors, thrombospondin analogs, vascular endothelial growth factor receptor tyrosine kinase (VEGFR) inhibitors and the like.

Antimetabolites include ALIMTA® (pemetrexed disodium, LY231514, MTA), 5-azacitidine, XELODA® (capecitabine), carmofur, LEUSTAT® (cladribine), clofarabine, cytarabine, cytarabine ocfosfate, cytosine arabinoside, decitabine, deferoxamine, doxifluridine, eflornithine, EICAR (5-ethynyl-1-D-ribofuranosylimidazole-4-carboxamide), enocitabine, ethnylcytidine, fludarabine, 5-fluorouracil alone or in combination with leucovorin, GEMZAR® (gemcitabine), hydroxyurea, ALKERAN® (melphalan), mercaptopurine, 6-mercaptopurine riboside, methotrexate, mycophenolic acid, nelarabine, nolatrexed, ocfosfate, pelitrexol, pentostatin, raltitrexed, Ribavirin, triapine, trimetrexate, S-1, tiazofurin, tegafur, TS-1, vidarabine, UFT and the like.

Antivirals include ritonavir, hydroxychloroquine and the like.

Bcr-Abl kinase inhibitors include DASATINIB® (BMS-354825), GLEEVEC® (imatinib) and the like.

CDK inhibitors include AZD-5438, BMI-1040, BMS-032, BMS-387, CVT-2584, flavopyridol, GPC-286199, MCS-5A, PD0332991, PHA-690509, seliciclib (CYC-202, R-roscovitine), ZK-304709 and the like.

COX-2 inhibitors include ABT-963, ARCOXIA® (etoricoxib), BEXTRA® (valdecoxib), BMS347070, CELEBREX® (celecoxib), COX-189 (lumiracoxib), CT-3, DERAMAXX® (deracoxib), JTE-522, 4-methyl-2-(3,4-dimethylphenyl)-1-(4-sulfamoylphenyl-1H-pyrrole), MK-663 (etoricoxib), NS-398, parecoxib, RS-57067, SC-58125, SD-8381, SVT-2016, S-2474, T-614, VIOXX® (rofecoxib) and the like.

EGFR inhibitors include ABX-EGF, anti-EGFR immunoliposomes, EGF-vaccine, EMD-7200, ERBITUX® (cetuximab), HR3, IgA antibodies, IRESSA® (gefitinib), TARCEVA® (erlotinib or OSI-774), TP-38, EGFR fusion protein, TYKERB® (lapatinib) and the like.

ErbB2 receptor inhibitors include CP-724-714, CI-1033 (canertinib), HERCEPTIN® (trastuzumab), TYKERB® (lapatinib), OMNITARG® (2C4, petuzumab), TAK-165, GW-572016 (ionafarnib), GW-282974, EKB-569, PI-166, dHER2 (HER2 vaccine), APC-8024 (HER-2 vaccine), anti-HER/2neu bispecific antibody, B7.her2IgG3, AS HER2 trifunctional bispecific antibodies, mAB AR-209, mAB 2B-1 and the like.

Histone deacetylase inhibitors include depsipeptide, LAQ-824, MS-275, trapoxin, suberoylanilide hydroxamic acid (SAHA), TSA, valproic acid and the like.

HSP-90 inhibitors include 17-AAG-nab, 17-AAG, CNF-101, CNF-1010, CNF-2024, 17-DMAG, geldanamycin, IPI-504, KOS-953, MYCOGRAB® (human recombinant antibody to HSP-90), NCS-683664, PU24FC1, PU-3, radicicol, SNX-2112, STA-9090 VER49009 and the like.

Inhibitors of inhibitors of apoptosis proteins include HGS1029, GDC-0145, GDC-0152, LCL-161, LBW-242 and the like.

Antibody drug conjugates include anti-CD22-MC-MMAF, anti-CD22-MC-MMAE, anti-CD22-MCC-DM1, CR-0,1-vcMMAE, PSMA-ADC, MEDI-547, SGN-19Am SGN-35, SGN-75 and the like.

Activators of death receptor pathway include TRAIL, antibodies or other agents that target TRAIL or death receptors (e.g., DR4 and DR5) such as Apomab, conatumumab, ETR2-ST01, GDC0145, (lexatumumab), HGS-1029, LBY-135, PRO-1762 and trastuzumab.

Kinesin inhibitors include Eg5 inhibitors such as AZD4877, ARRY-520; CENPE inhibitors such as GSK923295A and the like.

JAK-2 inhibitors include CEP-701 (lesaurtinib), XL019 and INCB018424 and the like.

MEK inhibitors include ARRY-142886, ARRY-438162 PD-325901, PD-98059 and the like.

mTOR inhibitors include AP-23573, CCI-779, everolimus, RAD-001, rapamycin, temsirolimus, ATP-competitive TORC1/TORC2 inhibitors, including PI-103, PP242, PP30, Torin 1 and the like.

Non-steroidal anti-inflammatory drugs include AMIGESIC® (salsalate), DOLOBID® (diflunisal), MOTRIN® (ibuprofen), ORUDIS® (ketoprofen), RELAFEN® (nabumetone), FELDENE® (piroxicam), ibuprofen cream, ALEVE® (naproxen) and NAPROSYN® (naproxen), VOLTAREN® (diclofenac), INDOCIN® (indomethacin), CLINORIL® (sulindac), TOLECTIN® (tolmetin), LODINE® (etodolac), TORADOL® (ketorolac), DAYPRO® (oxaprozin) and the like.

PDGFR inhibitors include C-451, CP-673, CP-868596 and the like.

Platinum chemotherapeutics include cisplatin, ELOXATIN® (oxaliplatin) eptaplatin, lobaplatin, nedaplatin, PARAPLATIN® (carboplatin), satraplatin, picoplatin and the like.

Polo-like kinase inhibitors include BI-2536 and the like.

Phosphoinositide-3 kinase (PI3K) inhibitors include wortmannin, LY294002, XL-147, CAL-120, ONC-21, AEZS-127, ETP-45658, PX-866, GDC-0941, BGT226, BEZ235, XL765 and the like.

Thrombospondin analogs include ABT-510, ABT-567, ABT-898, TSP-1 and the like.

VEGFR inhibitors include AVASTIN® (bevacizumab), ABT-869, AEE-788, ANGIOZYME™ (a ribozyme that inhibits angiogenesis (Ribozyme Pharmaceuticals (Boulder, Colo.) and Chiron, (Emeryville, Calif.)), axitinib (AG-13736), AZD-2171, CP-547,632, IM-862, MACUGEN (pegaptamib), NEXAVAR® (sorafenib, BAY43-9006), pazopanib (GW-786034), vatalanib (PTK-787, ZK-222584), SUTENT® (sunitinib, SU-11248), VEGF trap, ZACTIMA™ (vandetanib, ZD-6474) and the like.

Antibiotics include intercalating antibiotics aclarubicin, actinomycin D, amrubicin, annamycin, adriamycin, BLENOXANE® (bleomycin), daunorubicin, CAELYX® or MYOCET® (liposomal doxorubicin), elsamitrucin, epirbucin, glarbuicin, ZAVEDOS® (idarubicin), mitomycin C, nemorubicin, neocarzinostatin, peplomycin, pirarubicin, rebeccamycin, stimalamer, streptozocin, VALSTAR® (valrubicin), zinostatin and the like.

Topoisomerase inhibitors include aclarubicin, 9-aminocamptothecin, amonafide, amsacrine, becatecarin, belotecan, BN-80915, CAMPTOSAR® (irinotecan hydrochloride), camptothecin, CARDIOXANE® (dexrazoxine), diflomotecan, edotecarin, ELLENCE® or PHARMORUBICIN® (epirubicin), etoposide, exatecan, 10-hydroxycamptothecin, gimatecan, lurtotecan, mitoxantrone, orathecin, pirarbucin, pixantrone, rubitecan, sobuzoxane, SN-38, tafluposide, topotecan and the like.

Antibodies include AVASTIN® (bevacizumab), CD40-specific antibodies, chTNT-1/B, denosumab, ERBITUX® (cetuximab), HUMAX-CD4® (zanolimumab), IGF1R-specific antibodies, lintuzumab, PANOREX® (edrecolomab), RENCAREX® (WX G250), RITUXAN® (rituximab), ticilimumab, trastuzimab, CD20 antibodies types I and II and the like.

Hormonal therapies include ARIMIDEX® (anastrozole), AROMASIN® (exemestane), arzoxifene, CASODEX® (bicalutamide), CETROTIDE® (cetrorelix), degarelix, deslorelin, DESOPAN® (trilostane), dexamethasone, DROGENIL® (flutamide), EVISTA® (raloxifene), AFEMA™ (fadrozole), FARESTON® (toremifene), FASLODEX® (fulvestrant), FEMARA® (letrozole), formestane, glucocorticoids, HECTOROL® (doxercalciferol), RENAGEL® (sevelamer carbonate), lasofoxifene, leuprolide acetate, MEGACE® (megesterol), MIFEPREX® (mifepristone), NILANDRON™ (nilutamide), NOLVADEX® (tamoxifen citrate), PLENAXIS™ (abarelix), prednisone, PROPECIA® (finasteride), rilostane, SUPREFACT® (buserelin), TRELSTAR® (luteinizing hormone releasing hormone (LHRH)), VANTAS® (Histrelin implant), VETORYL® (trilostane or modrastane), ZOLADEX® (fosrelin, goserelin) and the like.

Deltoids and retinoids include seocalcitol (EB1089, CB1093), lexacalcitrol (KH1060), fenretinide, PANRETIN® (aliretinoin), ATRAGEN® (liposomal tretinoin), TARGRETIN® (bexarotene), LGD-1550 and the like.

PARP inhibitors include ABT-888, olaparib, KU-59436, AZD-2281, AG-014699, BSI-201, BGP-15, INO-1001, ONO-2231 and the like.

Plant alkaloids include, but are not limited to, vincristine, vinblastine, vindesine, vinorelbine and the like.

Proteasome inhibitors include VELCADE® (bortezomib), MG132, NPI-0052, PR-171 and the like.

Examples of immunologicals include interferons and other immune-enhancing agents. Interferons include interferon alpha, interferon alpha-2a, interferon alpha-2b, interferon beta, interferon gamma-1a, ACTIMMUNE® (interferon gamma-1b) or interferon gamma-nl, combinations thereof and the like. Other agents include ALFAFERONE®, (IFN—), BAM-002 (oxidized glutathione), BEROMUN® (tasonermin), BEXXAR® (tositumomab), CAMPATH® (alemtuzumab), CTLA4 (cytotoxic lymphocyte antigen 4), decarbazine, denileukin, epratuzumab, GRANOCYTE® (lenograstim), lentinan, leukocyte alpha interferon, imiquimod, MDX-010 (anti-CTLA-4), melanoma vaccine, mitumomab, molgramostim, MYLOTARG™ (gemtuzumab ozogamicin), NEUPOGEN® (filgrastim), OncoVAC-CL, OVAREX® (oregovomab), pemtumomab (Y-muHMFG1), PROVENGE® (sipuleucel-T), sargaramostim, sizofilan, teceleukin, THERACYS® (Bacillus Calmette-Guerin), ubenimex, VIRULIZIN® (immunotherapeutic, Lorus Pharmaceuticals), Z-100 (Specific Substance of Maruyama (SSM)), WF-10 (Tetrachlorodecaoxide (TCDO)), PROLEUKIN® (aldesleukin), ZADAXIN® (thymalfasin), ZENAPAX® (daclizumab), ZEVALIN® (90Y-Ibritumomab tiuxetan) and the like.

Biological response modifiers are agents that modify defense mechanisms of living organisms or biological responses, such as survival, growth or differentiation of tissue cells to direct them to have anti-tumor activity and include krestin, lentinan, sizofuran, picibanil PF-3512676 (CpG-8954), ubenimex and the like.

Pyrimidine analogs include cytarabine (ara C or Arabinoside C), cytosine arabinoside, doxifluridine, FLUDARA® (fludarabine), 5-FU (5-fluorouracil), floxuridine, GEMZAR® (gemcitabine), TOMUDEX® (ratitrexed), TROXATYL™ (triacetyluridine troxacitabine) and the like.

Purine analogs include LANVIS® (thioguanine) and PURI-NETHOL® (mercaptopurine).

Antimitotic agents include batabulin, epothilone D (KOS-862), N-(2-((4-hydroxyphenyl)amino)pyridin-3-yl)-4-methoxybenzenesulfonamide, ixabepilone (BMS 247550), paclitaxel, TAXOTERE® (docetaxel), PNU100940 (109881), patupilone, XRP-9881 (larotaxel), vinflunine, ZK-EPO (synthetic epothilone) and the like.

Ubiquitin ligase inhibitors include MDM2 inhibitors, such as nutlins, NEDD8 inhibitors such as MLN4924 and the like.

Compounds of this disclosure can also be used as radiosensitizers that enhance the efficacy of radiotherapy. Examples of radiotherapy include external beam radiotherapy, teletherapy, brachytherapy and sealed, unsealed source radiotherapy and the like.

Additionally, compounds having Formula (II) may be combined with other chemotherapeutic agents such as ABRAXANE™ (ABI-007), ABT-100 (farnesyl transferase inhibitor), ADVEXIN® (Ad5CMV-p53 vaccine), ALTOCOR® or MEVACOR® (lovastatin), AMPLIGEN® (poly I:poly C12U, a synthetic RNA), APTOSYN® (exisulind), AREDIA® (pamidronic acid), arglabin, L-asparaginase, atamestane (1-methyl-3,17-dione-androsta-1,4-diene), AVAGE® (tazarotene), AVE-8062 (combreastatin derivative) BEC2 (mitumomab), cachectin or cachexin (tumor necrosis factor), canvaxin (vaccine), CEAVAC® (cancer vaccine), CELEUK® (celmoleukin), CEPLENE® (histamine dihydrochloride), CERVARIX® (human papillomavirus vaccine), CHOP® (C: CYTOXAN® (cyclophosphamide); H: ADRIAMYCIN® (hydroxydoxorubicin); 0: Vincristine (ONCOVIN®); P: prednisone), CYPAT™ (cyproterone acetate), combrestatin A4P, DAB(389)EGF (catalytic and translocation domains of diphtheria toxin fused via a His-Ala linker to human epidermal growth factor) or TransMID-107R™ (diphtheria toxins), dacarbazine, dactinomycin, 5,6-dimethylxanthenone-4-acetic acid (DMXAA), eniluracil, EVIZON™ (squalamine lactate), DIMERICINE® (T4N5 liposome lotion), discodermolide, DX-8951f (exatecan mesylate), enzastaurin, EPO906 (epithilone B), GARDASIL® (quadrivalent human papillomavirus (Types 6, 11, 16, 18) recombinant vaccine), GASTRIMMUNE®, GENASENSE®, GMK (ganglioside conjugate vaccine), GVAX® (prostate cancer vaccine), halofuginone, histerelin, hydroxycarbamide, ibandronic acid, IGN-101, IL-13-PE38, IL-13-PE38QQR (cintredekin besudotox), IL-13-pseudomonas exotoxin, interferon-α, interferon-γ, JUNOVAN™ or MEPACT™ (mifamurtide), lonafarnib, 5,10-methylenetetrahydrofolate, miltefosine (hexadecylphosphocholine), NEOVASTAT® (AE-941), NEUTREXIN® (trimetrexate glucuronate), NIPENT® (pentostatin), ONCONASE® (a ribonuclease enzyme), ONCOPHAGE® (melanoma vaccine treatment), ONCOVAX® (IL-2 Vaccine), ORATHECIN™ (rubitecan), OSIDEM® (antibody-based cell drug), OVAREX® MAb (murine monoclonal antibody), paclitaxel, PANDIMEX™ (aglycone saponins from ginseng comprising 20(S)protopanaxadiol (aPPD) and 20(S)protopanaxatriol (aPPT)), panitumumab, PANVAC®-VF (investigational cancer vaccine), pegaspargase, PEG Interferon A, phenoxodiol, procarbazine, rebimastat, REMOVAB® (catumaxomab), REVLIMID® (lenalidomide), RSR13 (efaproxiral), SOMATULINE® LA (lanreotide), SORIATANE® (acitretin), staurosporine (*Streptomyces staurospores*), talabostat (PT100), TARGRETIN® (bexarotene), TAXOPREXIN® (DHA-paclitaxel), TELCYTA® (canfosfamide, TLK286), temilifene, TEMODAR® (temozolomide), tesmilifene, thalidomide, THERATOPE® (STn-KLH), thymitaq (2-amino-3,4-dihydro-6-methyl-4-oxo-5-(4-pyridylthio)quinazoline dihydrochloride), TNFERADE™ (adenovector: DNA carrier containing the gene for tumor necrosis factor-α), TRACLEER® or ZAVESCA® (bosentan), tretinoin (Retin-A), tetrandrine, TRISENOX® (arsenic trioxide), VIRULIZIN®, ukrain (derivative of alkaloids from the greater celandine plant), vitaxin (anti-alphavbeta3 antibody), XCYTRIN® (motexafin gadolinium), XINLAY™ (atrasentan), XYOTAX™ (paclitaxel poliglumex), YONDELIS® (trabectedin), ZD-6126, ZINECARD® (dexrazoxane), ZOMETA® (zolendronic acid), zorubicin and the like.

BAX and BAD peptides are reported in Zhang, H. C., Nimmer, P., Rosenberg, S. H., Ng, S. C., and Joseph, M. (2002). Development of a High-Throughput Fluorescence Polarization Assay for Bcl-x(L). *Analytical Biochemistry* 307, 70-75.

Binding affinity of compounds having formula (II) to Bcl-$X_L$ protein is indicia of their inhibition of the activity of this protein. To determine the binding affinity of compounds having formula (II) to Bcl-$X_L$ protein, representative examples were diluted in DMSO to concentrations between 100 μM and 1 μM and added to each well of a 96-well microtiter plate. A mixture comprising 125 μL per well of assay buffer (20 mM phosphate buffer (pH 7.4), 1 mM EDTA, 50 mM NaCl, 0.05% PF-68), 6 nM of Bcl-$X_L$ protein (prepared as described in *Science* 1997, 275, 983-986), 1 nM fluorescein-labeled BAD peptide (prepared in-house) and the DMSO solution of the compound was shaken for 2 minutes and placed in a LJL Analyst (LJL Bio Systems, CA). A negative control (DMSO, 15 nM BAD peptide, assay buffer) and a positive control (DMSO, 1 nM BAD peptide, 6 nM Bcl-$X_L$, assay buffer) were used to determine the range of the assay. Polarization was measured at room temperature using a continuous Fluorescein lamp (excitation 485 nm, emission 530 nm). Percentage of inhibition was determined by (1-((mP value of well-negative control)/range))×100%. The results are shown in TABLE 1.

Binding affinity of compounds having formula (II) to Bcl-2 protein is indicia of their inhibition of the activity of this protein. To determine the binding affinity of compounds having formula (II) to Bcl-2, representative examples were diluted in DMSO to concentrations between 10 μM and 10 μM and added to each well of a 96-well microtiter plate. A mixture comprising 125 L per well of assay buffer (20 mM phosphate buffer (pH 7.4), 1 mM EDTA, 50 mM NaCl, 0.05% PF-68), 10 nM of Bcl-2 protein (prepared according to the procedure described in PNAS 2001, 98, 3012-3017), 1 nM fluorescein-labeled BAX peptide (prepared in-house) and the DMSO solution of the representative EXAMPLE was shaken for 2 minutes and placed in a LJL Analyst (LJL Bio Systems, CA. Polarization was measured at room temperature using a continuous Fluorescein lamp (excitation 485 nm, emission 530 nm). The results are also shown in TABLE 1.

These data demonstrate the utility of compounds having formula (II) as binders to and inhibitors of anti-apoptotic Bcl-$X_L$ protein and anti-apoptotic Bcl-2.

It is expected that, because compounds having formula (II) bind to and inhibit the activity of Bcl-$X_L$ and Bcl-2, they would also have utility as inhibitors of anti-apoptotic family protein members having close structural homology to Bcl-$X_L$ and Bcl-2 such as, for example, anti-apoptotic Bcl-w protein.

Accordingly, compounds having formula (II) are expected to have utility in treatment of diseases during which anti-apoptotic Bcl-$X_L$ protein, anti-apoptotic Bcl-2 protein, anti-apoptotic Bcl-w protein or a combination thereof, are expressed.

Determination of Cellular Efficacy in Human Tumor Cell Line

NCI-H146 (ATCC, Manassas, Va.) human small cell lung carcinoma cells were plated 50,000 cells per well in 96-well tissue culture plates in a total volume of 100 μL tissue culture medium supplemented with 10% human serum (Invitrogen, Carlsbad, Calif.) instead of fetal bovine serum and treated with a 2-fold serial dilution of the compounds of interest from 10 μM to 0.020 μM. Each concentration was tested in duplicate at least 3 separate times. The number of viable cells following 48 hours of compound treatment was determined using the CellTiter 96® AQ$_{ueous}$ non-radioactive cell proliferation MTS assay according to manufacturer's recommendations (Promega Corp., Madison, Wis.). The results are also shown in TABLE 1.

Pharmacokinetic Evaluation of Selected Compounds in Rat

The pharmacokinetic behavior of compounds of this disclosure was determined following a single 2 mg/kg intravenous or 5 mg/kg oral dose in male Sprague-Dawley derived rats (n=3 per group). The compounds were prepared as 2 mg/mL solution in a 10% DMSO in PEG-400 formulation for both oral and intravenous administration. The 1 mL/kg intravenous dose was administered as a slow bolus (about 1-2 minutes) in the jugular vein of a rat under light ether anesthetic. The oral dose was administered by gavage. Serial blood samples were obtained from a tail vein of each rat prior 0.1 (IV only), 0.25, 0.5, 1, 1.5, 2, 3, 4, 6, 8 and 24 hours after dosing. The heparinized samples were thoroughly mixed and placed in an ice bath. Plasma was separated by centrifugation and stored frozen prior to analysis. The results are also shown in TABLE 1.

The compounds of interest were separated from the plasma using protein precipitation with acetonitrile. A plasma (100-200 μL, sample or spiked standard) aliquot was combined with 50 μL of internal standard (structurally related analog prepared in acetonitrile) and 1 ml acetonitrile in a 96-well polypropylene deep well plate. The plates were vortexed for 30 seconds followed by centrifugation (3500 rpm×15 minutes, 4° C.). In an automated manner, the supernatant was transferred to a clean 96-well plate. The samples were evaporated to near dryness on a Micro-Vap™ under a stream of dry nitrogen over low heat (~37° C.). The samples were reconstituted vortexing with 0.2 mL 5% DMSO in acetonitrile. A 0.1-0.2 ml aliquot of acetonitrile: 0.1% trifluoroacetic acid (20:80, by volume) was added to each well, followed by an additional 30 second vortexing. The plates were centrifuged (3500 rpm×15 minutes, 4° C.) prior to HPLC-MS/MS analysis. Samples were analyzed simultaneously with spiked plasma standards. All samples from each study were analyzed as a single batch on the LC-MS/MS.

The compounds of interest and the internal standard were separated from each other and co-extracted contaminants on a 50×3 mm Keystone Betasil CN 5 μm column with an acetonitrile: 0.1% trifluoroacetic acid mobile phase (50:50, by volume) at a flow rate of 0.7 ml/min. Analysis was performed on a Sciex API 300™ Biomolecular Mass Analyzer using a heated nebulizer interface. Peak areas of the title compounds and internal standards were determined using the Sciex MacQuan™ software. Calibration curves were derived from peak area ratio (parent drug/internal standard) of the spiked rat plasma standards using least squares linear regression of the ratio versus the theoretical concentration. The methods were generally linear over the range of the standard curve (correlation coefficients >0.99) with an estimated quantitation limit of 0.01 μg/mL. The plasma concentration data for each animal were submitted to multi-exponential curve fitting using WinNonlin. The area under the plasma concentration-time curve from 0 to t hours (time of the last measurable plasma concentration) after dosing (AUC$_{0-t}$) was calculated using the linear trapezoidal rule for the plasma concentration-time profiles. The residual area extrapolated to infinity, determined as the final measured plasma concentration (C$_t$) divided by the terminal elimination rate constant (β), was added to AUC$_{0-t}$ to produce the total area under the curve (AUC$_{0-\infty}$). The results are also shown in TABLE 1. Ki values shown in the tables below were determined using Wang's equation (Wang Z X., An Exact Mathematical Expression For Describing Competitive Binding Of Two Different Ligands To A Protein Molecule. *FEBS Lett.* 1995; 360:111-4)).

TABLE 1

| Ex. | Target Binding Affinity | | NCI-H146 Cellular Efficacy | Pharmacokinetic area under the plasma concentration Curve (rat) | PK/PD ratio |
|---|---|---|---|---|---|
| | Ki (Bcl-2) | Ki (Bcl-X$_L$) | EC$_{50}$ | AUC$_{0-\infty}$ | AUC/EC$_{50}$ |
| 1 | ≤0.001 μM | ≤0.001 μM | 0.0891 μM | 5.01 μM | 56 |
| 2 | ≤0.001 μM | ≤0.001 μM | 0.0291 μM | 7.01 μM | 241 |
| 3 | ≤0.001 μM | ≤0.001 μM | 0.0288 μM | 4.13 μM | 144 |
| 4 | ≤0.001 μM | ≤0.001 μM | 0.0587 μM | 6.34 μM | 108 |
| 5 | ≤0.001 μM | ≤0.001 μM | 0.0388 μM | 2.22 μM | 57 |
| 6 | ≤0.001 μM | ≤0.001 μM | 0.0010 μM | 0.91 μM | 91 |
| 7 | ≤0.001 μM | ≤0.001 μM | 0.0589 μM | 3.87 μM | 66 |
| 8 | ≤0.001 μM | ≤0.001 μM | 0.0212 μM | 1.10 μM | 52 |
| 9 | ≤0.001 μM | ≤0.001 μM | 0.0137 μM | 1.88 μM | 137 |
| 10 | ≤0.001 μM | ≤0.001 μM | 0.0342 μM | 2.48 μM | 73 |
| 11 | ≤0.002 μM | ≤0.003 μM | 0.0206 μM | 2.40 μM | 117 |
| 12 | ≤0.001 μM | ≤0.001 μM | 0.0271 μM | 2.07 μM | 76 |
| 13 | ≤0.001 μM | ≤0.001 μM | 0.0190 μM | 2.06 μM | 108 |
| 14 | ≤0.001 μM | ≤0.001 μM | 0.0309 μM | 3.42 μM | 111 |
| 15 | ≤0.001 μM | ≤0.001 μM | 0.0099 μM | 1.25 μM | 126 |
| 16 | ≤0.002 μM | ≤0.002 μM | 0.0374 μM | 2.37 μM | 63 |
| 17 | ≤0.001 μM | ≤0.001 μM | 0.0287 μM | 0.88 μM | 31 |
| 18 | ≤0.001 μM | ≤0.001 μM | 0.0154 μM | 0.61 μM | 40 |
| 19 | ≤0.001 μM | ≤0.001 μM | 0.0158 μM | 7.12 μM | 451 |
| 20 | ≤0.001 μM | ≤0.001 μM | 0.0277 μM | 3.11 μM | 112 |
| 21 | ≤0.001 μM | ≤0.001 μM | 0.0643 μM | 1.81 μM | 28 |
| 22 | ≤0.001 μM | ≤0.001 μM | 0.0388 μM | 4.08 μM | 105 |
| 23 | ≤0.001 μM | ≤0.001 μM | 0.0528 μM | 3.54 μM | 67 |
| 24 | ≤0.001 μM | ≤0.001 μM | 0.0443 μM | 8.04 μM | 181 |
| 25 | ≤0.001 μM | ≤0.001 μM | 0.0164 μM | 1.67 μM | 102 |
| 26 | ≤0.001 μM | ≤0.001 μM | 0.0243 μM | 0.80 μM | 33 |
| 27 | ≤0.001 μM | ≤0.001 μM | 0.0185 μM | 2.08 μM | 112 |
| 28 | ≤0.001 μM | ≤0.001 μM | 0.0242 μM | 6.30 μM | 260 |
| 29 | ≤0.001 μM | ≤0.001 μM | 0.0298 μM | 1.74 μM | 58 |
| 30 | ≤0.001 μM | ≤0.001 μM | 0.0317 μM | 3.39 μM | 107 |
| 31 | ≤0.001 μM | ≤0.001 μM | 0.0130 μM | 5.10 μM | 392 |
| 32 | ≤0.001 μM | ≤0.001 μM | 0.0187 μM | 1.38 μM | 73.9 |

TABLE 1-continued

| | Target Binding Affinity | | NCI-H146 Cellular Efficacy | Pharmacokinetic area under the plasma concentration Curve (rat) | PK/PD ratio |
|---|---|---|---|---|---|
| Ex. | Ki (Bcl-2) | Ki (Bcl-$X_L$) | $EC_{50}$ | $AUC_{0-\infty}$ | $AUC/EC_{50}$ |
| 33 | ≤0.001 µM | ≤0.001 µM | 0.0378 µM | 3.01 µM | 79.8 |
| 34 | ≤0.001 µM | ≤0.001 µM | 0.0200 µM | 11.07 µM | 554 |
| 35 | ≤0.001 µM | ≤0.001 µM | 0.0076 µM | 1.26 µM | 166 |
| 36 | ≤0.001 µM | ≤0.001 µM | 0.0242 µM | 4.22 µM | 174 |
| 37 | ≤0.001 µM | ≤0.001 µM | 0.0175 µM | 7.30 µM | 417 |
| 38 | ≤0.001 µM | ≤0.001 µM | 0.0394 µM | 0.67 µM | 17 |
| 39 | ≤0.001 µM | ≤0.001 µM | 0.0827 µM | 1.66 µM | 20 |

The compounds of the present disclosure were compared to compounds disclosed in WO 2005/049594, identified herein as EXAMPLES A-L, by determining the ratio of systemic exposure to cellular efficacy. This measure, sometimes reported as $AUC/EC_{50}$, is well known to those skilled in the art of pharmaceutical drug discovery and drug development as a useful pharmacodynamic predictor of oral efficacy.

The examples of the present disclosure and compounds disclosed in WO 2005/049594 were both tested in an H146 cellular assay and evaluated for oral pharmacokinetic properties in rat, both as previously described herein. The results are shown in TABLES 2 and 3. As can be seen with reference to the data, the compounds of the present disclosure have a more preferred pharmacodynamic profile (meaning that the compounds of the present invention exhibit higher $AUC/EC_{50}$ values) as compared to the compounds known in the art. From these results, a number of observations can be drawn. It can be observed that the compounds having a $NO_2$ moiety at position $W^1$ tend to have good to excellent cellular potency (e.g., $EC_{50}<1$ µM). However, when the pharmacokinetic properties of these same compounds are determined, it can be seen that the systemic exposure after oral administration is poor, resulting in $AUC/EC_{50}$ ratios of from 0.5 to 19.7. On the other hand, when compounds having a $CF_3$ or CN moiety at position $W^1$ are tested in the cellular assay, these derivatives have relatively poor cellular efficacy (e.g., $EC_{50}>1$ µM) even though they have suitable systemic exposure after oral administration. Again, this combination provides overall $AUC/EC_{50}$ ratios from about 2.8 to about <7.4. Surprisingly, compounds of the present disclosure demonstrate cellular efficacy on par with compounds having an $NO_2$ moiety while maintaining suitable systemic exposure after oral administration. The resulting $AUC/EC_{50}$ ratios for the compounds of the disclosure are from about 20 to about 554.

TABLE 2

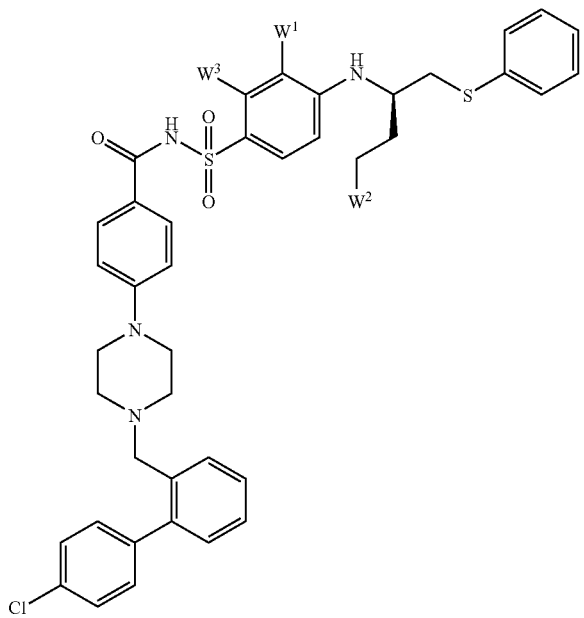

| EXAMPLE | $W^1$ | $W^2$ | $W^3$ | NCI-H146 Cellular Efficacy H146, $EC_{50}$, (µM) | Pharmacokinetic peak plasma concentration (rat) $C_{max}$, (µM) | Pharmacokinetic area under the plasma concentration curve (rat) AUC, (µM) | PK/PD ratio $AUC/EC_{50}$ |
|---|---|---|---|---|---|---|---|
| 38 | $SO_2CF_3$ | $N(CH_3)_2$ | H | 0.039 | 0.072 | 0.665 | 16.9 |
| A | $CF_3$ | $N(CH_3)_2$ | H | 1.599 | 0.371 | 4.412 | 2.8 |
| B | $NO_2$ | $N(CH_3)_2$ | H | 0.063 | 0.039 | 0.283 | 4.5 |

TABLE 2-continued
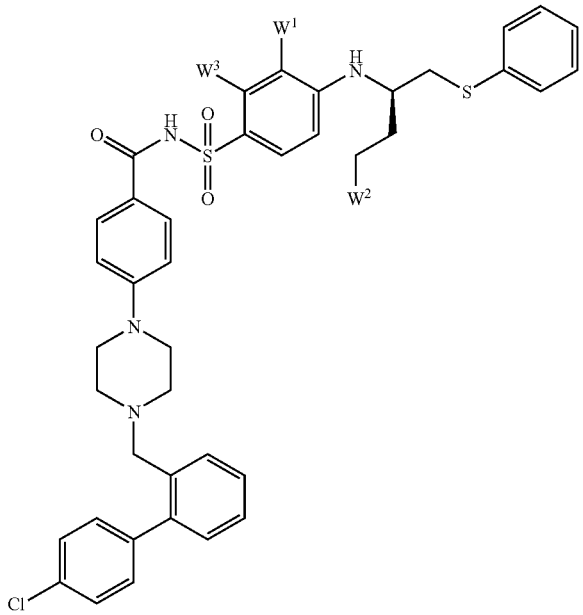
| EXAMPLE | $W^1$ | $W^2$ | $W^3$ | NCI-H146 Cellular Efficacy H146, $EC_{50}$, (μM) | Pharmacokinetic peak plasma concentration (rat) $C_{max}$, (μM) | Pharmacokinetic area under the plasma concentration curve (rat) AUC, (μM) | PK/PD ratio $AUC/EC_{50}$ |
|---|---|---|---|---|---|---|---|
| C | CN | $N(CH_3)_2$ | H | 1.807 | 0.315 | 1.917 | 1.1 |
| D | $CF_3$ | $N(CH_3)_2$ | F | 7.329 | 0.386 | 3.827 | 0.5 |
| 39 | $SO_2CF_3$ | ![morpholine] | H | 0.083 | 0.290 | 1.657 | 20.0 |
| E | $NO_2$ | ![morpholine] | H | 0.974 | 0.195 | 1.157 | 1.2 |
| F | $CF_3$ | ![morpholine] | H | >1.00 | 0.592 | 7.365 | <7.4 |

TABLE 3

[Structure of parent compound with W¹ on aromatic ring and W² as substituent on aminobutyl chain, featuring sulfonamide-benzamide-piperazine-methylene-cyclohexenyl-(4-chlorophenyl) scaffold with phenylthio group]

| EXAMPLE | W¹ | W² | NCI-H146 Cellular Efficacy H146 EC₅₀, (μM) | Pharmacokinetic peak plasma concentration (rat) C$_{max}$, (μM) | Pharmacokinetic area under the plasma concentration Curve (rat) AUC, (μM) | PK/PD ratio AUC/EC₅₀ |
|---|---|---|---|---|---|---|
| 18 | SO₂CF₂Cl | N(CH₃)₂ | 0.015 | 0.059 | 0.609 | 39.5 |
| 26 | SO₂CF₃ | N(CH₃)₂ | 0.024 | 0.097 | 0.803 | 33.0 |
| G | NO₂ | N(CH₃)₂ | 0.026 | 0.057 | 0.507 | 19.7 |
| H | CF₃ | N(CH₃)₂ | 0.410 | 0.215 | 1.973 | 4.8 |
| 3 | SO₂CF₂Cl | morpholin-4-yl | 0.029 | 0.385 | 4.131 | 143.6 |
| 7 | SO₂CF₃ | morpholin-4-yl | 0.059 | 0.518 | 3.867 | 65.6 |
| I | NO₂ | morpholin-4-yl | 0.094 | 0.267 | 1.977 | 21.0 |
| 6 | SO₂CF₂Cl | 2-oxa-5-azabicyclo[2.2.1]heptan-5-yl | 0.010 | 0.113 | 0.913 | 91.6 |
| 9 | SO₂CF₃ | 2-oxa-5-azabicyclo[2.2.1]heptan-5-yl | 0.014 | 0.156 | 1.878 | 137.5 |
| J | NO₂ | 2-oxa-5-azabicyclo[2.2.1]heptan-5-yl | 0.028 | 0.047 | 0.402 | 14.3 |
| 8 | SO₂CF₃ | 8-methyl-8-azabicyclo[3.2.1]octan-3-yl | 0.021 | 0.071 | 1.098 | 51.7 |

TABLE 3-continued

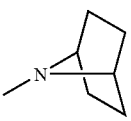

| EXAMPLE | W¹ | W² | NCI-H146 Cellular Efficacy H146 EC$_{50}$, (μM) | Pharmacokinetic peak plasma concentration (rat) C$_{max}$, (μM) | Pharmacokinetic area under the plasma concentration Curve (rat) AUC, (μM) | PK/PD ratio AUC/EC$_{50}$ |
|---|---|---|---|---|---|---|
| K | NO$_2$ | (bicyclic N-methyl group) | 0.049 | 0.077 | 0.368 | 7.5 |
| 33 | SO$_2$CF$_3$ | N(i-Pr)CH$_3$ | 0.038 | 0.129 | 3.013 | 79.8 |
| L | NO$_2$ | N(i-Pr)CH$_3$ | 0.034 | 0.0367 | 0.615 | 18.2 | i-Pr means iso-propyl

As shown in FIGS. 1-7, studies pertaining to the oral efficacy of EXAMPLE 1 in combination with etoposide, vincristine, CHOP, rituximab, rituximab with CHOP, rapamycin, and VELCADE demonstrated that EXAMPLE 1 synergistically enhanced efficacy of these cytotoxic agents during combination therapy when administered orally.

Further, combinations comprising EXAMPLE 1 and vincristine resulted in 10% complete tumor regression.

Still further, combinations comprising EXAMPLE 1 and rituximab resulted in 70% complete tumor regression whereas no tumor regressions were observed for rituximab alone.

Still further, combinations comprising EXAMPLE 1 and rapamycin resulted in 70% complete tumor regression whereas 10% tumor regressions were observed for rapamycin alone.

Still further, combinations comprising EXAMPLE 1 and rituximab with CHOP resulted in 90% complete tumor regression whereas 10% tumor regressions were observed for rituximab with CHOP only.

Still further, combinations comprising EXAMPLE 1 and bortexomib resulted in 10% complete tumor regression whereas no tumor regressions were observed for bortexomib alone.

Diseases during which anti-apoptotic Bcl-X$_L$ protein, anti-apoptotic Bcl-2 protein, anti-apoptotic Bcl-w protein or a combination thereof, are expressed include, but are not limited to, cancer and autoimmune disorders, wherein cancer includes, but is not limited to, acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute t-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, heavy chain disease, hemangioblastoma, hepatoma, hepatocellular cancer, hormone insensitive prostate cancer, leiomyosarcoma, liposarcoma, lung carcinoma, lymphangioendotheliosarcoma, lymphangiosarcoma, lymphoblastic leukemia, lymphoma (Hodgkin's and non- Hodgkin's), malignancies and hyperproliferative disorders of the bladder, breast, colon, lung, ovaries, pancreas, prostate, skin and uterus, lymphoid malignancies of T-cell or B-cell origin, leukemia, lymphoma, medullary carcinoma, medulloblastoma, melanoma, meningioma, mesothelioma, multiple myeloma, myelogenous leukemia, myeloma, myxosarcoma, neuroblastoma, non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, renal cell carcinoma, retinoblastoma, rhabdomyosarcoma, sarcoma, sebaceous gland carcinoma, seminoma, small cell lung carcinoma, solid tumors (carcinomas and sarcomas), small cell lung cancer squamous cell carcinoma, synovioma, sweat gland carcinoma, Waldenström's macroglobulinemia, testicular tumors, uterine cancer and Wilms' tumor (*Cancer Res.*, 2000, 60, 6101-10 and *Medicine*, 2d Ed., J.B. Lippincott Co., Philadelphia (1985)); autoimmune disorders include, but are not limited to, acquired immunodeficiency disease syndrome, autoimmune lymphoproliferative syndrome, hemolytic anemia, inflammatory diseases, and thrombocytopenia (*Current Allergy and Asthma Reports* 2003, 3:378-384; *Br. J. Haematol.* 2000 September; 110(3): 584-90; Blood 2000 Feb. 15; 95(4):1283-92; and *New England Journal of Medicine* 2004 September; 351(14): 1409-1418).

It is also expected that compounds having formula (II) would inhibit the growth of cells derived from a cancer or neoplasm such as breast cancer (including estrogen-receptor positive breast cancer), colorectal cancer, endometrial cancer, lung cancer (including small cell lung cancer), lymphoma (including follicular or Diffuse Large B-cell), lymphoma (including non-Hodgkin's lymphoma), neuroblastoma, ovarian cancer, prostate cancer (including hormone-insensitive prostate cancer), testicular cancer (including germ cell testicular cancer).

It is also expected that compounds having formula (II) would inhibit the growth of cells derived from a pediatric cancer or neoplasm such as embryonal rhabdomyosarcoma, pediatric acute lymphoblastic leukemia, pediatric acute myelogenous leukemia, pediatric alveolar rhabdomyosarcoma, pediatric anaplastic ependymoma, pediatric anaplastic large cell lymphoma, pediatric anaplastic medulloblastoma, pediatric atypical teratoid/rhabdoid tumor of the central nervous system, pediatric biphenotypic acute leukemia, pediatric Burkitts lymphoma, pediatric cancers of Ewing's family of tumors such as primitive neuroectodermal rumors, pediatric diffuse anaplastic Wilm's tumor, pediatric favorable histology Wilm's tumor, pediatric glioblastoma, pediatric medulloblastoma, pediatric neuroblastoma, pediatric neuroblastoma-derived myelocytomatosis, pediatric pre-B-cell cancers (such as leukemia), pediatric osteosarcoma, pediatric rhabdoid kidney tumor, pediatric rhabdomyosarcoma, and pediatric T-cell cancers such as lymphoma and skin cancer (commonly-owned U.S. application Ser. No. 10/988,338), *Cancer Res.*, 2000, 60, 6101-10); autoimmune disorders include, but are not limited to, acquired immunodeficiency disease syndrome, autoimmune lymphoproliferative syndrome, hemolytic anemia, inflammatory diseases, and thrombocytopenia (*Current Allergy and Asthma Reports* 2003, 3:378-384; *Br. J. Haematol.* 2000 September; 110(3): 584-90; Blood 2000 Feb. 15; 95(4):1283-92; and *New England Journal of Medicine* 2004 September; 351(14): 1409-1418).

Compounds having formula (II) may be made by synthetic chemical processes, examples of which are shown hereinbelow. It is meant to be understood that the order of the steps in the processes may be varied, that reagents, solvents and reaction conditions may be substituted for those specifically mentioned, and that vulnerable moieties may be protected and deprotected, as necessary.

Protecting groups for C(O)OH moieties include, but are not limited to, acetoxymethyl, allyl, benzoylmethyl, benzyl, benzyloxymethyl, tert-butyl, tert-butyldiphenylsilyl, diphenylmethyl, cyclobutyl, cyclohexyl, cyclopentyl, cyclopropyl, diphenylmethylsilyl, ethyl, para-methoxybenzyl, methoxymethyl, methoxyethoxymethyl, methyl, methylthiomethyl, naphthyl, para-nitrobenzyl, phenyl, n-propyl, 2,2,2-trichloroethyl, triethylsilyl, 2-(trimethylsilyl)ethyl, 2-(trimethylsilyl)ethoxymethyl, triphenylmethyl and the like.

Protecting groups for C(O) and C(O)H moieties include, but are not limited to, 1,3-dioxylketal, diethylketal, dimethylketal, 1,3-dithianylketal, O-methyloxime, O-phenyloxime and the like.

Protecting groups for NH moieties include, but are not limited to, acetyl, alanyl, benzoyl, benzyl(phenylmethyl), benzylidene, benzyloxycarbonyl (Cbz), tert-butoxycarbonyl (Boc), 3,4-dimethoxybenzyloxycarbonyl, diphenylmethyl, diphenylphosphoryl, formyl, methanesulfonyl, para-methoxybenzyloxycarbonyl, phenylacetyl, phthaloyl, succinyl, trichloroethoxycarbonyl, triethylsilyl, trifluoroacetyl, trimethylsilyl, triphenylmethyl, triphenylsilyl, para-toluenesulfonyl and the like.

Protecting groups for OH and SH moieties include, but are not limited to, acetyl, allyl, allyloxycarbonyl, benzyloxycarbonyl (Cbz), benzoyl, benzyl, tert-butyl, tert-butyldimethylsilyl, tert-butyldiphenylsilyl, 3,4-dimethoxybenzyl, 3,4-dimethoxybenzyloxycarbonyl, 1,1-dimethyl-2-propenyl, diphenylmethyl, formyl, methanesulfonyl, methoxyacetyl, 4-methoxybenzyloxycarbonyl, para-methoxybenzyl, methoxycarbonyl, methyl, para-toluenesulfonyl, 2,2,2-trichloroethoxycarbonyl, 2,2,2-trichloroethyl, triethylsilyl, trifluoroacetyl, 2-(trimethylsilyl)ethoxycarbonyl, 2-trimethylsilylethyl, triphenylmethyl, 2-(triphenylphosphonio)ethoxycarbonyl and the like.

The following abbreviations have the meanings indicated. ADDP means 1,1'-(azodicarbonyl)dipiperidine; AD-mix-β means a mixture of $(DHQD)_2PHAL$, $K_3Fe(CN)_6$, $K_2CO_3$ and $K_2SO_4$); AIBN means 2,2'-azobis(2-methylpropionitrile); 9-BBN means 9-borabicyclo[3.3.1]nonane; $(DHQD)_2PHAL$ means hydroquinidine 1,4-phthalazinediyl diethyl ether; DBU means 1,8-diazabicyclo[5.4.0]undec-7-ene; DIBAL means diisobutylaluminum hydride; DIEA means diisopropylethylamine; DMAP means N,N-dimethylaminopyridine; DME means 1,2-dimethoxyethane; DMF means N,N-dimethylformamide; dmpe means 1,2-bis(dimethylphosphino)ethane; DMSO means dimethylsulfoxide; dppb means 1,4-bis(diphenylphosphino)butane; dppe means 1,2-bis(diphenylphosphino)ethane; dppf means 1,1'-bis(diphenylphosphino)ferrocene; dppm means 1,1-bis(diphenylphosphino)methane; EDAC means 1-(3-dimethylaminopropyl)-3-ethylcarbodiimide; Fmoc means fluorenylmethoxycarbonyl; HATU means O-(7-azabenzotriazol-1-yl)-N,N'N'N'-tetramethyluronium hexafluorophosphate; HMPA means hexamethylphosphoramide; IPA means isopropyl alcohol; LDA means lithium diisopropylamide; LHMDS means lithium bis(hexamethyldisilylamide); MP-$BH_3$ means macroporous triethylammonium methylpolystyrene cyanoborohydride; LAH means lithium aluminum hydride; NCS means N-chlorosuccinimide; PyBOP means benzotriazol-1-yloxytripyrrolidinophosphonium hexafluorophosphate; TDA-1 means tris(2-(2-methoxyethoxy)ethyl)amine; TEA means triethylamine; TFA means trifluoroacetic acid; THF means tetrahydrofuran; NCS means N-chlorosuccinimide; NMM means N-methylmorpholine; NMP means N-methylpyrrolidine; PPh₃ means triphenylphosphine.

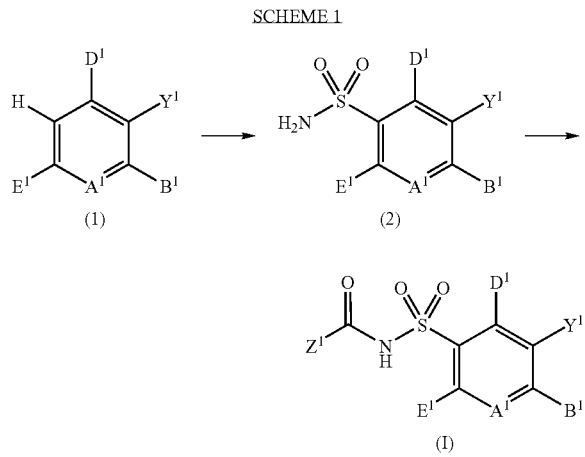

As shown in SCHEME 1, compounds having formula (1) may be converted to compounds having formula (2) by reacting the former, chlorosulfonic acid, and ammonia.

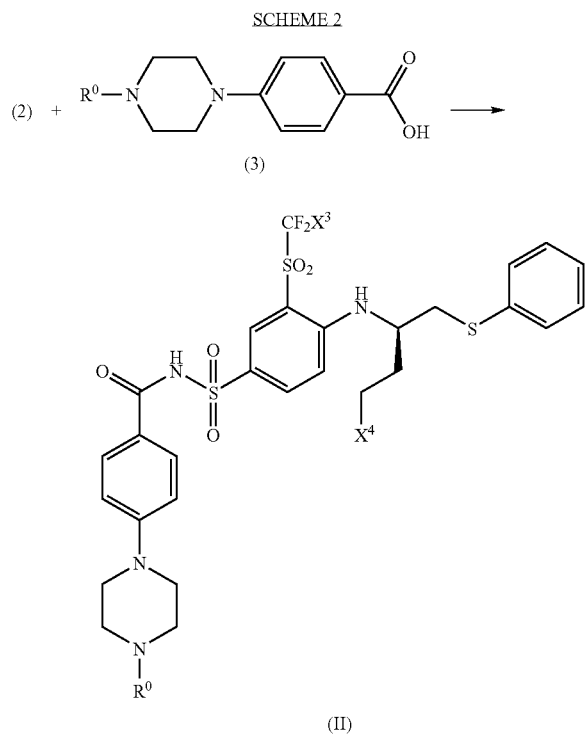

Compounds having formula (2) may be converted to compounds having formula (II) by reacting the former and compounds having formula (3) and a coupling agent, with or without a base. Examples of coupling agents include EDCI, CDI, and PyBop. Examples of bases include TEA, DIEA, DMAP, and mixtures thereof.

Compounds having formula (2) may be converted to compounds having formula (II) by reacting the former and compounds having formula $Z^1$—COCl and the base.

C. Synergistic Combinations of Polyploidy Inducing Agents and Bcl-2 Family Protein Inhibitors for Use in Treating Cancer In another aspect, the present disclosure relates to the discovery of synergistic combinations of therapeutic agents that are useful in treating patients suffering from cancer. As mentioned previously herein, the inventors of the present disclosure discovered that the induction of polyploidization in certain tumor and cancer cells makes or renders the survival of these resulting polyploid cells dependent on the anti-apoptotic activity of Bcl-$X_L$. Because these polyploid cells now dependent on Bcl-$X_L$ for their survival, these tumor and cancer cells are sensitized to Bcl-$X_L$ inhibition.

Thus, the present disclosure relates to a combination of therapeutic agents (namely, a combination therapy) that comprise (1) at least one polyploidy inducing agent; and (2) at least one Bcl-2 family protein inhibitor. The at least one polyploidy inducing agent can be an Aurora Kinase inhibitor (such as an Aurora Kinase B inhibitor), a microtubule inhibitor (such as, for example, Taxotere, vincristine, nocodazole, paclitaxel or colcemid), a pan-kinase inhibitor (such as, for example, staurosporine), an oncolytic virus (such as, for example, ONYX-015), Acridine orange, Dolastain-10, Noscapine, a toposiomerase II inhibitor (such as, for example, ICRF-187 or ICRF-193), 2-{4-[(7-chloro-2-quinoxalinyl)oxy]phenoxy}propionic acid, 2-{4-[(7-bromo-2-quinolinyl)oxy]phenoxy}propionic acid, Platycodin D, a microtubule poison (such as, for example, JG-03-14), an actin polymerization inhibitor (such as, for example, Cytochalasin B), Bistramide A or an antitumor antibiotic (such as, for example, Mithramycin SKI). An exemplary polyploidy inducing agent is an Aurora Kinase inhibitor. An exemplary Aurora Kinase inhibitor that can be used is an Aurora Kinase B inhibitor. Examples of Aurora Kinase B inhibitors that can be used include, but are not limited to, AZD1152, ZM447439, VX-680/MK0457 and Hesperadin. An exemplary Aurora Kinase B inhibitor that can be used is AZD1152.

Methods for determining the induction or evidence of polyploidy in one or more cells can obtained or determined using routine techniques known in the art. For example, evidence of polyploidy can be determined by detected elevated expression of p53. p53 is a surrogate for polyploidization in cells harboring wildtype p53 (See, Gizatullin, F. et al., "The Aurora Kinase inhibitor VX-680 induces endoreduplication and apoptosis preferentially in cells with compromised p53-dependent postmitotic checkpoint function," *Cancer Res.* 66, 7668-77. (2006)). Additionally, cells in which polyploidy has been induced exhibit a >4N DNA content, gross morphological increase in cell size and multinucleation, all of which can be detected using routine techniques known in the art.

The at least one Bcl-2 family member inhibitor can be any of the compounds described in Section B herein (such as, for example, ABT-263), ABT-737, Bcl-$X_L$ inhibitors (such as A-1113567 and A-1182848) and combinations thereof. An exemplary Bcl-2 family member inhibitor is ABT-263.

The aforementioned combination of therapeutic agents, namely, the at least one polyploidy agent and the at least one Bcl-2 family protein inhibitor, can be used to treat a patient suffering from at least one type of cancer. Specifically, such treatment methods involve administering a therapeutically effective amount of at least one polyploidy inducing agent and a therapeutically effective amount of at least one Bcl-2 family protein inhibitor to a patient suffering from cancer and in need of treatment thereof. The order in which the at least one polyploidy inducing agent and the at least one Bcl-2 family protein inhibitor are administered to the patient is not critical. However, because tumor and cancer cells do not become sensitized to Bcl-2 family protein inhibitors until after the induction of polyploidy, it is most beneficial to administer the therapeutically effective amount at least one polyploidy inducing agent to the patient prior to or subsequently with the therapeutically effective amount of at least one Bcl-2 family protein inhibitor.

The therapeutically effective amount of the at least one polyploidy inducing agent and the therapeutically effective amount of the at least one Bcl-2 family protein inhibitor to be administered the patient being treated with the combination of therapeutic agents described herein can be readily determined by those skilled in the art, namely, the treating physician.

An exemplary combination of therapeutic agents for use in treating a patient suffering from cancer involves the use of a therapeutically effective amount of AZD 1152 as the polyploidy inducing agent and a therapeutically effective amount of ABT-263 as the Bcl-2 family protein inhibitor.

The aforementioned described combinations of therapeutic agents can be administered to a patient suffering from any type of tumor, cancer, malignancy or combinations thereof. For example, the combination of therapeutic agents can be used to treat a patient suffering from acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute t-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, heavy chain disease, hemangioblastoma, hepatoma, hepatocellular cancer, hormone insensitive prostate cancer, leiomyosarcoma, liposarcoma, lung carcinoma, lymphangioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, leukemia, lymphoma, medullary carcinoma, medulloblastoma, melanoma, meningioma, mesothelioma, multiple myeloma, myelogenous leukemia, myeloma, myxosarcoma, neuroblastoma, non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, renal cell carcinoma, retinoblastoma, rhabdomyosarcoma, sarcoma, sebaceous gland carcinoma, seminoma, small cell lung cancer, solid tumors (carcinomas and sarcomas), small cell lung cancer squamous cell carcinoma, synovioma, sweat gland carcinoma, Waldenström's macroglobulinemia, testicular tumors, uterine cancer and Wilms' tumor (Cancer Res., 2000, 60, 6101-10 and Medicine, 2d Ed., J.B. Lippincott Co., Philadelphia (1985)).

D. Polynucleotide Assays

In connection with the discovery described above in Section C, the inventors of the present disclosure also discovered that tumor and cancer cells (regardless of whether or not these cells have been induced to be polyploid or not) and which contain at least one mutation in (i) a human Bcl-2 pro-apoptotic encoding gene (such as a human BAX gene and a human BAK gene), (ii) a human NOXA gene, or (iii) a human Bcl-2 pro-apoptotic encoding gene (such as a human BAX gene and a human BAK gene) and a human NOXA gene are immune or exhibit resistance to treatment with a Bcl-2 family protein inhibitor after induction of polyploidy with at least one polyploidy inducing agent. In other words, polyploid tumor and cancer cells which contain at least one mutation in (i) a human Bcl-2 pro-apoptotic encoding gene (such as a human BAX gene and a human BAK gene), (ii) a human NOXA gene, or (iii) a human Bcl-2 pro-apoptotic encoding gene (such as a human BAX gene and a human BAK gene) and a human NOXA gene do not exhibit or experience apoptosis or cell death when simultaneously or subsequently treated with at least one Bcl-2 family protein inhibitor.

Thus, in view of this discovery, in another aspect, the present disclosure provides nucleic acid assay methods to detect the presence or absence of at least one mutation in (i) a human Bcl-2 pro-apoptotic encoding gene (such as a human BAX gene and a human BAK gene), (ii) a human NOXA gene, or (iii) a human Bcl-2 pro-apoptotic encoding gene (such as a human BAX gene and a human BAK gene) and a human NOXA gene by: (i) in situ hybridization assays to intact tissue or cellular samples, (ii) microarray hybridization assays to chromosomal DNA extracted from a tissue sample, and (iii) polymerase chain reaction (PCR) or other amplification assays to chromosomal DNA extracted from a tissue sample. Assays using synthetic analogs of nucleic acids, such as peptide nucleic acids, in any of these formats can also be used.

The assays of the disclosure are used to identify at least one mutation in (i) a human Bcl-2 pro-apoptotic encoding gene (such as a human BAX gene and a human BAK gene), (ii) a human NOXA gene, or (iii) a human Bcl-2 pro-apoptotic encoding gene (such as a human BAX gene and a human BAK gene) and a human NOXA gene for use in both predicting therapy response and for monitoring patient response to polyploidy inducing agent therapy, a Bcl-2 family protein inhibitor or a combination of polyploidy inducing agent therapy and a Bcl-2 family protein inhibitor. Assays for response prediction can be run before the administration of at least one polyploidy inducing agent (to induce polyploidy) or after induction of polyploidy but prior to the administration of at least one Bcl-2 family protein inhibitor, and patients that do not show or exhibit showing at least one mutation in (i) a human Bcl-2 pro-apoptotic encoding gene (such as a human BAX gene and a human BAK gene), (ii) a human NOXA gene, or (iii) a human Bcl-2 pro-apoptotic encoding gene (such as a human BAX gene and a human BAK gene) and a human NOXA gene would be considered eligible for therapy with a polyploidy inducing agent, a Bcl-2 family protein inhibitor or a combination of a polyploidy inducing agent and a Bcl-2 family protein inhibitor.

For monitoring patient response, the assay can be run at the initiation of therapy (namely at the time of administration of at least one polyploidy inducing agent or after administration of at least one polyploidy inducing agent but prior to the administration of at least one Bcl-2 family protein inhibitor) to establish the baseline levels of the mutation(s) in the tissue sample, for example, the percent of total cells or number of cells showing at least one mutation in the sample. The same tissue is then sampled and assayed and the amount or number of mutations are then compared to the baseline or predetermined level. Where the number of mutations remains the same or decrease, the therapy is likely being effective and can be continued. Where significant increase in mutations over baseline level occurs, the patient may not be responding or may have developed resistance to continued polyploidy inducing agent therapy, Bcl-2 family protein inhibitor therapy or a combination of polyploidy inducing agent therapy and Bcl-2 family protein inhibitor therapy.

The assays of the disclosure can be used with test samples obtained from a patient suffering from cancers such as, but not limited to, acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute t-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, heavy chain disease, hemangioblastoma, hepatoma, hepatocellular cancer, hormone insensitive prostate cancer, leiomyosarcoma, liposarcoma, lung carcinoma, lymphangioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, leukemia, lymphoma, medullary carcinoma, medulloblastoma, melanoma, meningioma, mesothelioma, multiple myeloma, myelogenous leukemia, myeloma, myxosarcoma, neuroblastoma, non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, renal cell carcinoma, retinoblastoma, rhabdomyosarcoma, sarcoma, sebaceous gland carcinoma, seminoma, small cell lung carcinoma, solid tumors (carcinomas and sarcomas), small cell lung cancer squamous cell carcinoma, synovioma, sweat gland carcinoma, Waldenström's macroglobulinemia, testicular tumors, uterine cancer and Wilms' tumor (*Cancer Res.*, 2000, 60, 6101-10).

The inventive assays are performed on any type of test sample, such as a patient tissue sample of any type or on a derivative thereof, including peripheral blood, tumor or suspected tumor tissues (including fresh frozen and fixed paraffin-embedded tissue), cell isolates such as circulating epithelial cells separated or identified in a blood sample, lymph node tissue, bone marrow and fine-needle aspirates.

The present disclosure comprises detection of the genomic biomarkers by hybridization assays using detectably labeled nucleic acid-based probes, such as deoxyribonucleic acid (DNA) probes or protein nucleic acid (PNA) probes, or unlabeled primers which are designed/selected to hybridize to a specific chromosomal target. The unlabeled primers are used in amplification assays, such as by polymerase chain reaction (PCR), in which after primer binding, a polymerase amplifies the target nucleic acid sequence for subsequent detection. The detection probes used in PCR or other amplification assays are preferably fluorescent, and still more preferably, detection probes useful in "real-time PCR". Fluorescent labels are also preferred for use in situ hybridization but other detectable labels commonly used in hybridization techniques, e.g., enzymatic, chromogenic and isotopic labels, can also be used. Useful probe labeling techniques are described in the literature (Fan, Y.-S. 2002. *Molecular cytogenetics: protocols and applications*. Humana Press, Totowa, N.J. xiv, p. 411, the contents of which are incorporated herein by reference). In detection of the genomic biomarkers by microarray analysis, these probe labeling techniques are applied to label a chromosomal DNA extracted from a patient sample, which is then hybridized to the microarray.

Preferably, in situ hybridization is used to detect the presence or absence of at least one mutation in (i) a human Bcl-2 pro-apoptotic encoding gene (such as a human BAX gene and a human BAK gene), (ii) a human NOXA gene, or (iii) a human Bcl-2 pro-apoptotic encoding gene (such as a human BAX gene and a human BAK gene) and a human NOXA gene. Exemplary genes for which the presence or absence of at least one mutation is detected is a human BAX gene, a human BAK gene, a human NOXA gene and any combinations thereof. Primer and probes can be made by one of skill in the art using routine techniques in the art or using probes such as those available in commercially available kits, such as the TAQMAN® Gene Expression Assays (Applied Biosystems, Foster City, Calif.) for detecting and/or determining expression of the BAX, BAK and NOXA genes. Examples of TAQMAN® Gene Expression Assays available from Applied Biosystems which can be used are shown below in Table 3.

TABLE 3

| Gene | Applied Biosystems TAQMAN ® Gene Expression Assay ID |
|---|---|
| BAX | Hs99999001_m1 |
| BAK | Hs00940250_g1 |
| NOXA | Hs00560402_m1 |

Probes for use in the in situ hybridization methods of the disclosure fall into two broad groups: chromosome enumeration probes, i.e., probes that hybridize to a chromosomal region, usually a repeat sequence region, and indicate the presence or absence of an entire chromosome; and locus specific probes, i.e., probes that hybridize to a specific locus on a chromosome and detect the presence or absence of a specific locus. Chromosome arm probes, i.e., probes that hybridize to a chromosomal region and indicate the presence or absence of an arm of a specific chromosome, can also be used. It is preferred to use a locus specific probe that can detect changes of the unique chromosomal DNA sequences at the interrogated locus, such as, for example, one or more of human BAX, BAK and NOXA loci. Methods for use of unique sequence probes for in situ hybridization are described in U.S. Pat. No. 5,447,841, the contents of which are incorporated herein by reference.

A chromosome enumeration probe can hybridize to a repetitive sequence, located either near or removed from a centromere, or can hybridize to a unique sequence located at any position on a chromosome. For example, a chromosome enumeration probe can hybridize with repetitive DNA associated with the centromere of a chromosome. Centromeres of primate chromosomes contain a complex family of long tandem repeats of DNA comprised of a monomer repeat length of about 171 base pairs, that are referred to as alpha-satellite DNA. Centromere fluorescent in situ hybridization probes to each of chromosomes 14 and 18 are commercially available from Abbott Molecular (Des Plaines, Ill.).

Exceptionally useful in situ hybridization probes are directly labeled fluorescent probes, such as described in U.S. Pat. No. 5,491,224, incorporated herein by reference. U.S. Pat. No. 5,491,224 also describes simultaneous FISH assays using more than one fluorescently labeled probe.

Useful locus specific probes can be produced in any manner and generally contain sequences to hybridize to a chromosomal DNA target sequence of about 10,000 to about 1,000,000 bases long. Preferably the probe hybridizes to a target stretch of chromosomal DNA at the target locus of at least 100,000 bases long to about 500,000 bases long and also includes unlabeled blocking nucleic acid in the probe mix, as disclosed in U.S. Pat. No. 5,756,696, the contents of which are herein incorporated by reference, to avoid non-specific binding of the probe. It is also possible to use unlabeled, synthesized oligomeric nucleic acid or peptide nucleic acid as the blocking nucleic acid. For targeting the particular gene locus, it is preferred that the probes include nucleic acid sequences that span the gene and thus hybridize to both sides of the entire genomic coding locus of the gene. The probes can be produced starting with human DNA-containing clones such as Bacterial Artificial Chromosomes (BAC's) or the like. BAC libraries for the human genome are available from Invitrogen (Carlsbad, Calif.) and can be investigated for identification of useful clones. It is preferred to use the University of California Santa Cruz Genome Browser to identify DNA sequences in the target locus. These DNA sequences can then be used to synthesize PCR primers to screen BAC libraries to identify useful clones. The clones can then be labeled by conventional nick translation methods and tested as in situ hybridization probes.

Examples of fluorophores that can be used in the in situ hybridization methods described herein are: 7-amino-4-methylcoumarin-3-acetic acid (AMCA); Texas Red™ (Molecular Probes, Inc., Eugene, Oreg.); 5-(and-6)-carboxy-X-rhodamine; lissamine rhodamine B; 5-(and-6)-carboxyfluorescein; fluorescein-5-isothiocyanate (FITC); 7-diethylaminocoumarin-3-carboxylic acid, tetramethylrhodamine-5-(and-6)-isothiocyanate; 5-(and-6)-carboxytetramethylrhodamine; 7-hydroxy-coumarin-3-carboxylic acid; 6-[fluorescein 5-(and-6)-carboxamido]hexanoic acid; N-(4,4-difluoro-5,7-dimethyl-4-bora-3a,4a diaza-3-indacenepropionic acid; eosin-5-isothiocyanate; erythrosine-5-isothiocyanate; 5-(and-6)-carboxyrhodamine 6G; and Cascade™ blue acetylazide (Molecular Probes; an Invitrogen brand).

Probes can be viewed with a fluorescence microscope and an appropriate filter for each fluorophore, or by using dual or triple band-pass filter sets to observe multiple fluorophores. See, for example, U.S. Pat. No. 5,776,688, the contents of which are incorporated herein by reference. Any suitable microscopic imaging method can be used to visualize the hybridized probes, including automated digital imaging systems. Alternatively, techniques such as flow cytometry can be used to examine the hybridization pattern of the chromosomal probes.

Although the cell-by-cell gene amplification analysis resulting from in situ hybridization is preferred, the genomic biomarkers can also be detected by quantitative PCR. In this embodiment, DNA is extracted from the tissue sample, and is then amplified by PCR using a pair of primers specific to at least one of (i) a human Bcl-2 pro-apoptotic encoding gene (such as a human BAX gene and a human BAK gene), (ii) a human BH3 encoding gene (such as a human BID gene, a human NOXA gene, a human PUMA gene, a human BIK gene, a human BIM gene and a human BAD gene), or (iii) a human Bcl-2 pro-apoptotic encoding gene (such as a human BAX gene and a human BAK gene) and in a human BH3 encoding gene (such as a human BID gene, a human NOXA gene, a human PUMA gene, a human BIK gene, a human BIM gene and a human BAD gene), or by multiplex PCR, using multiple pairs of primers. Any primer sequence for the biomarkers can be used. Examples of primers that can be used are shown below in Table 4. The presence of at least one mutation is then determined by comparison to a reference amplification standard.

TABLE 4

| SEQUENCE | GENE |
| --- | --- |
| sense: 5'-GATGGACGGGTCCGGAGA-3'; (SEQ ID NO: 1) antisense: 5'-CTCAGCCCATCTTCTTCCAG-3' (SEQ ID NO: 2) | BAX |
| sense: 5'-TGGTTATGGGATGGGTGAGG; (SEQ ID NO: 3) antisense: 5'-CTGCTTTTTCTCGCCCTTCC-3' (SEQ ID NO: 4) | BAK |
| sense: 5'-TCCGAGGTGCTCCAGTTGGAGGC-3'; (SEQ ID NO: 5) antisense: 5'-GCCCGGCCTGGGTCTTTCGC-3' (SEQ ID NO: 6) | NOXA |

Microarray-based copy number analysis can also be used. In this embodiment, the chromosomal DNA after extraction is labeled for hybridization to a microarray comprising a substrate having multiple immobilized unlabeled nucleic acid probes arrayed at probe densities up to several million probes per square centimeter of substrate surface. Multiple microarray formats exist and any of these can be used, in the present disclosure. Examples of microarrays that can be used are the Affymetrix GeneChip® Mapping 100K Set SNP Array (See Matsuzaki, H., et al., "Genotyping over 100,000 SNPs on a pair of oligonucleotide arrays," Nat. Methods. 1:109-11 (2004)); the Affymetrix GeneChip® Mapping 250K Assay Kits (such as the GeneChip® Human Mapping 250K Nsp Array or the GeneChip® Human Mapping 250K Sty Array) or the Affymetrix GeneChip® Mapping 500K Array Set, each of which is commercially available from Affymetrix, Inc., Santa Clara, Calif.), the Agilent Human Genome aCGH Microarray 44B (available from Agilent Technologies, Inc., Santa Clara, Calif.), Illumina microarrays (Illumina, Inc., San Diego, Calif.), Nimblegen aCGH microarrays (Nimblegen, Inc., Madison, Wis.), etc. When using an oligonucleotide microarray to detect amplifications, it is preferred to use a microarray that has probe sequences to more than three separate locations in the targeted region. Examples of probes that can be used in the microarray are shown in below Table 5

TABLE 5

| SEQUENCE | GENE | SEQ ID NO: |
| --- | --- | --- |
| CTTCAATTTTCAAATCAAACTGATC (SNP_A-1936181) | BAX | SEQ ID NO: 7 |
| TGAATGCTTTGATTTCCTCACGTTT (SNP_A-2237715) | BAK | SEQ ID NO: 8 |
| TTGCCTGAACATCTTGGACATTTTT (SNP_A-1815502) | NOXA | SEQ ID NO: 9 |

E. Detecting Expression mRNA

The level of gene expression for (i) a human Bcl-2 pro-apoptotic encoding gene (such as a human BAX gene and a human BAK gene), (ii) a human NOXA gene, or (iii) a human Bcl-2 pro-apoptotic encoding gene (such as a human BAX gene and a human BAK gene) and a human NOXA gene gene can be determined by assessing the amount of one or more mRNAs in the test sample. Methods of measuring mRNA in samples are known in the art. To measure mRNA levels, the cells in a test sample can be lysed, and the levels of mRNA in the lysates or in RNA purified or semi-purified from lysates can be measured by any variety of methods familiar to those in the art. Such methods include hybridization assays using detectably labeled DNA or RNA probes (i.e., Northern blotting) or quantitative or semi-quantitative RT-PCR methodologies using appropriate oligonucleotide primers. Alternatively, quantitative or semi-quantitative in situ hybridization assays can be carried out using, for example, tissue sections, or unlysed cell suspensions, and detectably labeled (e.g., fluorescent, or enzyme-labeled) DNA or RNA probes. Additional methods for quantifying mRNA include RNA protection assay (RPA), cDNA and oligonucleotide microarrays, representation difference analysis (RDA), differential display, EST sequence analysis, and serial analysis of gene expression (SAGE).

In suitable embodiments, PCR amplification is used to detect for at least one mutation in a (i) a human Bcl-2 pro-apoptotic encoding gene (such as a human BAX gene and a human BAK gene), (ii) a human NOXA gene, or (iii) a human Bcl-2 pro-apoptotic encoding gene (such as a human BAX gene and a human BAK gene) and a human NOXA gene in the test sample. Briefly, in PCR, two primer sequences are prepared that are complementary to regions on opposite complementary strands of the marker sequence, for example containing the sequences for (i) a human Bcl-2 pro-apoptotic encoding gene (such as a human BAX gene and a human BAK gene), (ii) a human NOXA gene, or (iii) a human Bcl-2 pro-apoptotic encoding gene (such as a human BAX gene and a human BAK gene) and a human NOXA gene. An excess of deoxynucleotide triphosphates are added to a reaction mixture along with a DNA polymerase, e.g., Taq polymerase. If the target sequence is present in a sample, the primers will bind to the sequence and the polymerase will cause the primers to be extended along the marker sequence by adding on nucleotides. By raising and lowering the temperature of the reaction mixture, the extended primers will dissociate from the marker to form reaction products, excess primers will bind to the marker and to the reaction products and the process is repeated, thereby generating amplification products. A reverse transcriptase PCR amplification procedure can be performed in order to quantify the amount of mRNA amplified.

Any suitable fragment of (i) a human Bcl-2 pro-apoptotic encoding gene (such as a human BAX gene and a human BAK gene), (ii) a human NOXA gene, or (iii) a human Bcl-2 pro-apoptotic encoding gene (such as a human BAX gene and a human BAK gene) and a human NOXA gene can be amplified and detected. Designing efficient primers for PCR is within the ordinary skill in the art. Typically, amplified fragments for detection are approximately 50 to 300 nucleotides in length.

Amplification products can be detected in several ways. Amplification products can be visualized by electrophoresis of the sample in a gel and then staining with a DNA binding dye, e.g., ethidium bromide. Alternatively, the amplification products can be integrally labeled with a radioactive or fluorescent nucleotide and then visualized using x-ray film or under the appropriate stimulating spectra.

Amplification can be also monitored using "real-time" methods. Real-time PCR allows for the detection and quantitation of a nucleic acid target. Typically, this approach to quantitative PCR utilizes a fluorescent dye, which can be a double-strand specific dye, such as SYBR GREEN®. Alternatively, other fluorescent dyes (e.g., FAM or HEX) can be conjugated to an oligonucleotide probe or a primer. Various instruments capable of performing real time PCR are known in the art and include, for example, the ABI PRISM® 7900 (Applied Biosystems) and LIGHTCYCLER® systems (Roche). The fluorescent signal generated at each cycle of PCR is proportional to the amount of PCR product. A plot of fluorescence versus cycle number is used to describe the kinetics of amplification and a fluorescence threshold level is used to define a fractional cycle number related to initial template concentration. When amplification is performed and detected on an instrument capable of reading fluorescence during thermal cycling, the intended PCR product from non-specific PCR products can be differentiated using melting analysis. By measuring the change in fluorescence while gradually increasing the temperature of the reaction subsequent to amplification and signal generation it can be possible to determine the Tm of the intended product(s) as well as that of the nonspecific product.

The methods can include amplifying multiple nucleic acids in sample, also known as "multiplex detection" or "multiplexing." Multiplex PCR" refers to PCR that involves adding more than one set of PCR primers to the reaction in order to detect and quantify multiple nucleic acids, including nucleic acids from one or more target gene markers. Furthermore, multiplexing with an internal control (e.g., 18S rRNA, GADPH, or actin) provides a control for the PCR without reaction.

F. Sample Processing and Assay Performance

As discussed previously herein, the test sample of the present disclosure can be a tissue sample. The tissue sample to be assayed by the methods of the present disclosure can comprise any type, including a peripheral blood sample, a tumor tissue or a suspected tumor tissue, a thin layer cytological sample, a fine-needle aspirate sample, a bone marrow sample, a lymph node sample, a urine sample, an ascites sample, a lavage sample, an esophageal brushing sample, a bladder or lung wash sample, a spinal fluid sample, a brain fluid sample, a ductal aspirate sample, a nipple discharge sample, a pleural effusion sample, a fresh frozen tissue sample, a paraffin embedded tissue sample or an extract or processed sample produced from any of a peripheral blood sample, a tumor tissue or a suspected tumor tissue, a thin layer cytological sample, a fine needle aspirate sample, a bone marrow sample, a lymph node sample, a urine sample, an ascites sample, a lavage sample, an esophageal brushing sample, a bladder or lung wash sample, a spinal fluid sample, a brain fluid sample, a ductal aspirate sample, a nipple discharge sample, a pleural effusion sample, a fresh frozen tissue sample or a paraffin embedded tissue sample. For example, a patient peripheral blood sample can be initially processed to extract an epithelial cell population, and this extract can then be assayed. A microdissection of the tissue sample to obtain a cellular sample enriched with suspected tumor cells can also be used. The preferred tissue samples for use herein are peripheral blood, tumor tissue or suspected tumor tissue, including fine needle aspirates, fresh frozen tissue and paraffin embedded tissue, and bone marrow.

The tissue sample can be processed by any desirable method for performing in situ hybridization or other nucleic acid assays. For the preferred in situ hybridization assays, a paraffin embedded tumor tissue sample or bone marrow sample is fixed on a glass microscope slide and deparaffinized with a solvent, typically xylene. Useful protocols for tissue deparaffinization and in situ hybridization are available from Abbott Molecular Inc. (Des Plaines, Ill.). Any suitable instrumentation or automation can be used in the performance of the inventive assays. PCR based assays can be performed on the m2000 instrument system (Abbott Molecular, Des Plaines, Ill.). Automated imaging can be used for the preferred fluorescent in situ hybridization assays.

In one embodiment, the sample comprises a peripheral blood sample from a patient which is processed to produce an extract of circulating tumor or cancer cells to be examined for the presence or absence of at least one mutation in (i) a human Bcl-2 pro-apoptotic encoding gene (such as a human BAX gene and a human BAK gene), (ii) a human NOXA gene, or (iii) a human Bcl-2 pro-apoptotic encoding gene (such as a human BAX gene and a human BAK gene) and a human NOXA gene. The circulating tumor cells can be separated by immunomagnetic separation technology such as that available from Immunicon (Huntingdon Valley, Pa.). The at least one mutation is determined for the circulating tumor cells is then compared to the baseline level or predetermined level of circulating tumor cells having a determination made of the presence or absence of one or more mutations determined at a previous point in time, such as at the start of therapy. Increases or the presence of at least one mutation compared to the baseline level or the predetermined level can indicate therapy failure.

Test samples can comprise any number of cells that is sufficient for a clinical diagnosis, and typically contain at least about 100 cells. In a typical FISH assay, the hybridization pattern is assessed in about 25-1,000 cells. Test samples are typically considered "test positive" when found to contain the gene amplification in a sufficient proportion of the sample. The number of cells identified with at least one mutation and used to classify a particular sample as positive, in general, varies with the number of cells in the sample. The number of cells used for a positive classification is also known as the cut-off value. Examples of cut-off values that can be used in the determinations include about 5, 25, 50, 100 and 250 cells, or 5%, 10%, 15%, 20%, 25%, 30%, 35%, 40%, 50% and 60% of cells in the sample population. As low as one cell can be sufficient to classify a sample as positive. In a typical paraffin embedded tissue sample, it is preferred to identify at least 30 cells as positive and more preferred to identify at least 20 cells as positive for having at least one mutation. For example, detection in a typical paraffin embedded colorectal carcinoma of 30 cells would be sufficient to classify the tissue as positive and eligible for treatment.

G. Kits

The present disclosure also contemplates a variety of kits. In one aspect, the kit contains at least the following two therapeutic agents: (1) at least polyploidy inducing agent; and (2) at least one Bcl-2 family protein inhibitor. In addition, the kit can optionally include instructions for use, namely, the administration of the at least two therapeutic agents to a patient suffering from cancer and need of treatment thereof. These instructions may be provided in paper form or in computer-readable form, such as a disc, CD, DVD or the like.

In another aspect, the kit of the present disclosure is a kit for detecting the presence or absence of at least one mutation in (i) a human Bcl-2 pro-apoptotic encoding gene (such as a human BAX gene and a human BAK gene), (ii) a human NOXA gene, or (iii) a human Bcl-2 pro-apoptotic encoding gene (such as a human BAX gene and a human BAK gene) and a human NOXA gene in a test sample. Exemplary genes for which the presence or absence of at least one mutation is detected using said kit is a human BAX gene, a human BAK gene, a human NOXA gene and any combinations thereof. Such kits can comprise one or more reagents for determining the presence or absence of the above described at least one mutation. For example, said kit can contain one or more nucleic acid probes. Alternatively, or in addition to the probes, the kit can contain one or more nucleic acid primers.

Thus, the present disclosure further provides for diagnostic and quality control kits comprising one or more nucleic acid primers, nucleic acid probes or nucleic acid primers and probes described herein. Optionally the assays, kits and kit components of the present disclosure can be optimized for use on commercial platforms (e.g., immunoassays on the PRISM®, AxSYM®, ARCHITECT® and EIA (Bead) platforms of Abbott Laboratories, Abbott Park, Ill., as well as other commercial and/or in vitro diagnostic assays). Additionally, the assays, kits and kit components can be employed in other formats, for example, on electrochemical or other hand-held or point-of-care assay systems. The present disclosure is, for example, applicable to the commercial Abbott Point of Care (i-STAT®, Abbott Laboratories, Abbott Park, Ill.) electrochemical immunoassay system that performs sandwich immunoassays for several cardiac markers, including TnI, CKMB and BNP. Immunosensors and methods of operating them in single-use test devices are described, for example, in U.S. Patent Application Publication Nos. 2003/0170881, 2004/0018577, 2005/0054078 and 2006/0160164, which are incorporated herein by reference. Additional background on the manufacture of electrochemical and other types of immunosensors is found in U.S. Pat. No. 5,063,081 which is also incorporated by reference for its teachings regarding same.

Optionally the kits include quality control reagents (e.g., sensitivity panels, calibrators, and positive controls). Preparation of quality control reagents is well known in the art, and is described, e.g., on a variety of immunodiagnostic product insert sheets.

The kit can incorporate a detectable label, such as a fluorophore, radioactive moiety, enzyme, biotin/avidin label, chromophore, chemiluminescent label, or the like, or the kit may include reagents for labeling the nucleic acid primers, the nucleic acid probes or the nucleic acid primers and nucleic acid probes for detecting the presence or absence of at least one mutation as described herein. The primers and/or probes, calibrators and/or controls can be provided in separate containers or pre-dispensed into an appropriate assay format, for example, into microtiter plates.

The kits can optionally include other reagents required to conduct a diagnostic assay or facilitate quality control evaluations, such as buffers, salts, enzymes, enzyme co-factors, substrates, detection reagents, and the like. Other components, such as buffers and solutions for the isolation and/or treatment of a test sample (e.g., pretreatment reagents), may also be included in the kit. The kit may additionally include one or more other controls. One or more of the components of the kit may be lyophilized and the kit may further comprise reagents suitable for the reconstitution of the lyophilized components.

The various components of the kit optionally are provided in suitable containers. As indicated above, one or more of the containers may be a microtiter plate. The kit further can include containers for holding or storing a sample (e.g., a container or cartridge for a blood or urine sample). Where appropriate, the kit may also optionally contain reaction vessels, mixing vessels and other components that facilitate the preparation of reagents or the test sample. The kit may also include one or more instruments for assisting with obtaining a test sample, such as a syringe, pipette, forceps, measured spoon, or the like.

The kit further can optionally include instructions for use, which may be provided in paper form or in computer-readable form, such as a disc, CD, DVD or the like.

H. Adaptation of Kits

The kit (or components thereof), as well as the method of determining the presence or absence of at least one mutation in (i) a human Bcl-2 pro-apoptotic encoding gene (such as a human BAX gene and a human BAK gene), (ii) a human NOXA gene, or (iii) a human Bcl-2 pro-apoptotic encoding gene (such as a human BAX gene and a human BAK gene) and a human NOXA gene using the components and methods described herein, can be adapted for use in a variety of automated and semi-automated systems (including those wherein the solid phase comprises a microparticle), as described, e.g., in U.S. Pat. Nos. 5,089,424 and 5,006,309, and as commercially marketed, e.g., by Abbott Laboratories (Abbott Park, Ill.) as ARCHITECT®.

Some of the differences between an automated or semi-automated system as compared to a non-automated system (e.g., ELISA) include the substrate to which the first specific binding partner (e.g., capture antibody) is attached (which can impact sandwich formation and analyte reactivity), and the length and timing of the capture, detection and/or any optional wash steps. Whereas a non-automated format such as an ELISA may require a relatively longer incubation time with sample and capture reagent (e.g., about 2 hours) an automated or semi-automated format (e.g., ARCHITECT®, Abbott Laboratories) may have a relatively shorter incubation time (e.g., approximately 18 minutes for ARCHITECT®). Similarly, whereas a non-automated format such as an ELISA may incubate a detection antibody such as the conjugate reagent for a relatively longer incubation time (e.g., about 2 hours), an automated or semi-automated format (e.g., ARCHITECT®) may have a relatively shorter incubation time (e.g., approximately 4 minutes for the ARCHITECT®).

Other platforms available from Abbott Laboratories include, but are not limited to, AxSYM®, IMx® (see, e.g., U.S. Pat. No. 5,294,404, which is hereby incorporated by reference in its entirety), PRISM®, EIA (bead), and Quantum™ II, as well as other platforms. Additionally, the assays, kits and kit components can be employed in other formats, for example, on electrochemical or other hand-held or point-of-care assay systems. The present disclosure is, for example, applicable to the commercial Abbott Point of Care (i-STAT®, Abbott Laboratories) electrochemical immunoassay system that performs sandwich immunoassays. Immunosensors and their methods of manufacture and operation in single-use test devices are described, for example in, U.S. Pat. No. 5,063,081, U.S. Patent Application Publication Nos. 2003/0170881, 2004/0018577, 2005/0054078, and 2006/0160164, which are incorporated in their entireties by reference for their teachings regarding same.

It further goes without saying that the methods and kits as described herein necessarily encompass other reagents and methods for carrying out the assays. For instance, encompassed are various buffers such as are known in the art and/or which can be readily prepared or optimized to be employed.

The following examples are presented to provide what is believed to be the most useful and readily understood description of procedures and conceptual aspects of this disclosure.

EXAMPLE 1A 3-(R)-((Carbobenzyloxy)amino)-γ-butyrolactone, prepared as described in J. Am. Chem. Soc. 1986, 108, 4943-4952, (62 g) and morpholine (46 mL) in dioxane (700 mL) at 65° C. was stirred for 24 hours, cooled and concentrated. The concentrate was chromatographed on silica gel with 10% methanol/ethyl acetate.

EXAMPLE 1B

EXAMPLE 1A (16.5 g), diphenyl disulfide (14.5 g) and tributylphosphine (16.6 mL) in toluene (250 mL) at 80° C. was stirred for 24 hours, cooled and concentrated. The concentrate was chromatographed on silica gel with 1:1 ethyl acetate/hexanes.

EXAMPLE 1C

EXAMPLE 1B (18 g) in 30% HBr in acetic acid (250 mL) at 25° C. was stirred for 24 hours, concentrated, poured into 1M HCl and extracted with diethyl ether. The extract was extracted with 1M HCl, and this extract was cooled to 0° C., adjusted to pH 12 with KOH and extracted with dichloromethane. The extract was washed with brine and dried ($Na_2SO_4$), filtered and concentrated.

EXAMPLE 1D

EXAMPLE 1C (45.4 g) in THF (500 mL) at 55° C. was treated with 1M $BH_3$.THF (650 mL) over 2 hours, stirred for 24 hours, cooled to 0° C., treated with methanol (80 mL), poured into methanol (500 mL) and concentrated. A mixture of the concentrate in methanol (400 mL) was treated with a HCl-saturated methanol (800 mL), refluxed for 24 hours, cooled, concentrated, poured into 2M NaOH and extracted with ethyl acetate. The extract was washed with 1M NaOH and brine and dried ($Na_2SO_4$), filtered and concentrated. The concentrate was chromatographed on silica gel with ethyl acetate 10% methanol/ethyl acetate and 10% methanol/10% acetonitrile/5% TEA/75% ethyl acetate.

EXAMPLE 1E

Methyl viologen hydrochloride (1.17 g) in DMF (80 mL) at 25° C. was saturated with trifluoromethyl iodide, treated with 2-fluorobenzenethiol (9.7 mL) and TEA (20 mL), stirred for 24 hours, diluted with water (240 mL) and extracted with diethyl ether. The extract was washed with 1M NaOH, saturated ammonium chloride and brine and concentrated.

EXAMPLE 1F

EXAMPLE 1E (17.346 g) in 1:1:2 carbon tetrachloride/acetonitrile/water (800 mL) at 25° C. was treated with sodium periodate (56.8 g) and ruthenium(III) chloride hydrate (183 mg), stirred for 18 hours, diluted with dichloromethane (100 mL) and filtered through diatomaceous earth (Celite®). The filtrate was washed with saturated sodium bicarbonate and extracted with dichloromethane. The extract was washed with brine and dried ($MgSO_4$), filtered and concentrated. The concentrate was filtered through silica gel.

EXAMPLE 1G

EXAMPLE 1F (37.3 g) in chlorosulfonic acid (32.8 mL) at 120° C. was stirred for 18 hours, cooled to 25° C. and pipetted onto crushed ice. The mixture was extracted with ethyl acetate, and the extract was washed with water and brine and dried (MgSO$_4$), filtered and concentrated.

EXAMPLE 1H

EXAMPLE 1G (23 g) in isopropanol (706 mL) at −78° C. was treated with ammonium hydroxide (98 mL) over 1 hour, stirred for 1 hour, quenched with 6M HCl (353 mL), warmed to 25° C. and concentrated. The concentrate was mixed with water and extracted with ethyl acetate. The extract was dried (MgSO$_4$), filtered and concentrated. The concentrate was recrystallized from ethyl acetate/hexane.

EXAMPLE 1I

EXAMPLE 1H (13.48 g) and EXAMPLE 1D (11.56 g) in THF (218 mL) was treated with DIEA (15.1 mL), stirred at 50° C. for 4 hours, cooled, treated with saturated sodium bicarbonate and extracted with ethyl acetate. The extract was dried (MgSO$_4$), filtered and concentrated. The concentrate was recrystallized from hexanes/ethyl acetate.

EXAMPLE 1J

DMF (10 mL) and chloroform (80 mL) at 3° C. was treated with PBr$_3$ (12 mL), stirred for 20 minutes at 25° C., treated with 4,4-dimethylcyclohexanone (7.15 g) in chloroform (50 mL), stirred for 18 hours, poured onto ice, neutralized with solid sodium bicarbonate and extracted with diethyl ether. The extract was washed with brine and dried (MgSO$_4$), filtered and concentrated. The concentrate was chromatographed on silica gel with 0-10% ethyl acetate/hexanes.

EXAMPLE 1K

EXAMPLE 1J (1.7 g) and 4-piperazin-1-ylbenzoic acid ethyl ester (1.9 g) in methanol (30 mL) was treated with sodium cyanoborohydride (0.6 g), adjusted to pH 5 with acetic acid, stirred for 18 hours and filtered through diatomaceous earth (Celite®). The filtrate was concentrated, and the concentrate was chromatographed on silica gel on silica gel with 10-30% ethyl acetate/hexanes.

EXAMPLE 1L

EXAMPLE 1K (1.1 g), 4-chlorophenylboronic acid (0.6 g), 2M Na$_2$CO$_3$ (2 mL) and PdCl$_2$(PPh$_3$)$_2$ (0.1 g) in 7:3:2 DME/water/ethanol (20 mL) was stirred at 85° C. for 18 hours, filtered through diatomaceous earth (Celite®) and concentrated. The concentrate was chromatographed on silica gel with 10-30% ethyl acetate/hexanes.

EXAMPLE 1M

EXAMPLE 1L (4.59 g) and LiOH (1.25 g) in dioxane (75 mL) and water (10 mL) was stirred at 100° C. for 18 hours, cooled to 25° C. and concentrated. The concentrate was dissolved in water, heated to reflux, neutralized with 1M HCl (28.5 mL), cooled to 25° C., filtered and concentrated.

EXAMPLE 1N

EXAMPLE 1M (31.5 g), EXAMPLE 1I (39.93 g), EDAC.HCl (20.60 g) and DMAP (13.15 g) in dichloromethane (500 mL) at 25° C. was stirred for 18 hours, diluted with dichloromethane, washed with saturated ammonium chloride and brine and dried (MgSO$_4$), filtered and concentrated. The concentrate was chromatographed on silica gel with 0-10% methanol/ammonia-saturated dichloromethane.
$^1$H NMR (300 MHz, DMSO-d$_6$) δ 8.12 (d, 1H), 7.94 (dd, 1H), 7.71 (d, 2H), 7.38 (d, 2H), 7.30 (m, 4H), 7.18 (m, 1H), 7.12 (d, 2H), 6.98 (d, 1H), 6.85 (d, 3H), 4.07 (m, 1H), 3.53 (br, 4H), 3.28 (m, 12H), 2.44 (m, 8H), 1.99 (m, 3H), 1.80 (m, 1H), 1.44 (t, 2H), 0.97 (s, 6H).

EXAMPLE 2A

Powdered NaOH (31.2 g), TDA-1 (5 mL) and 2-fluorobenzene thiol (33.6 mL) in benzene (400 mL) was saturated with chlorodifluoromethane, stirred at 80° C. for 30 minutes and filtered through diatomaceous earth (Celite®). The filtrate was washed with saturated NaHCO$_3$ and the water layer was extracted with diethyl ether. The extracts were combined and dried (MgSO$_4$), filtered and concentrated.

EXAMPLE 2B

EXAMPLE 2A (46 g) in 1:1:2 CCl$_4$/CH$_3$CN/water (1.2 L) at 25° C. was treated with NaIO$_4$ (165.6 g) and RuCl$_3$.xH$_2$O (534 mg), stirred for 18 hours, diluted with dichloromethane and filtered through diatomaceous earth (Celite®). The filtrate was washed with saturated NaHCO$_3$ and dried (Na$_2$SO$_4$), filtered and concentrated. The concentrate was filtered through silica gel.

EXAMPLE 2C

EXAMPLE 2B (25 g) and NCS (17.55 g) in THF (700 mL) at −78° C. was treated with LHMDS (178.5 mL) over 1 hour, stirred for 1 hour and quenched with ammonium chloride. The mixture was extracted with ethyl acetate, and the extract was washed with brine and dried (MgSO$_4$), filtered and concentrated. The concentrate was chromatographed on silica gel with 0-5% ethyl acetate/hexanes.

EXAMPLE 2D

EXAMPLE 2C (44 g) in chlorosulfonic acid (36.7 mL) at 120° C. was stirred for 18 hours, cooled to 25° C., pipetted onto crushed ice and extracted with ethyl acetate. The extract was washed with water and brine and dried (MgSO$_4$), filtered and concentrated.

EXAMPLE 2E

EXAMPLE 2D (22 g) in isopropanol (700 mL) at −78° C. was treated with aqueous ammonia (90 mL) over 1 hour, stirred for another hour, quenched with 6M HCl (300 mL), warmed to 25° C. and concentrated. The concentrate was mixed with water and extracted with ethyl acetate. The extract was dried (MgSO$_4$), filtered and concentrated. The concentrate was recrystallized from hexanes/ethyl acetate.

EXAMPLE 2F

EXAMPLE 2E (2.89 g) and EXAMPLE 1D (2.39 g) in THF (20 mL) was treated with diisopropylethylamine (3.2 mL), stirred at 60° C. for 18 hours, cooled, treated with saturated sodium bicarbonate and extracted with ethyl acetate. The extract was dried (MgSO$_4$), filtered and concentrated. The concentrate was chromatographed on silica gel with 1.5-5% 7M ammonia in methanol/dichloromethane.

EXAMPLE 2G

Hexane-washed 60% oily NaH (17 g) in dichloromethane (300 mL) at −5° C. was treated with 4,4-dimethyl-2-oxo-cyclohexanecarboxylic acid methyl ester, prepared as described in Tetrahedron (1992), 48 (21), 4459-64, (53.89 g), stirred for 30 minutes, cooled to −78° C., treated with trifluoromethanesulfonic anhydride, warmed to 25° C., stirred for 18 hours, washed with brine and dried (MgSO$_4$), filtered and concentrated.

EXAMPLE 2H

EXAMPLE 2G (86 g), 4-chlorophenylboronic acid (50 g), CsF (104 g) and tetrakis(triphenylphosphine)palladium(0) (2.5 g) in 2:1 DME/methanol (600 mL) at 70° C. was stirred for 18 hours and concentrated. The concentrate was dissolved in diethyl ether, and the solution was dried (MgSO$_4$), filtered and concentrated. The concentrate was filtered through silica gel with 20% ethyl acetate/hexanes.

EXAMPLE 2I

Lithium borohydride (18 g) was treated with EXAMPLE 2H (76 g) in diethyl ether (400 mL) and methanol (23 mL), stirred at reflux for 4 hours, cooled, quenched with 1M HCl, diluted with water and extracted with diethyl ether. The extract was dried (MgSO$_4$), filtered and concentrated. The concentrate was chromatographed on silica gel with 0-30% ethyl acetate/hexanes.

EXAMPLE 2J

EXAMPLE 2I (17.5 g) in dichloromethane (100 mL) at 0° C. was treated simultaneously with methanesulfonyl chloride (5.6 mL) and TEA (21 mL), stirred for 5 minutes, treated with 4-piperazin-1-ylbenzoic acid ethyl ester (17 g), stirred at 25° C. for 18 hours, washed with ammonium chloride and dried (Na$_2$SO$_4$), filtered and concentrated. The concentrate was chromatographed on silica gel with 10% ethyl acetate/hexanes.

EXAMPLE 2K

This example was prepared by substituting EXAMPLE 2J for EXAMPLE 1L in EXAMPLE 1M.

EXAMPLE 2L

EXAMPLE 2K (16.9 g) and EXAMPLE 2F (22 g) in dichloromethane (200 mL) at 25° C. was treated with EDAC.HCl (11.06 g) and DMAP (7.06 g), stirred for 18 hours, diluted with dichloromethane (400 mL), washed with saturated ammonium chloride and brine and dried (MgSO$_4$), filtered and concentrated. The concentrate was chromatographed on silica gel with 0-10% methanol/ammonia-saturated dichloromethane. $^1$H NMR (400 MHz, DMSO-d$_6$) δ 8.07 (d, 1H), 7.90 (dd, 1H), 7.71 (d, 2H), 7.36 (m, 4H), 7.29 (m, 2H), 7.20 (m, 1H), 7.09 (d, 2H), 6.86 (d, 1H), 6.80 (d, 2H), 6.76 (d, 1H), 4.02 (m, 1H), 3.50 (m, 4H), 3.33 (m, 2H), 3.16 (m, 4H), 2.81 (s, 2H), 2.29 (m, 12H), 1.99 (s, 2H), 1.94 (m, 1H), 1.71 (m, 1H), 1.42 (t, 2H), 0.96 (s, 6H).

EXAMPLE 3A

This example was prepared by substituting 2-bromo-cyclohex-1-enecarbaldehyde, prepared as described in Collect. Czech. Chem. Commun., 1961, 26, 3059.) for EXAMPLE 1J in EXAMPLE 1K.

EXAMPLE 3B

This example was prepared by substituting EXAMPLE 3A for EXAMPLE 1K in EXAMPLE 1L.

EXAMPLE 3C

This example was prepared by substituting EXAMPLE 3B for EXAMPLE 1L in EXAMPLE 1M.

EXAMPLE 3D

This example was prepared by substituting EXAMPLE 3C and EXAMPLE 2F for EXAMPLE 1M and EXAMPLE 1I, respectively, in EXAMPLE 1N. $^1$H NMR (400 MHz, DMSO-d$_6$) δ 8.11 (d, 1H), 7.92 (dd, 1H), 7.71 (d, 2H), 7.37 (d, 2H), 7.34 (m, 2H), 7.27 (t, 2H), 7.18 (t, 1H), 7.12 (d, 2H), 6.94 (d, 1H), 6.84 (m, 3H), 4.04 (m, 1H), 3.51 (br, 4H), 3.27 (br, 10H), 2.84 (br, 2H), 2.33 (br, 6H), 2.18 (br, 4H), 1.97 (m, 1H), 1.76 (m, 1H), 1.66 (s, 4H).

EXAMPLE 4A

A solution of 3-(R)-((carbobenzyloxy)amino)-γ-butyrolactone (prepared according to the procedure described in J. Am. Chem. Soc. 1986, 108, 4943-4952, 7.72 g, 32.8 mmol) in THF (100 mL) was saturated with gaseous dimethylamine, stirred at room temperature for 16 hours, and concentrated. The residue was filtered through a plug of silica gel eluting with 50% acetone in hexanes to give the desired product.

EXAMPLE 4B

A solution of EXAMPLE 4A (8.45 g, 30.14 mmol) in toluene (15 mL) was treated with tributylphosphine (9.76 mL, 39.20 mmol) and diphenyldisulfide (7.30 g, 39.20 mmol) and heated to 80° C. for 16 hours. The reaction mixture was concentrated and purified by column chromatography on silica gel eluting with a gradient of 0-50% ethyl acetate in hexanes to give the desired product.

EXAMPLE 4C

EXAMPLE 4B (7.5 g) and bis(cyclopentadienyl)zirconium(IV) chloride hydride (10.31 g) in THF (100 mL) at 25° C. was stirred for 20 minutes and concentrated. The concentrate was chromatographed on silica gel with 50% ethyl acetate in hexane.

EXAMPLE 4D

EXAMPLE 4C (2.87 g) and N-isopropylmethylamine (1.92 g) in 1,2-dichloroethane (50 mL) at 25° C. was treated with sodium triacetoxyborohydride (3 g), stirred for 2 hours, diluted with ethyl acetate, washed with 2M NaOH, water and brine and dried (Na$_2$SO$_4$), filtered and concentrated. The concentrate was chromatographed on silica gel with 1% methanol/dichloromethane.

EXAMPLE 4E

This example was prepared by substituting EXAMPLE 4D for EXAMPLE 1B in EXAMPLE 1C.

EXAMPLE 4F

This example was prepared by substituting EXAMPLE 4E for EXAMPLE 1D in EXAMPLE 11.

EXAMPLE 4G

This example was prepared by substituting EXAMPLE 4F for EXAMPLE 1I in EXAMPLE 1N. $^1$H NMR (400 MHz, DMSO-d$_6$) δ 8.08 (s, 1H), 7.98 (d, 1H), 7.71 (d, 2H), 7.37 (m, 4H), 7.28 (t, 2H), 7.20 (t, 1H), 7.12 (d, 2H), 6.89 (d, 1H), 6.78 (d, 2H), 6.70 (d, 1H), 4.01 (m, 1H), 3.13 (m, 6H), 2.75 (m, 2H), 2.28 (m, 6H), 2.04 (m, 4H), 1.99 (m, 2H), 1.43 (m, 2H), 1.12 (m, 10H), 0.97 (s, 6H).

EXAMPLE 5

This example was prepared by substituting 4-(4-(2-(4-chlorophenyl)cyclo-1-enylmethyl)piperazin-1-yl)benzoic acid, prepared as described in commonly-owned U.S. patent application Ser. No. 10/988,338, and EXAMPLE 4F for EXAMPLE 1M and EXAMPLE 1I, respectively, in EXAMPLE 1N. $^1$H NMR (400 MHz, DMSO-d$_6$) δ 9.00 (m, 1H), 8.09 (s, 1H), 7.98 (d, 1H), 7.71 (d, 2H), 7.36 (m, 4H), 7.30 (t, 2H), 7.20 (t, 1H), 7.09 (d, 2H), 6.90 (d, 1H), 6.78 (d, 2H), 6.65 (d, 1H), 4.00 (m, 2H), 3.13 (m, 4H), 2.78 (m, 2H), 2.55 (m, 2H), 2.40 (m, 4H), 2.31 (m, 4H), 2.00 (m, 3H), 1.79 (m, 4H), 1.58 (m, 4H), 1.51 (m, 2H), 1.12 (m, 6H).

EXAMPLE 6A

This example was prepared by substituting EXAMPLE 4B for EXAMPLE 1B in EXAMPLE 1C.

EXAMPLE 6B

EXAMPLE 6A (6.13 g) in THF (200 mL) at 25° C. was treated with di-tert-butyldicarbonate (7 g), stirred for 4 hours and concentrated. The concentrate was dissolved into ethyl acetate (500 mL), washed with 1M NaOH, water and brine and dried (Na$_2$SO$_4$), filtered and concentrated. The concentrate in THF (200 mL) at 25° C. to was treated with 1M NaOH (200 mL), stirred for 5 hours and isolated. The water layer was extracted with ethyl acetate, and the THF and ethyl acetate extracts were combined, washed with water and brine and dried (Na$_2$SO$_4$), filtered and concentrated.

EXAMPLE 6C

This example was prepared by substituting EXAMPLE 6B for EXAMPLE 5B in EXAMPLE 4C.

EXAMPLE 6D

This example was prepared by substituting EXAMPLE 6C and 2-oxa-5-aza-bicyclo[2.2.1]heptane, prepared as described in commonly-owned U.S. patent application Ser. No. 10/988,338, for EXAMPLE 4C and N-isopropylmethyl amine in EXAMPLE 4D.

EXAMPLE 6E

EXAMPLE 6D (7.86 g) in dichloromethane (200 mL) at 25° C. was treated with 2M HCl in diethyl ether (200 mL), stirred for 18 hours and concentrated.

EXAMPLE 6F

This example was prepared by substituting EXAMPLE 6E for EXAMPLE 1D in EXAMPLE 2F.

EXAMPLE 6G

This example was prepared by substituting EXAMPLE 6F and EXAMPLE 3C for EXAMPLE 1I and EXAMPLE 1M in EXAMPLE 1N. $^1$H NMR (300 MHz, DMSO-d$_6$) δ 8.07 (s, 1H), 7.92 (d, 1H), 7.70 (d, 2H), 7.37 (m, 4H), 7.30 (t, 2H), 7.21 (t, 1H), 7.12 (d, 2H), 6.84 (d, 1H), 6.79 (d, 2H), 4.21 (m, 1H), 4.09 (m, 1H), 4.01 (m, 2H), 3.82 (m, 2H), 3.46 (m, 1H), 3.18 (m, 6H), 2.86 (m, 4H), 2.75 (m, 4H), 2.28 (m, 2H), 2.18 (m, 4H), 1.88 (m, 4H), 1.66 (m, 4H).

EXAMPLE 7

This example was prepared by substituting EXAMPLE 3C for EXAMPLE 1M in EXAMPLE 1N. $^1$H NMR (300 MHz, DMSO-d$_6$) δ 8.09 (d, 1H), 7.92 (dd, 1H), 7.71 (d, 2H), 7.31 (m 7H), 7.18 (tt, 1H), 7.12 (dt, 2H), 6.92 (d, 1H), 6.82 (m, 3H), 4.04 (m, 1H), 3.51 (m, 4H), 3.26 (m, 10H), 2.82 (m, 2H), 2.30 (m, 10H), 1.94 (m, 1H), 1.72 (m, 5H).

EXAMPLE 8A

A solution of 3-(9H-fluoren-9-ylmethoxycarbonylamino)-4-phenylsulfanylbutyric acid, prepared as described in commonly-owned U.S. patent application Ser. No. 10/988,338 and HATU in DMF was treated with 7-aza-bicyclo[2.2.1]heptane (prepared as described in Org. Lett., 2001, 3, 1371-1374; and N-methylmorpholine, stirred at ambient temperature for 30 min, diluted with ethyl acetate, washed with 1.5% HCl, NaHCO$_3$(aq), H$_2$O and brine, dried (Na$_2$SO$_4$), filtered and concentrated to give the desired product.

EXAMPLE 8B

A solution of EXAMPLE 8A in THF was treated with diethyl amine, stirred at ambient temperature for 2 hours and concentrated. The residue was purified by silica gel chromatography eluting with CH$_2$Cl$_2$ (saturated with NH$_3$), followed by ethyl acetate to give the desired product.

EXAMPLE 8C

This example was prepared by substituting EXAMPLE 8B for EXAMPLE 1C in EXAMPLE 1D.

EXAMPLE 8D

This example was prepared by substituting EXAMPLE 8C for EXAMPLE 1D in EXAMPLE 1I.

EXAMPLE 8E

This example was prepared by substituting EXAMPLE 8D and EXAMPLE 3C for EXAMPLE 1I and EXAMPLE 1M, respectively, in EXAMPLE 1N. $^1$H NMR (300 MHz, DMSO-d$_6$) δ 9.19 (m, 1H), 8.07 (d, 1H), 7.97 (d, 1H), 7.71 (d, 2H), 7.31 (m 6H), 7.20 (tt, 1H), 7.12 (dt, 2H), 6.89 (d, 1H), 6.76 (d, 2H), 6.65 (d, 1H), 4.03 (m, 2H), 3.31 (m, 4H), 3.12 (m, 4H), 2.90 (br, 2H), 2.76 (m 2H), 1.96 (m, 21H).

EXAMPLE 9A

This example was prepared by substituting EXAMPLE 6E for EXAMPLE 1D in EXAMPLE 1I.

EXAMPLE 9B

This example was prepared by substituting EXAMPLE 9A and EXAMPLE 3C for EXAMPLE 1I and EXAMPLE 1M, respectively, in EXAMPLE 1N. $^1$H NMR (300 MHz, DMSO-$d_6$) δ 8.08 (d, 1H), 7.94 (d, 1H), 7.71 (d, 2H), 7.32 (m 7H), 7.20 (tt, 1H), 7.12 (dt, 2H), 6.87 (d, 1H), 6.78 (d, 3H), 4.40 (m, 1H), 4.03 (m, 2H), 3.83 (m, 2H), 3.54 (m, 2H), 3.26 (m, 2H), 3.14 (m, 4H), 2.80 (br, 2H), 2.78 (m, 4H), 1.97 (m, 14H).

EXAMPLE 10

This example was prepared by substituting EXAMPLE 9A for EXAMPLE 1I in EXAMPLE 1N. $^1$H NMR (300 MHz, DMSO-$d_6$) δ 8.09 (d, 1H), 7.95 (d, 1H), 7.71 (d, 2H), 7.33 (m 7H), 7.20 (tt, 1H), 7.12 (dt, 2H), 6.90 (d, 1H), 6.79 (d, 3H), 4.44 (m, 1H), 4.03 (m, 1H), 3.84 (m, 1H), 3.57 (m, 1H), 3.02 (m, 13H), 2.25 (m, 6H), 1.99 (m, 6H), 1.43 (t, 2H), 0.97 (s, 6H).

EXAMPLE 11

This example was prepared by substituting EXAMPLE 6F for EXAMPLE 1I in EXAMPLE 1N. $^1$H NMR (300 MHz, DMSO-$d_6$) δ 8.07 (d, 1H), 7.93 (d, 1H), 7.70 (d, 2H), 7.33 (m 7H), 7.20 (tt, 1H), 7.12 (dt, 2H), 6.81 (m, 4H), 4.41 (m, 1H), 4.06 (m, 1H), 3.83 (m, 1H), 3.47 (m, 1H), 3.02 (m, 13H), 2.25 (m, 6H), 1.99 (m, 6H), 1.43 (t, 2H), 0.97 (s, 6H).

EXAMPLE 12

This example was prepared by substituting 4-(4-(2-(4-chlorophenyl)cyclohept-1-enylmethyl)piperazin-1-yl)benzoic acid, prepared as described in commonly-owned U.S. patent application Ser. No. 10/988,338, and EXAMPLE 9A for EXAMPLE 1M and EXAMPLE 1I, respectively, in EXAMPLE 1N. $^1$H NMR (300 MHz, DMSO-$d_6$) δ 8.09 (d, 1H), 7.95 (dd, 1H), 7.71 (d, 2H), 7.32 (m 7H), 7.19 (tt, 1H), 7.09 (dt, 2H), 6.90 (d, 1H), 6.79 (d, 3H), 4.45 (m, 1H), 4.03 (m, 2H), 3.85 (m, 2H), 3.55 (m, 2H), 3.04 (m, 8H), 2.34 (m, 8H), 1.85 (m, 7H), 1.54 (m, 5H).

EXAMPLE 13

This example was prepared by substituting 4-(4-(2-(4-chlorophenyl)cyclohept-1-enylmethyl)piperazin-1-yl)benzoic acid, prepared as described in commonly-owned U.S. patent application Ser. No. 10/988,338, and EXAMPLE 6F for EXAMPLE 1M and EXAMPLE 1I, respectively, in EXAMPLE 1N. $^1$H NMR (300 MHz, DMSO-$d_6$) δ 8.07 (d, 1H), 7.93 (dd, 1H), 7.71 (d, 2H), 7.32 (m 7H), 7.20 (tt, 1H), 7.09 (dt, 2H), 6.87 (d, 1H), 6.79 (d, 3H), 4.45 (m, 1H), 4.02 (m, 2H), 3.84 (m, 2H), 3.56 (m, 2H), 3.07 (m, 8H), 2.33 (m, 8H), 1.85 (m, 7H), 1.54 (m, 5H).

EXAMPLE 14

This example was prepared by substituting EXAMPLE 2K and EXAMPLE 4F for EXAMPLE 1M and EXAMPLE 1I, respectively, in EXAMPLE 1N. $^1$H NMR (300 MHz, DMSO-$d_6$) δ 8.07 (d, 1H), 7.96 (dd, 1H), 7.71 (d, 2H), 7.33 (m 7H), 7.20 (tt, 1H), 7.09 (dt, 2H), 6.87 (d, 1H), 6.77 (d, 2H), 6.72 (d, 1H), 4.00 (m, 1H), 3.28 (m, 4H), 3.12 (m, 4H), 2.79 (m, 2H), 2.48 (m, 2H), 2.23 (m, 8H), 2.02 (m, 4H), 1.42 (t, 2H), 1.08 (m, 6H), 0.96 (s, 6H).

EXAMPLE 15A

This example was prepared by substituting EXAMPLE 6C and 1,4-oxazepane for EXAMPLE 4C and N-isopropyl-N-methylamine in EXAMPLE 4D.

EXAMPLE 15B

This example was prepared by substituting EXAMPLE 15A for EXAMPLE 6D in EXAMPLE 6E.

EXAMPLE 15C

This example was prepared by substituting EXAMPLE 15B for EXAMPLE 1D in EXAMPLE 1I.

EXAMPLE 15D

This example was prepared by substituting EXAMPLE 15C and EXAMPLE 3C for EXAMPLE 1I and EXAMPLE 1M, respectively, in EXAMPLE 1N. $^1$H NMR (400 MHz, CDCl$_3$) δ 8.32 (s, 1H), 8.01 (br, 1H), 7.67 (d, 2H), 7.34 (t, 4H), 7.24 (m, 3H), 6.99 (m, 3H), 6.67 (br, 3H), 3.97 (br, 1H), 3.88 (s, 2H), 3.79 (s, 2H), 3.73-3.23 (br m, 12H), 3.14 (m, 6H), 2.29 (s, 6H), 2.08 (m, 2H), 1.74 (s, 4H).

EXAMPLE 16A

This example was prepared by substituting azepane for N-isopropyl-N-methylamine in EXAMPLE 4D.

EXAMPLE 16B

This example was prepared by substituting EXAMPLE 16A for EXAMPLE 4D in EXAMPLE 4E.

EXAMPLE 16C

This example was prepared by substituting EXAMPLE 16A for EXAMPLE 1D in EXAMPLE 1I.

EXAMPLE 16D

This example was prepared by substituting EXAMPLE 16C and EXAMPLE 3C for EXAMPLE 1I and EXAMPLE 1M, respectively, in EXAMPLE 1N. $^1$H NMR (400 MHz, CDCl$_3$) δ 8.33 (s, 1H), 8.01 (d, 1H), 7.67 (d, 2H), 7.34 (t, 4H), 7.23 (m, 3H), 6.98 (m, 3H), 6.67 (m, 3H), 3.99 (m, 1H), 3.82-3.19 (br m, 10H), 3.12 (s, 4H), 2.86 (m, 2H), 2.55 (br, 2H), 2.29 (s, 4H), 2.06 (m, 1H), 1.93 (m, 3H), 1.74 (s, 8H), 1.60 (m, 2H).

EXAMPLE 17A

This example was prepared by substituting EXAMPLE 6A for EXAMPLE 1C in EXAMPLE 1D.

EXAMPLE 17B

This example was prepared by substituting EXAMPLE 17B for EXAMPLE 1D in EXAMPLE 1I.

EXAMPLE 17C

This example was prepared by substituting 4-(4-(2-(4-chlorophenyl)cyclohept-1-enylmethyl)piperazin-1-yl)benzoic acid, prepared as described in commonly-owned U.S. patent application Ser. No. 10/988,338, and EXAMPLE 17B for EXAMPLE 1M and EXAMPLE 1I, respectively, in EXAMPLE 1N. $^1$H NMR (400 MHz, DMSO-$d_6$) δ 9.58 (brs, 1H), 9.46 (brs, 1H), 8.18 (d, 1H), 8.00 (dd, 1H), 7.77 (d, 2H), 7.41 (d, 2H), 7.29 (d, 2H), 7.24 (m, 2H), 7.13 (m, 4H), 6.96 (m, 3H), 4.12 (m, 1H), 3.87 (m, 1H), 3.63 (m, 1H), 3.38 (m, 4H), 3.15 (m, 4H), 3.02 (m, 2H), 2.74 (s, 6H), 2.46 (m, 4H), 2.09 (m, 2H), 1.81 (m, 2H), 1.57 (m, 4H).

EXAMPLE 18A

This example was prepared by substituting EXAMPLE 2E and EXAMPLE 17B for EXAMPLE 1H and EXAMPLE 1D in EXAMPLE 1I.

EXAMPLE 18B

This example was prepared by substituting EXAMPLE 18A and EXAMPLE 3C for EXAMPLE 1I and EXAMPLE 1M, respectively, in EXAMPLE 1N. $^1$H NMR (400 MHz, DMSO-$d_6$) δ 9.60 (brs, 1H), 9.47 (brs, 1H), 8.18 (d, 1H), 7.99 (dd, 1H), 7.77 (d, 2H), 7.41 (d, 2H), 7.30 (d, 2H), 7.24 (m, 2H), 7.15 (m, 3H), 7.12 (d, 1H), 6.96 (m, 3H), 6.92 (d, 1H), 4.10 (m, 1H), 3.91 (m, 2H), 3.60 (m, 2H), 3.37 (m, 4H), 3.15 (m, 2H), 3.02 (m, 1H), 2.74 (s, 6H), 2.25 (d, 4H), 2.08 (m, 2H), 1.71 (m, 4H).

EXAMPLE 19

This example was prepared by substituting EXAMPLE 2F for EXAMPLE 1I in EXAMPLE 1N. $^1$H NMR (400 MHz, DMSO-$d_6$) δ 8.11 (d, 1H), 7.93 (dd, 1H), 7.71 (d, 2H), 7.36 (m, 4H), 7.27 (m, 2H), 7.18 (m, 1H), 7.12 (d, 2H), 6.97 (d, 1H), 6.85 (m, 3H), 4.05 (m, 1H), 3.53 (m, 4H), 3.23 (m, 1H), 2.83 (m, 1H), 2.34 (m, 8H), 2.22 (m, 2H), 1.99 (m, 2H), 1.96 (m, 1H), 1.77 (m, 1H), 1.44 (t, 2H), 0.97 (s, 6H).

EXAMPLE 20

This example was prepared by substituting EXAMPLE 17B for EXAMPLE 1I in EXAMPLE 1N. $^1$H NMR (500 MHz, DMSO-$d_6$) δ 9.46 (brs, 1H), 8.18 (d, 1H), 7.99 (dd, 1H), 7.76 (d, 2H), 7.40 (d, 2H), 7.29 (d, 2H), 7.23 (t, 2H), 7.14 (s, 4H), 6.95 (m, 3H), 4.11 (m, 1H), 3.88 (m, 2H), 3.58 (m, 4H), 3.08 (m, 4H), 2.73 (s, 6H), 2.27 (m, 2H), 2.08 (m, 2H), 2.02 (s, 2H), 1.47 (t, 2H), 1.00 (s, 6H).

EXAMPLE 21

This example was prepared by substituting 4-(4-(4-(4-chlorophenyl)-5,6-dihydro-2H-pyran-3-ylmethyl)piperazin-1-yl)benzoic acid, prepared as described in commonly-owned U.S. patent application Ser. No. 10/988,338, for EXAMPLE 1M in EXAMPLE 1N. $^1$H NMR (400 MHz, DMSO-$d_6$) δ 8.27 (d, 1H), 8.11 (d, 1H), 7.89 (d, 2H), 7.59 (d, 2H), 7.48 (m, 4H), 7.37 (m, 3H), 7.13 (m, 1H), 7.01 (m, 3H), 4.35 (s, 2H), 4.24 (m, 1H), 3.97 (m, 2H), 3.68 (m, 4H), 3.36 (m, 6H), 3.07 (m, 3H), 2.68 (s, 2H), 2.59 (m, 4H), 2.14 (m, 2H), 1.93 (m, 2H).

EXAMPLE 22A

This example was prepared by substituting EXAMPLE 4E for EXAMPLE 2E in EXAMPLE 2F.

EXAMPLE 22

This example was prepared by substituting EXAMPLE 2K and EXAMPLE 22A for EXAMPLE 1M and EXAMPLE 1I, respectively, in EXAMPLE 1N. $^1$H NMR (400 MHz, DMSO-$d_6$) δ 9.21 (brs, 1H), 8.17 (m, 1H), 8.00 (dd, 1H), 7.77 (d, 2H), 7.42 (m, 2H), 7.31 (m, 2H), 7.24 (m, 2H), 7.14 (m, 4H), 6.97 (m, 3H), 4.11 (m, 1H), 3.90 (m, 1H), 3.12 (m, 6H), 2.84 (m, 3H), 2.63 (m, 3H), 2.25 (m, 2H), 2.07 (m, 4H), 1.49 (t, 2H), 1.16 (m, 6H), 0.97 (s, 6H).

EXAMPLE 23

This example was prepared by substituting EXAMPLE 22A for EXAMPLE 1I in EXAMPLE 1N. $^1$H NMR (400 MHz, DMSO-$d_6$) δ 9.21 (brs, 1H), 8.18 (m, 1H), 7.99 (dd, 1H), 7.78 (d, 2H), 7.40 (d, 2H), 7.30 (d, 2H), 7.24 (m, 2H), 7.15 (m, 4H), 6.97 (m, 3H), 4.11 (m, 1H), 3.89 (m, 1H), 3.13 (m, 6H), 2.84 (m, 2H), 2.63 (m, 3H), 2.28 (m, 2H), 2.07 (m, 4H), 1.48 (t, 2H), 1.17 (m, 6H), 1.00 (s, 6H).

EXAMPLE 24

This example was prepared by substituting EXAMPLE 2K for EXAMPLE 1M in EXAMPLE 1N. $^1$H NMR (500 MHz, DMSO-$d_6$) δ 12.14 (brs, 1H), 9.89 (brs, 1H), 9.52 (s, 1H), 8.18 (d, 1H), 8.00 (dd, 1H), 7.77 (d, 2H), 7.41 (d, 2H), 7.30 (d, 2H), 7.24 (t, 2H), 7.14 (m, 4H), 6.96 (m, 3H), 4.12 (m, 1H), 3.93 (m, 3H), 3.63 (m, 4H), 2.93 (m, 10H), 2.24 (m, 2H), 2.09 (m, 4H), 1.48 (t, 2H), 0.97 (s, 6H).

EXAMPLE 25

This example was prepared by substituting EXAMPLE 2K and EXAMPLE 6F for EXAMPLE 1M and EXAMPLE 1I, respectively, in EXAMPLE 1N. $^1$H NMR (500 MHz, DMSO-$d_6$) δ 9.58 (brs, 1H), 9.39 (brs, 1H), 8.17 (s, 1H), 7.99 (dd, 1H), 7.77 (d, 2H), 7.41 (d, 2H), 7.30 (d, 2H), 7.24 (t, 2H), 7.14 (m, 4H), 6.97 (m, 3H), 4.63 (d, 1H), 4.43 (d, 1H), 4.13 (m, 1H), 3.92 (m, 2H), 3.69 (m, 2H), 3.52 (m, 2H), 3.01 (m, 6H), 2.25 (m, 2H), 2.04 (m, 6H), 1.49 (m, 2H), 0.98 (s, 6H).

EXAMPLE 26

This example was prepared by substituting EXAMPLE 17B and EXAMPLE 3C for EXAMPLE 1I and EXAMPLE 1M, respectively, in EXAMPLE 1N. $^1$H NMR (500 MHz, DMSO-$d_6$) δ 9.49 (brs, 1H), 8.08 (d, 1H), 7.95 (dd, 1H), 7.71 (d, 2H), 7.36 (m, 4H), 7.30 (t, 2H), 7.20 (t, 1H), 7.12 (d, 2H), 6.84 (m, 2H), 6.78 (d, 2H), 3.98 (m, 1H), 3.28 (m, 2H), 3.12 (brs, 4H), 2.81 (brs, 1H), 2.77 (s, 1H), 2.46 (s, 6H), 2.28 (s, 4H), 2.19 (m, 4H), 2.00 (m, 1H), 1.90 (m, 1H), 1.65 (m, 4H).

EXAMPLE 27A

This example was prepared by substituting pyrrolidine for N-isopropylethylamine in EXAMPLE 4D.

EXAMPLE 27B

This example was prepared by substituting EXAMPLE 27A for EXAMPLE 4D in EXAMPLE 4E.

EXAMPLE 27C

This example was prepared by substituting EXAMPLE 27B for EXAMPLE 1D in EXAMPLE 1I.

EXAMPLE 27D

This example was prepared by substituting EXAMPLE 27C and EXAMPLE 3C for EXAMPLE 1I and EXAMPLE 1M, respectively, in EXAMPLE 1N. $^1$H NMR (400 MHz, DMSO-$d_6$) δ 8.08 (d, 1H), 7.96 (dd, 1H), 7.71 (d, 2H), 7.36 (m, 4H), 7.30 (t, 2H), 7.20 (t, 1H), 7.12 (d, 2H), 6.87 (m, 1H), 6.77 (d, 2H), 6.72 (d, 1H), 4.00 (m, 1H), 3.26 (m, 2H), 3.12 (brs, 4H), 2.97 (m, 6H), 2.76 (s, 1H), 2.28 (brs, 4H), 2.19, (m, 4H), 2.05 (m, 1H), 1.95 (m, 1H), 1.82 (brs, 4H), 1.65 (m, 4H).

EXAMPLE 28

This example was prepared by substituting EXAMPLE 2K and EXAMPLE 17B for EXAMPLE 1M and EXAMPLE 1I, respectively, in EXAMPLE 1N. $^1$H NMR (500 MHz, DMSO-$d_6$) δ 9.59 (brs, 1H), 8.08 (d, 1H), 7.94 (dd, 1H), 7.70 (d, 2H), 7.36 (m, 4H), 7.30 (t, 2H), 7.21 (tt, 1H), 7.09 (d, 2H), 6.83 (d, 1H), 6.78 (d, 3H), 3.97 (m, 1H), 3.28 (m, 2H), 3.13 (brs, 4H), 2.90 (brs, 2H), 2.79 (s, 2H), 2.55 (s, 6H), 2.28 (brs, 4H), 2.20 (m, 2H), 1.99 (s, 2H), 1.90 (m, 2H), 1.42 (t, 2H), 0.96 (s, 6H).

EXAMPLE 29

This example was prepared by substituting 4-(4-(2-(4-chlorophenyl)cyclo-1-enylmethyl)piperazin-1-yl)benzoic acid, prepared as described in commonly-owned U.S. patent application Ser. No. 10/988,338, and EXAMPLE 27C for EXAMPLE 1M and EXAMPLE 1I, respectively, in EXAMPLE 1N. $^1$H NMR (400 MHz, DMSO-$d_6$) δ 9.60 (brs, 1H), 8.08 (d, 1H), 7.94 (dd, 1H), 7.71 (d, 2H), 7.36 (m, 4H), 7.30 (t, 2H), 7.20 (t, 1H), 7.09 (d, 2H), 6.83 (d, 1H), 6.77 (d, 3H), 3.99 (m, 1H), 3.26 (m, 2H), 3.12 (brs, 4H), 2.80 (m, 5H), 2.76 (s, 2H), 2.40 (m, 4H), 2.31 (brs, 4H), 1.99 (m, 1H), 1.89 (m, 1H), 1.77 (brs, 6H), 1.58 (m, 2H), 1.51 (m, 2H).

EXAMPLE 30A

This example was prepared by substituting EXAMPLE 2E and EXAMPLE 27B for EXAMPLE 1H and EXAMPLE 1D in EXAMPLE 1I.

EXAMPLE 30B

This example was prepared by substituting EXAMPLE 30A for EXAMPLE 1I and EXAMPLE 1D in EXAMPLE 1N. $^1$H NMR (400 MHz, DMSO-$d_6$) δ 9.57 (brs, 1H), 8.07 (d, 1H), 7.93 (dd, 1H), 7.70 (d, 2H), 7.36 (m, 4H), 7.30 (t, 2H), 7.21 (t, 1H), 7.12 (d, 2H), 6.81 (d, 1H), 6.77 (d, 3H), 3.99 (m, 1H), 3.26 (m, 2H), 3.12 (brs, 4H), 2.80 (m, 5H), 2.76 (s, 2H), 2.27 (m, 4H), 2.22 (m, 2H), 1.99 (m, 3H), 1.88 (m, 1H), 1.77 (brs, 4H), 1.43 (t, 2H), 0.97 (s, 6H).

EXAMPLE 31

This example was prepared by substituting EXAMPLE 2K and EXAMPLE 30A for EXAMPLE 1M and EXAMPLE 1I, respectively, in EXAMPLE 1N. $^1$H NMR (400 MHz, DMSO-$d_6$) δ 9.52 (brs, 1H), 8.06 (d, 1H), 7.92 (dd, 1H), 7.70 (d, 2H), 7.36 (m, 4H), 7.30 (t, 2H), 7.21 (t, 1H), 7.08 (d, 2H), 6.81 (d, 1H), 6.77 (d, 3H), 3.99 (m, 1H), 3.26 (m, 2H), 3.12 (brs, 4H), 2.76 (s, 2H), 2.75 (m, 5H), 2.26 (m, 4H), 2.20 (m, 2H), 1.99 (m, 3H), 1.86 (m, 1H), 1.76 (brs, 4H), 1.42 (t, 2H), 0.96 (s, 6H).

EXAMPLE 32

This example was prepared by substituting 4-(4-(2-(4-chlorophenyl)cyclohept-1-enylmethyl)piperazin-1-yl)benzoic acid, prepared as described in commonly-owned U.S. patent application Ser. No. 10/988,338, and EXAMPLE 30A for EXAMPLE 1M and EXAMPLE 1I, respectively, in EXAMPLE 1N. $^1$H NMR (400 MHz, DMSO-$d_6$) δ 9.50 (brs, 1H), 8.08 (d, 1H), 7.94 (dd, 1H), 7.71 (d, 2H), 7.36 (m, 4H), 7.30 (t, 2H), 7.20 (t, 1H), 7.09 (d, 2H), 6.83 (d, 1H), 6.77 (d, 3H), 3.99 (m, 1H), 3.26 (m, 2H), 3.12 (brs, 4H), 2.80 (m, 5H), 2.76 (s, 2H), 2.40 (m, 4H), 2.31 (brs, 4H), 1.98 (m, 1H), 1.87 (m, 1H), 1.76 (brs, 6H), 1.58 (m, 2H), 1.51 (m, 2H).

EXAMPLE 33

This example was prepared by substituting EXAMPLE 4F and EXAMPLE 3C for EXAMPLE 1I and EXAMPLE 1M, respectively, in EXAMPLE 1N. $^1$H NMR (300 MHz, DMSO-$d_6$) δ 9.03 (s, 1H), 8.08 (d, 1H), 7.97 (d, 1H), 7.71 (d, 2H), 7.39-7.34 (m, 4H), 7.30 (t, 2H), 7.20 (tt, 1H), 7.13 (dt, 2H), 6.88 (m, 1H), 6.78 (d, 2H), 6.70 (m, 1H), 3.99 (m, 1H), 3.37-3.26 (m, 4H), 3.12 (s, 4H), 2.76 (s, 2H), 2.68-2.53 (m, 2H), 2.34-2.13 (m, 10H), 2.10-1.95 (m, 2H), 1.66 (s, 4H), 1.13 (m, 6H).

EXAMPLE 34

This example was prepared by substituting EXAMPLE 2K and EXAMPLE 27C for EXAMPLE 1M and EXAMPLE 1I, respectively, in EXAMPLE 1N. $^1$H NMR (300 MHz, DMSO-$d_6$) δ 9.53 (s, 1H), 8.08 (d, 1H), 7.97 (dd, 1H), 7.71 (d, 2H), 7.40-7.34 (m, 4H), 7.30 (t, 2H), 7.20 (tt, 1H), 7.09 (d, 2H), 6.89 (d, 1H), 6.78 (d, 2H), 6.71 (d, 1H), 4.01 (m, 1H), 3.38-3.27 (m, 4H), 3.20-2.84 (m, 10H), 2.79 (s, 2H), 2.27 (s, 4H), 2.20 (t, 2H), 2.03 (m, 2H), 1.85 (m, 4H), 1.42 (t, 2H), 0.96 (s, 6H).

EXAMPLE 35

This example was prepared by substituting EXAMPLE 3C and EXAMPLE 30A for EXAMPLE 1M and EXAMPLE 1I, respectively in EXAMPLE 1N. $^1$H NMR (400 MHz, DMSO-$d_6$) δ ppm 8.06 (d, 1H), 7.93 (dd, 1H), 7.71 (d, 2H), 7.36 (m, 4H), 7.30 (m, 2H), 7.21 (m, 1H), 7.12 (d, 2H), 6.81 (d, 1H), 6.77 (d, 3H), 3.97 (m, 1H), 3.26 (m, 4H), 3.12 (s, 4H), 2.78 (m, 6H), 2.27 (s, 4H), 2.18 (m, 4H), 1.99 (m, 1H), 1.87 (m, 1H), 1.76 (s, 4H), 1.66 (s, 4H).

EXAMPLE 36

This example was prepared by substituting EXAMPLE 2K and EXAMPLE 9A for EXAMPLE 1M and EXAMPLE 1I, respectively, in EXAMPLE 1N. $^1$H NMR (400 MHz, DMSO-$d_6$) δ 8.09 (d, 1H), 7.97 (dd, 1H), 7.71 (d, 2H), 7.33 (m, 6H), 7.21 (m, 1H), 7.08 (d, 2H), 6.87 (m, 1H), 6.78 (m, 3H), 3.99 (m, 1H), 3.14 (m, 4H), 2.95 (m, 1H), 2.80 (m, 3H), 2.58 (s, 6H), 2.28 (m, 4H), 2.20 (m, 2H), 1.99 (m, 4H), 1.42 (t, 2H), 0.96 (s, 6H).

EXAMPLE 37

This example was prepared by substituting EXAMPLE 2K and EXAMPLE 17B for EXAMPLE 1M and EXAMPLE 1I, respectively, in EXAMPLE 1N. $^1$H NMR (400 MHz, DMSO-d$_6$) δ 8.09 (d, 1H), 7.97 (dd, 1H), 7.71 (d, 2H), 7.33 (m, 6H), 7.21 (m, 1H), 7.08 (d, 2H), 6.87 (m, 1H), 6.78 (m, 3H), 3.99 (m, 1H), 3.14 (m, 4H), 2.95 (m, 1H), 2.80 (m, 3H), 2.58 (s, 6H), 2.28 (m, 4H), 2.20 (m, 2H), 1.99 (m, 4H), 1.42 (t, 2H), 0.96 (s, 6H).

EXAMPLE 38

This example was prepared by substituting 4-(4-(1,1'-biphenyl-2-ylmethyl)-1-piperazinyl)benzoic acid, prepared as described in commonly-owned U.S. patent application Ser. No. 10/988,338, for EXAMPLE 1M and EXAMPLE 17B for EXAMPLE 1I, respectively, in EXAMPLE 1N. $^1$H NMR (400 MHz, DMSO-d$_6$) δ 8.19 (d, 1H), 7.99 (dd, 1H), 7.76 (d, 3H), 7.52 (d, 4H), 7.40 (d, 2H), 7.35 (m, 1H), 7.30 (d, 2H), 7.24 (t, 2H), 7.16 (t, 2H), 6.96 (m, 3H), 4.25 (br, 2H), 4.12 (m, 1H), 3.37 (m, 2H), 3.14 (m, 1H), 3.10 (br, 8H), 2.74 (s, 6H), 2.10 (m, 2H).

EXAMPLE 39

This example was prepared by substituting 4-(4-(1,1'-biphenyl-2-ylmethyl)-1-piperazinyl)benzoic acid, prepared as described in commonly-owned U.S. patent application Ser. No. 10/988,338, for EXAMPLE 1M in EXAMPLE 1N. $^1$H NMR (400 MHz, DMSO-d$_6$) δ 8.19 (d, 1H), 8.00 (dd, 1H), 7.76 (d, 2H), 7.52 (m, 5H), 7.14 (m, 8H), 6.96 (m, 3H), 4.29 (m, 2H), 4.14 (m, 2H), 4.02 (m, 1H), 3.10 (m, 8H), 2.13 (m, 2H).

EXAMPLE 40

Antibodies

All antibodies were purchased from commercial sources as follows: antibodies against INCENP, histone H3, histone H3-(pSer$^{10}$), BIK, PUMA, and BAK were from Cell Signaling Technology; antibodies against Aurora B, Bad, and Ral-A were from Epitomics; antibodies against Aurora A, p53, cytochrome C, Bid, and Bim were from BD Biosciences; antibodies against Bcl-2, Bcl-X$_L$, Mcl-1, and S6K1 were from Santa Cruz Biotechnology; antibodies against BAX were from Abcam; antibodies against NOXA were from Imgenex; antibodies against the active BAX conformer (6A7) were from Sigma; antibodies against the active BAK conformer (Ab2) were from Calbiochem; antibodies against β-actin were from R&D systems.

Small-Molecules and siRNAs

Active components of the clinical drugs BCNU, Doxorubicin, Gemcitabine, Etoposide, 5-FU, ALIMTA, Rapamycin, and the previously disclosed Abbott compounds, ABT-751 (β-tubulin inhibitor), ABT-888 (PARP inhibitor) (See, Donawho, C. K. et al., "ABT-888, an orally active poly(ADP-ribose) polymerase inhibitor that potentiates DNA-damaging agents in preclinical tumor models," *Clin Cancer Res* 13, 2728-37 (2007)), ABT-263 (Bcl-2 protein family inhibitor) (See, Tse, C. et al., "ABT-263: a potent and orally bioavailable Bcl-2 family inhibitor," *Cancer Res* 68, 3421-8 (2008)), Ritonavir (See, Kempf, D. J. et al., "Discovery of ritonavir, a potent inhibitor of HIV protease with high oral bioavailability and clinical efficacy," *J Med Chem* 41, 602-17 (1998)), A-443654 (AKT inhibitor) (See, Luo, Y. et al., "Potent and selective inhibitors of Akt kinases slow the progress of tumors in vivo," *Mol Cancer Ther* 4, 977-86 (2005)), and A-407846 (histone deacetylase) (See, Vasudevan, A. et al., "Heterocyclic ketones as inhibitors of histone deacetylase," *Bioorg Med Chem Lett* 13, 3909-13 (2003)) were obtained from the Compound Depository of Abbott Laboratories, the assignee of the present application. 17-AAG was purchased from AG Scientific (San Diego, Calif.). The chemical structures of MLN8054 (See, Manfredi, M. G. et al., "Antitumor activity of MLN8054, an orally active small-molecule inhibitor of Aurora A kinase," *Proc Natl Acad Sci USA* 104, 4106-11 (2007)), AZD1152 (See, Mortlock, A. A. et al., "Discovery, synthesis, and in vivo activity of a new class of pyrazoloquinazolines as selective inhibitors of aurora B kinase," *J Med Chem* 50, 2213-24 (2007)), and VX-680/MK-0457 (See, Harrington, E. A. et al., "VX-680, a potent and selective small-molecule inhibitor of the Aurora Kinases, suppresses tumor growth in vivo," *Nat Med* 10, 262-7 (2004)) and BI 2536 have been disclosed. These compounds were synthesized at Abbott Laboratories for comparative purposes. AZD1152-hydroxyquinazoline pyrazol anilide (HQPA) is rapidly converted from the dihydrogen phosphate prodrug, AZD1152, in the presence of plasma (See, Mortlock, A. A. et al., "Discovery, synthesis, and in vivo activity of a new class of pyrazoloquinazolines as selective inhibitors of aurora B kinase," *J Med Chem* 50, 2213-24 (2007)). For all studies, AZD1152-HQPA was used and referred to as AZD1152.

siRNAs against Bcl-2, Bcl-X$_L$, Mcl-1, Aurora A, Aurora B, INCENP, BIK, NOXA, BAX, BAK, PUMA, BAD, and BIM were purchased from Dharmacon (Lafayette, Colo.). For each target, a set of 40N-TARGET Plus siRNAs were prescreened for target knockdown and off-target cytotoxicity. siRNAs that triggered more than a 70% reduction of target protein without causing more than a 10% off-target growth inhibition in a 72-hour proliferation assay were selected for all siRNA-related studies. The most potent siRNA against each target was used in experiments where only one siRNA/target was used. The control, nontargeting siRNA and a previously described luciferase siRNA (See, Lin, X. et al., "'Seed' analysis of off-target siRNAs reveals an essential role of Mcl-1 in resistance to the small-molecule Bcl-2/Bcl-X$_L$ inhibitor ABT-737," *Oncogene* 26, 3972-9 (2007)) were also purchased from Dharmacon.

Cell Culture and Animal Studies

The human cancer cell lines SW620, D54MG, A549, PC3, EJ1, DLD1, HCT116, and 786-O were purchased from American Type Culture Collection (ATCC). All cell lines were cultured according to the supplier's recommendations.

C.B.-17 scid-bg (scid-bg) or C.B.-17 scid (scid) mice were obtained from Charles River Laboratories at 5-6 weeks of age and used for studies when greater than 8 weeks of age and/or ~20 g in size. All animal studies were conducted in a specific pathogen-free environment in accordance with the Internal Institutional Animal Care and Use Committee (IACUC), accredited by the American Association of Laboratory Animal Care under conditions that meet or exceed the standards set by the United States Department of Agriculture Animal Welfare Act, Public Health Service policy on humane care and use of animals, and the NIH guide on laboratory animal welfare. Overt signs of dehydration, lack of grooming, lethargy, >15% weight loss as well as tumor volume >20% of body weight were used to determine tumor endpoint.

The tumor cell line HCT116 was routinely tested for *Mycoplasma* and confirmed to be microbe-free by infectious microbe PCR amplification test (IMPACT, Missouri Research Animal Diagnostic Laboratory) prior to in vivo inoculation. Cells were grown in RPMI supplemented with 1 mM L-glutamine and 10% fetal bovine serum, maintained at 37° C. in a humidified atmosphere equilibrated with 5% CO$_2$, 95% air and used between passages 3-7 when in log phase for tumor cell inoculation. Cells (1×10$^6$) were mixed 1:1 with matrigel (BD Biosciences) and injected s.c. (0.2 mL) into the shaved flank of female mice. Tumors were size-matched (482-606 mm$^3$) and allocated into treatment groups before dosing was initiated. Two bisecting diameters were measured with calipers and tumor volumes were estimated from the formula: (length×width$^2$)/2. VX-680 was administered intraperitoneally (I.P., 50 mg/kg/d, b.i.d. to end; 17 days depending on when the endpoint was reached and the study was terminated) in a vehicle containing 10% Solutol (BASF, Florham Park, N.J.) and 90% tartaric acid (Sigma-Aldrich, St. Louis, Mo.). AZD1152 was administered I.P. (100 mg/kg/d, b.i.d.×3) in a vehicle containing 2% ethanol, 5% Tween-80, 20% PEG-400, 73% HPMC (Sigma-Aldrich). ABT-263 was administered PO, 75 or 100 mg/kg/d, q.d.×13-17d in a vehicle containing 60% Phosal 50, 30% PEG 400, 10% ethanol. Agents were initially dosed concurrently in combination therapies for the duration indicated.

siRNA Transfections

Typically, cells were seeded at 5,000/well in 96-well plates in antibiotic-free growth medium and cultured overnight. The following day, cells were transfected with siRNA oligos using Lipofectamine RNAiMAX transfection reagent (Invitrogen) or DharmaFECT transfection reagent according to the manufacturer's recommendations. Individual siRNAs were transfected at a final concentration of 10 nM. For immunoblotting experiments, cells were cultured for a further 3 days, then lysates were prepared. For, siRNA/drug combinations, cells were treated with compound 24 hour post-transfection, then cultured for a further 72 hours. For long-term polyploidization, cells were cultured for up to 10 days post-transfection.

Cell Viability Assay and Caspase 3/7 Assay

Cell viability was determined using the CellTiter-GLO luminescence assay (Promega) according to manufacturer's suggested protocol. Generally, cells were seeded at >90% viability (as determined by trypan blue exclusion) into 96-well plates overnight, treated with compounds or siRNAs for indicated duration, and the overall cell viability was determined by measuring luminescence.

Caspase-3 activity was determined using the Caspase-GLO 3/7 Assay (Promega) in tandem with the CellTiter-GLO viability assay (Promega). Parallel experiments were performed, where in one experiment Caspase-3/7 activity was measured and in the other, cell viability was determined. As Caspase-3/7 activity on a per cell basis reflects both the specific activity of the Caspase-3 enzyme and the number of viable cells, the data are expressed as Caspase-3/7 activity divided by cell viability.

Immunoblotting and Immunoprecipitation

Cell lysates were either prepared using a CHAPS lysis buffer (10 mM HEPES, pH 7.4, 150 mM NaCl, 1% CHAPS) or a cell extraction buffer containing 1% Triton X-100, 0.1% SDS, and 0.5% deoxycholate (Invitrogen). All buffers were supplemented with protease and phosphatase inhibitor cocktails (Sigma) prior to use. For immunoblotting, lysates were mixed with 3× loading buffer (Cell Signaling Technology) and equal amounts of protein were separated by electrophoresis on Bis/Tris gels (Invitrogen). For immunoprecipitation, lysates were prepared in CHAPS lysis buffer and >4 mg of cell lysate was mixed with at least 8 μg of immunoprecipitating antibody overnight at 4° C. The following day, 30 μl of a Protein A- or Protein G-agarose slurry was added for an additional 2 hr. Immunoprecipitates were washed three times in CHAPS lysis buffer, and heated in 1.5× loading buffer at 95'C for 5 minutes.

Purification of Cytosol

Approximately 20×10$^6$ cells were rinsed once in ice-cold PBS, trypsinized, and centrifuged for 2 minutes at 1,300 rpm at 25'C. Cell pellets were rinsed once with PBS and transferred to microcentrifuge tubes. The pellet was allowed to swell in 200 μl homogenization buffer (10 mM HEPES, pH 7.4, 250 mM D-mannitol, 1 mM EGTA, 10 mM KCl, and 5 mM MgCl$_2$ with phosphatase and protease inhibitors) for 30 min, then dounce homogenized with 50 strokes using a type-B pestle. Cell homogenates were centrifuged twice at 1,000×g for 5 minutes at 4'C to pellet nuclei and cell debris. The supernatant was centrifuged at 10,000×g for 10 minutes at 4'C. The pellet from this spin was designated "mitochondria" and further extracted in 80 μl of CHAPS lysis buffer. Extraction of mitochondria was performed on ice by repeatedly vortexing the samples for 1 minute each for ~20 minutes. The final extract was clarified by centrifugation at 14,000×g for 10 minutes at 4° C. to remove any contaminating cell debris. The 10,000×g supernatant containing cytosol and low density membranes was centrifuged again at 100,000×g (55,000 rpm in a TLA 120.2 rotor) for 1 hour to pellet membranes. The supernatant was designated "cytosol" and boiled directly in sample buffer.

Determination of Drug-Drug Interactions

Synergistic activities of VX-680 and chemotherapeutic agents were determined using the Bliss additivism model (See, Berenbaum, M. C., "Criteria for analyzing interactions between biologically active agents," *Adv Cancer Res* 35, 269-335 (1981)) where the combined response C of both agents with individual effects A and B is C=A+B−(A■B) where A and B represent the fractional inhibition between 0 and 1. Combined response scores greater than 15 were considered synergistic.

Gene Expression Analysis by Microarray

Frozen cell pellets were lysed and total RNA was isolated using the QIAshredder and RNeasy columns (Qiagen). Labeled cRNA was prepared according to the microarray manufacturer's protocol and hybridized to human genome U133A 2.0 arrays (Affymetrix). The microarray data files were loaded into Rosetta Resolver software for analysis, and the intensity values for all probe sets were normalized using the Resolver's Experimental Definition. Clustering analysis within Resolver used the Agglomerative algorithm and Pearson correlation for the similarity measure, using genes that had a 1.5-fold change or higher in 1 treatment condition. Only differences with a p-value less than 0.001 are shown. For the pathway analysis, a 1.5-fold cut-off was applied and a 5% false discovery rate was used for p-value cut-off (See, Benjamini, Y. & Hochberg, Y., "Controlling the false discovery rate: a practical and powerful approach to multiple testing," *J R Statist Soc B* 57, 289-300 (1995)).

Mass Spectrometric Analysis of Immunoprecipitated Proteins

Endogenous Bcl-X$_L$ and Mcl-1 were immunoprecipitated from HCT116 cells. Samples to be processed for mass spectrometry were loaded into every other well of a 10-well×1 mm 4-12% Bis/Tris gel (Invitrogen) to reduce lateral contamination. The gels were run at a constant 200 V in MOPS running buffer for 45-60 minutes, then fixed in a solution of 50% methanol, 7% acetic acid for 15 minutes. After rinsing in water, the gels were treated with Sypro Ruby protein gel stain (Invitrogen) for 3 hr at room temperature. Once completed, the gels were destained in a solution of 10% methanol, 7% acetic acid for 10 minutes followed by washing and incubation in water for 30 minutes Protein bands were subsequently imaged on a Fuji imager using the green channel.

Each lane on the gel was manually cut into 24 equally-sized pieces, placed into a 96-well plate and minced. The minced gel pieces were subjected to in-gel tryptic digestion at 37° C. for 5 hr using a Perkin-Elmer MassPrep unit and sequencing grade modified trypsin (6 ng/μL). The extracted peptides for each sample were lyophilized prior to resuspension in 10 μL of a solution of 5% acetonitrile, 0.1% formic acid. 9.5 μL of the resuspended samples were injected onto a 15 cm analytical capillary column (I.D. 75 μm, 5μ particle size, 200 Å pore size) packed with Michrom C18AQ magic reversed-phase resin. The peptides were eluted using an Eiksigent nano-LC unit in a 35 minute linear gradient (15 to 35% acetonitrile in 0.1% formic acid). Hydrophobic peptides were subsequently removed by increasing the acetonitrile composition from 35% to 80% over the next 5 minutes. The eluent was directed into the orifice of a linear trap quadrupole (LTQ) mass spectrometer (ThermoFisher, Waltham, Mass.). Scans were collected in data-dependent double-play mode for the duration of the chromatographic separation.

Each LC-MS/MS data file was searched using Mascot Daemon v.2.2 against the NCBI non-redundant database restricted to the mammalian taxonomy. Peptides of 2+ to 3+ charge state were searched, with a maximum of 2 missed trypsin cleavages, carboxyamidomethyl as a fixed modification, oxidized methionine as a variable modification and a mass window of +1.2 Da for intact peptides and +0.8 Da for ions generated from tandem mass spectrometry. The Mascot search results for each data file were compiled by gel lane in Scaffold v.1.0 using the MudPIT compilation feature to yield protein identifications by treatment.

An interactome map of the Bcl-2 network was constructed manually using Ingenuity Pathway Analysis software (Ingenuity Systems Redwood City, Calif.). The composite of all protein identifications returned from Bcl-$X_L$ immunoprecipitates under all treatment conditions was applied to the Bcl-2 network map. Mcl-1 immunoprecipitates were analyzed similarly.

Results

VX-680/MK-0547 and ABT-263 Elicit Synergistic Cytotoxicity

Figure 8:
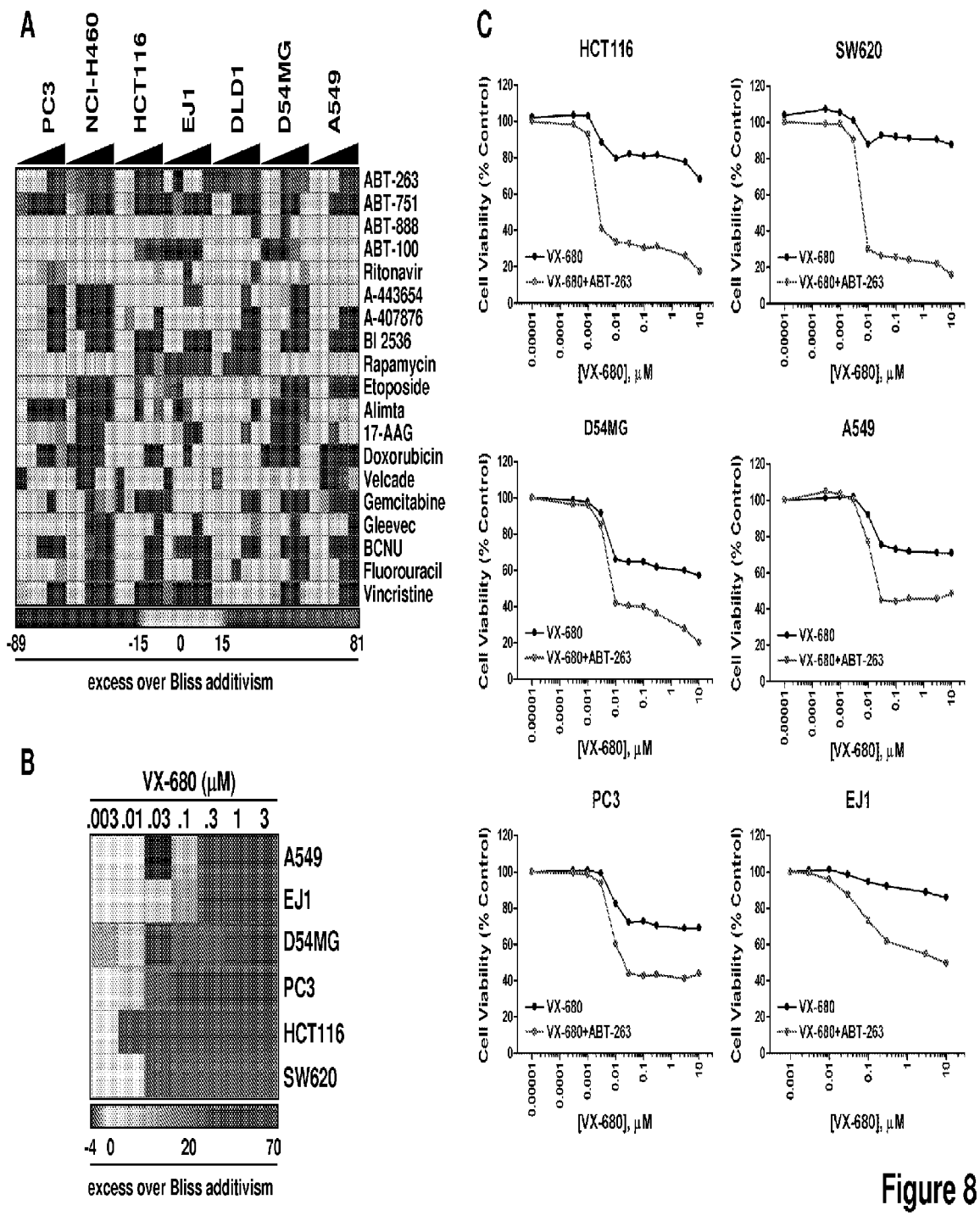
FIG. 8 shows that the BH3 mimetic ABT-263 and the pan-Aurora inhibitor VX-680 are synergistically lethal.

Small-molecule inhibitors that specifically target the Aurora family of serine/threonine kinases are under clinical evaluation as monotherapy and will no doubt be combined with other chemotherapeutic agents. To experimentally identify agents that could be therapeutically combined with Aurora Kinase inhibitors, VX-680, a pan-Aurora inhibitor, was screened in combination with 19 clinical and experimental cancer therapeutics for their effect on cell viability. A unique synergistic activity was observed when VX-680 was combined with ABT-263 (FIG. 8A), an orally bioavailable, small-molecule BH3 mimetic that inhibits Bcl-$X_L$, Bcl-2, and Bcl-w (FIG. 8A). Bliss analysis showed that VX-680 was synergistic with ABT-263 in tumor cell lines irrespective of histological type (e.g., D54MG (glioma), NCI-H460 and A549 (lung carcinoma), PC3 (prostate carcinoma), EJ1 (bladder carcinoma), HCT116, DLD1, and SW620 (colon carcinoma), and 786-O (renal carcinoma); FIG. 8A-B and data not shown), indicating that the synergy observed for these two classes of oncology drugs may reflect a molecular susceptibility pervasive in cancer cells. The targets/mechanisms of action of each of the 19 clinical and experimental cancer therapeutics and the corresponding dose responses for the combination screen is summarized in Table A, below.

TABLE A

| Compound | Target/MOA | 6-point dose response (μM) | | | | | |
|---|---|---|---|---|---|---|---|
| | | 1 | 2 | 3 | 4 | 5 | 6 |
| ABT-263 | Bcl-XL/-2 | 0 | 0.062 | 0.19 | 0.56 | 1.7 | 5.0 |
| ABT-751 | β-tubulin | 0 | 0.062 | 0.19 | 0.56 | 1.7 | 5.0 |
| ABT-888 | PARP | 0 | 0.062 | 0.19 | 0.56 | 1.7 | 5.0 |
| ABT-100 | farnesyltransferase | 0 | 0.062 | 0.19 | 0.56 | 1.7 | 5.0 |
| Ritonavir | CYP3A4 | 0 | 0.062 | 0.19 | 0.56 | 1.7 | 5.0 |
| A-443654 | Akt | 0 | 0.012 | 0.037 | 0.11 | 0.33 | 1.0 |
| A-407876 | histone deacetylase | 0 | 0.012 | 0.037 | 0.11 | 0.33 | 1.0 |
| BI 2536 | Plk1 | 0 | 0.062 | 0.19 | 0.56 | 1.7 | 5.0 |
| Rapamycin | mTORC1 | 0 | 0.062 | 0.19 | 0.56 | 1.7 | 5.0 |
| Etoposide | topoisomerase II | 0 | 0.062 | 0.19 | 0.56 | 1.7 | 5.0 |
| Alimta | thymidylate synthase | 0 | 0.012 | 0.037 | 0.11 | 0.33 | 1.0 |
| 17-AAG | Hsp90 | 0 | 0.012 | 0.037 | 0.11 | 0.33 | 1.0 |
| Doxorubicin | DNA alkylator | 0 | 0.012 | 0.037 | 0.11 | 0.33 | 1.0 |
| Velcade | proteasome | 0 | 0.0062 | 0.019 | 0.056 | 0.17 | 0.50 |
| Gemcitabine | nucleoside analog | 0 | 0.0025 | 0.0074 | 0.022 | 0.067 | 0.20 |
| Gleevec | Abl | 0 | 0.37 | 1.1 | 3.3 | 10 | 30 |
| BCNU | DNA alkylator | 0 | 0.37 | 1.1 | 3.3 | 10 | 30 |
| Fluorouracil | thymidylate synthase | 0 | 0.12 | 0.37 | 1.1 | 3.3 | 10 |
| Vincristine | tubulin | 0 | 0.00062 | 0.0019 | 0.0056 | 0.017 | 0.050 |

Figure 9:
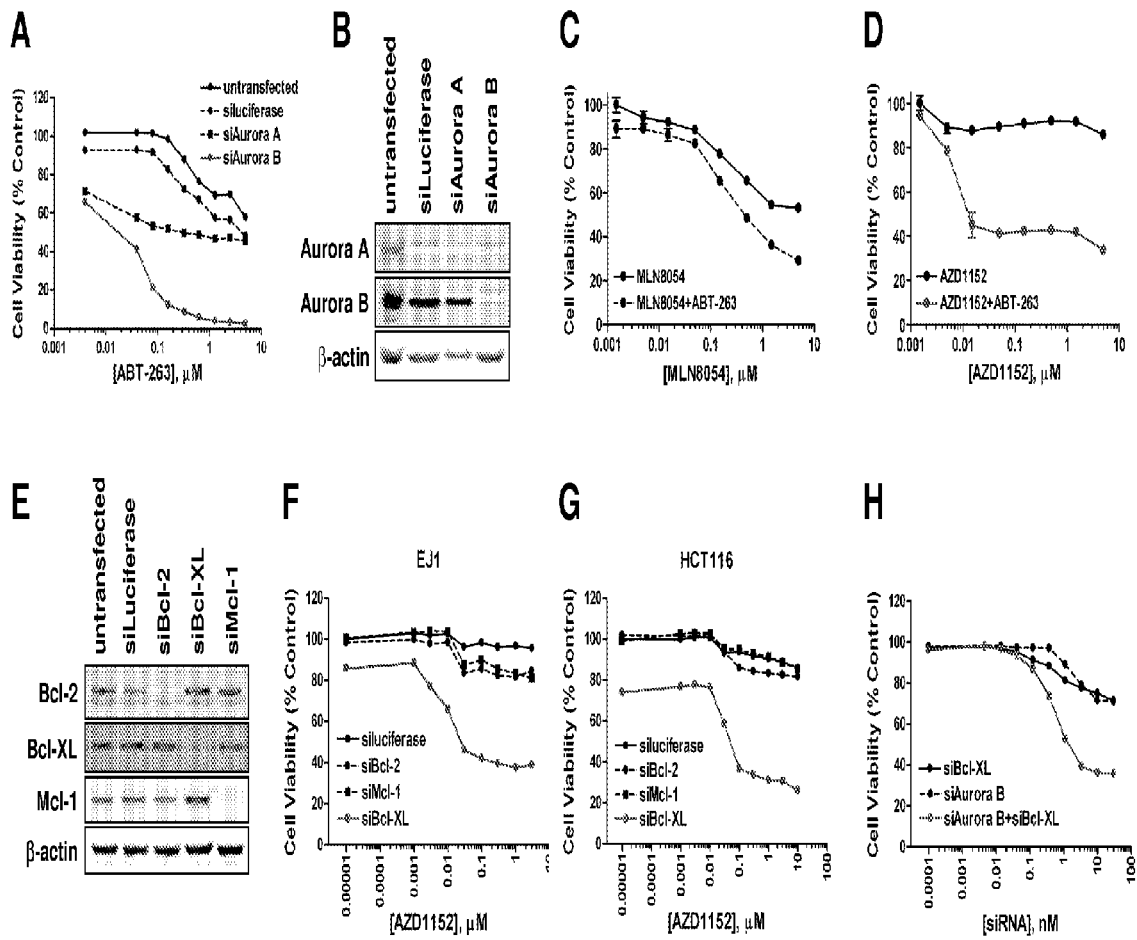
FIG. 9 shows that inhibition of Aurora B and Bcl-$X_L$ is sufficient for synergistic cytotoxicity.

The Synergistic Activity of VX-680 and ABT-263 can be Fully Ascribed to the Combined Inhibition of Aurora B and Bcl-$X_L$ VX-680 is a potent inhibitor of Aurora A, B, and C kinases with $K_{i(app)}$ values of 0.6, 18, and 4.6 nM, respectively. Inhibition of Aurora A results primarily in mitotic delay or arrest (See, Manfredi, M. G. et al., "Antitumor activity of MLN8054, an orally active small-molecule inhibitor of Aurora A kinase," *Proc Natl Acad Sci USA* 104, 4106-11 (2007); whereas inhibition of Aurora B produces gross polyploidization (See, Wilkinson, R. W. et al., "AZD1152, a selective inhibitor of Aurora B kinase, inhibits human tumor xenograft growth by inducing apoptosis," *Clin Cancer Res.* 13, 3682-8 (2007)). It was, therefore, important to distill from the pan-Aurora profile of VX-680 the Aurora Kinase activity that would suffice for synergy with ABT-263. Likewise, ABT-263 inhibits Bcl-$X_L$, Bcl-2, and Bcl-w with similar potencies, displaying K, values of and nM, respectively, and presents a similar complication. Therefore, these activities were deconvoluted to identify the activities that were sufficient for synergy using both siRNA and selective small-molecules. When added in combination with ABT-263, Aurora B, but not Aurora A, siRNA was synergistically antiproliferative in combination with ABT-263, though both siRNAs efficiently knocked down their respective targets (FIGS. 9A and 9B). MLN8054, a small-molecule inhibitor of Aurora A, showed no synergy in combination with ABT-263 (FIG. 9C) at Aurora A-selective concentrations (<5 μM) (See, Manfredi, M. G. et al., "Antitumor activity of MLN8054, an orally active small molecule inhibitor of Aurora A kinase," *Proc Natl Acad Sci USA* 104, 4106-11 (2007) and Li, J. et al., "Inhibition of Aurora B kinase sensitizes a subset of human glioma cells to TRAIL concomitant with induction of TRAIL-R2," *Cell Death Differ*, Epub ahead of print (2008)). In contrast, synergy was observed when ABT-263 was combined with the Aurora B-selective inhibitor, AZD1152 (See, Wilkinson, R. W. et al., "AZD1152, a selective inhibitor of Aurora B kinase, inhibits human tumor xenograft growth by inducing apoptosis," *Clin Cancer Res*. 13, 3682-8. (2007) and Mortlock, A. A. et al., "Discovery, synthesis, and in vivo activity of a new class of pyrazoloquinazolines as selective inhibitors of aurora B kinase," *J Med Chem* 50, 2213-24 (2007)) (FIG. 9D).

While ABT-263 inhibits Bcl-2, Bcl-$X_L$, and Bcl-w, it is relatively inactive vs. other anti-apoptotic members of the Bcl-2 family, such as Mcl-1 and Bcl-A1. Because Bcl-2 and Bcl-$X_L$ are commonly expressed in many human cancer cells, siRNA was used to determine which of the two ABT-263 targets, when inhibited, would phenocopy the synergistic activity observed for ABT-263 in combination with AZD1152. When transfected into cancer cells of different tumor origin (HCT116, DLD1, EJ1, PC3, D54MG), Bcl-$X_L$, but not luciferase, Bcl-2, or Mcl-1 siRNA exhibited a synergistic inhibition of cell growth in combination with AZD1152 (FIG. 9E-FIG. 9G and data not shown). Therefore, inhibition of Bcl-$X_L$, but not Bcl-2, cooperates with Aurora B inhibition to induce cell death in these cell lines. Bcl-$X_L$ and Aurora B siRNAs were also synergistically antiproliferative (FIG. 9H). Collectively, these data indicate that the synergistic activity of VX-680 and ABT-263 can be fully ascribed to inhibition of Aurora B and Bcl-$X_L$.

ABT-263 Triggers Rapid Apoptosis in Polyploid Cells.

Figure 10:
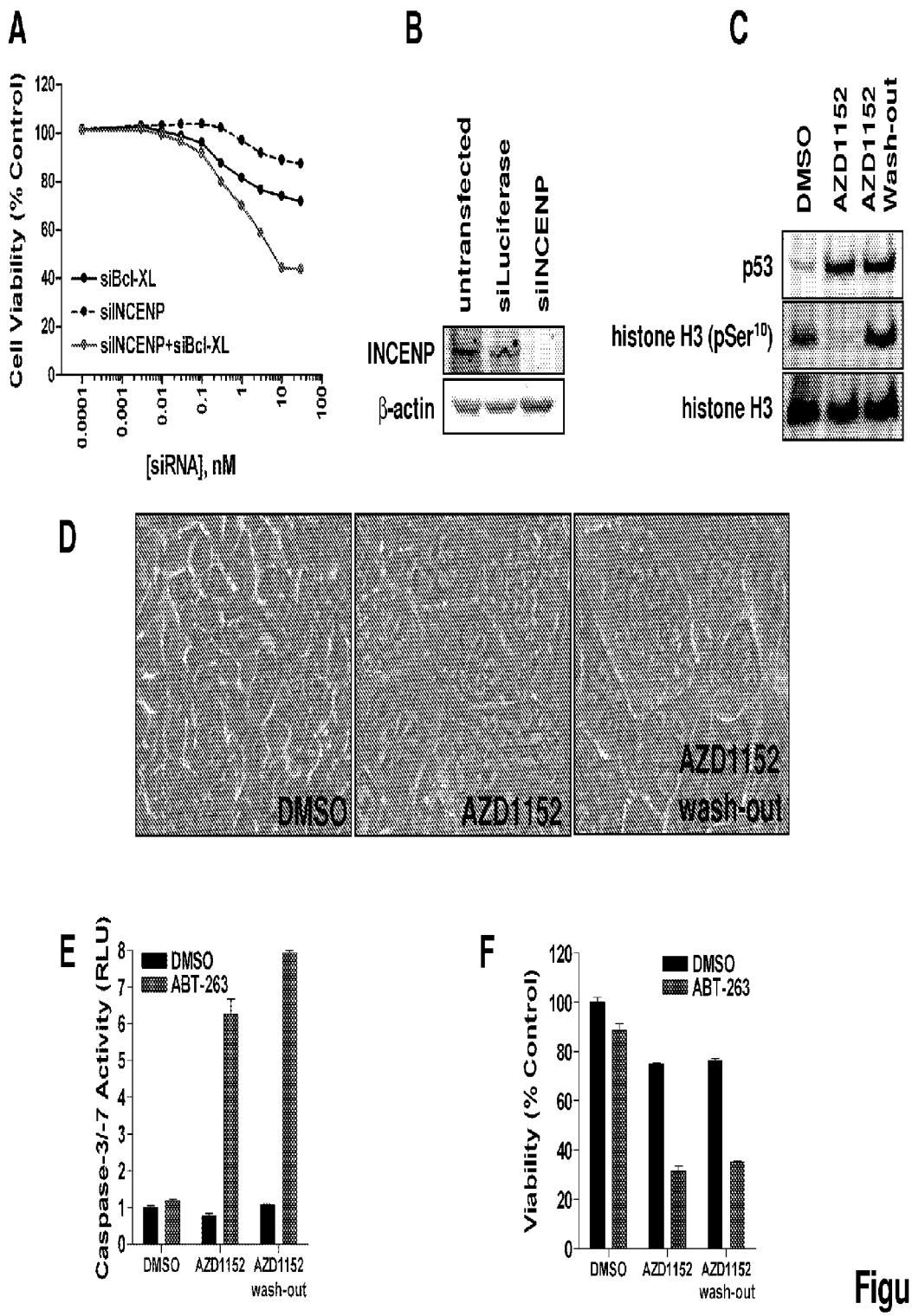
FIG. 10 shows that polyploidization renders cells Bcl-$X_L$ dependent.

As polyploidy represents the ultimate cell fate associated with sustained inhibition of Aurora B, the inventors set out to determine whether Bcl-$X_L$ inhibition and polyploidization were synergistically cytotoxic, independently of Aurora B. The CPC is an epistasis group comprising Aurora B, survivin, INCENP, and borealin, and is the core of the mitotic spindle assembly checkpoint (See, Ruchaud, S., Carmena, M. & Earnshaw, W. C., "Chromosomal passengers: conducting cell division," *Nat Rev Mol Cell Biol* 8, 798-812 (2007)). Disruption of the CPC results in cytokinesis failure and polyploidy (See, Honda, R., Körner, R. & Nigg, E. A., "Exploring the functional interactions between Aurora B, INCENP, and survivin in mitosis," *Mol Biol Cell* 14, 3325-41 (2003)). In accordance with INCENP's role to safeguard against polyploidy (See, Uren, A. G. et al., "Survivin and the inner centromere protein INCENP show similar cell-cycle localization and gene knockout phenotype," *Curr Biol* 10, 1319-28 (2000)). INCENP siRNA induced morphological hallmarks of polyploidy, such as grossly enlarged cells with multiple micronuclei (data not shown). Knockdown of INCENP was synergistically antiproliferative with Bcl-$X_L$ knockdown (FIG. 10A-B), suggesting that inhibition of Bcl-XL is deleterious for polyploid cells. However, targeting INCENP with siRNA also delocalizes Aurora B and inhibits its activity (See, Klein, U. R., Nigg, E. A. & Gruneberg, U., "Centromere targeting of the chromosomal passenger complex requires a ternary subcomplex of Borealin, Survivin, and the N-terminal domain of INCENP," *Mol Biol Cell* 17, 2547-58 (2006)). Therefore, the effect of INCENP siRNA cannot be fully dissociated from disruption of Aurora B. To conclusively determine whether polyploidy per se was sufficient to sensitize cells to Bcl-$X_L$ inhibition, cells were treated with AZD1152 to induce polyploidy, washed out the drug, and the polyploid cells cultured until Aurora B activity was restored. Polyploidy was evidenced by elevated expression of p53 (FIG. 10C), a surrogate for polyploidization in cell harboring wildtype p53 (See, Gizatullin, F. et al., "The Aurora Kinase inhibitor VX-680 induces endoreduplication and apoptosis preferentially in cells with compromised p53-dependent postmitotic checkpoint function," *Cancer Res*. 66, 7668-77. (2006), Li, J. et al., "Inhibition of Aurora B kinase sensitizes a subset of human glioma cells to TRAIL concomitant with induction of TRAIL-R2," *Cell Death Differ*, Epub ahead of print (2008) and Kojima, K., Konopleva, M., Tsao, T., Nakakuma, H. & Andreeff, M., "Concomitant inhibition of Mdm2-p53 interaction and Aurora Kinases activates the p53-dependent postmitotic checkpoints and synergistically induces p53-mediated mitochondrial apoptosis along with reduced endoreduplication in acute myelogenous leukemia," *Blood* 112, 2886-95 (2008)) and by the gross morphological increase in cell size and multinucleation (FIG. 10D). Following AZD1152 wash-out, histone H3 phosphorylation returned to untreated levels indicating that Aurora B activity had been fully restored (FIG. 10C) in polyploid cells (FIG. 10D). ABT-263 induced Caspase-3 activity and loss of viability in polyploid cells, but not diploid cells, independently of the activation status of Aurora B (FIG. 10E-F). These data suggest that acute induction of polyploidy renders cell survival dependent on the anti-apoptotic activity of Bcl-$X_L$.

Polyploidization Shifts the Survival Burden to Bcl-$X_L$

Figure 11:
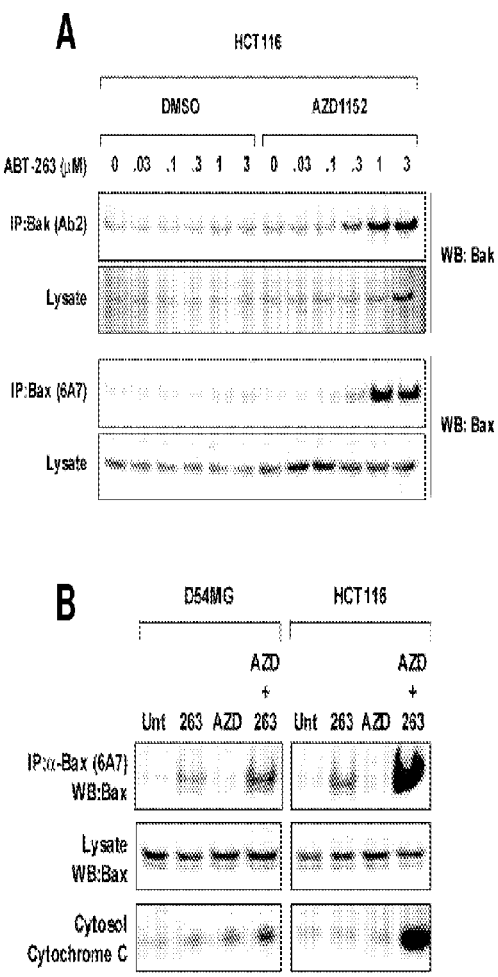
FIG. 11 shows that modulation of the Bcl-2 network during polyploidization. HCT116 cells (FIG. 11A) were treated with DMSO or 200 nM AZD1152 for 72 hours followed by 2 hours with 1 µM ABT-263. Conformationally active BAK or BAX was immunoprecipitated and detected by immunoblotting. D54MG and HCT116 cells (FIG. 11B) were treated DMSO or 200 nM AZD1152 for 72 hours prior to the addition of 1 µM ABT-263 for 4 hours. Conformationally active BAK or BAX was immunoprecipitated and detected by immunoblotting (top and middle panel). Cell lysates were also fractionated and Cytochrome C release into the cytosolic fraction was detected by immunoblotting. HCT116, SW620, and D54MG cells (FIG. 11C) were treated with DMSO (untreated) or 200 nM AZD1152 (AZD1152) for 72 hours and the expression of Bcl-2 network components were detected by immunoblotting (FIG. 11D-FIG. 11E) HCT116 cells were treated as in FIG. 11B. Endogenous Bcl-$X_L$ and Mcl-1 were immunoprecipitated, and the Bcl-2 network components in the immunecomplexes were detected by immunoblotting.
Figure 11:
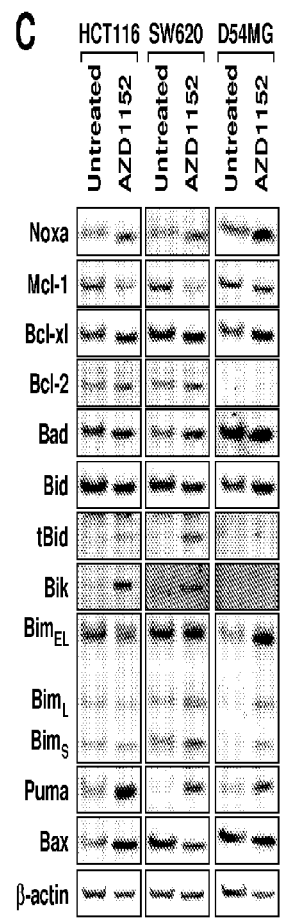
Figure 11:
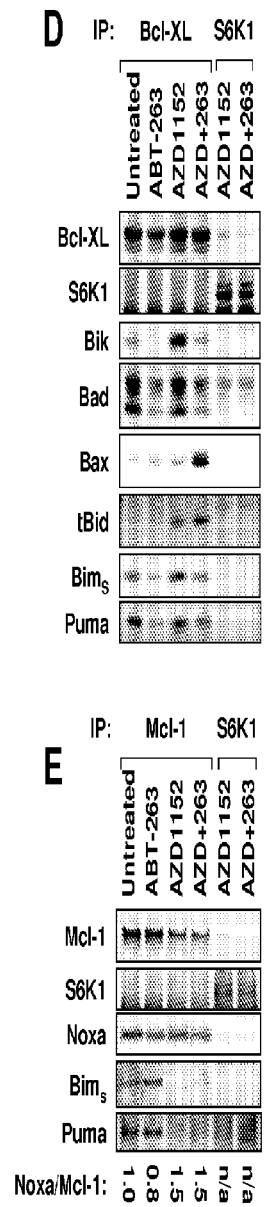
Figure 14:
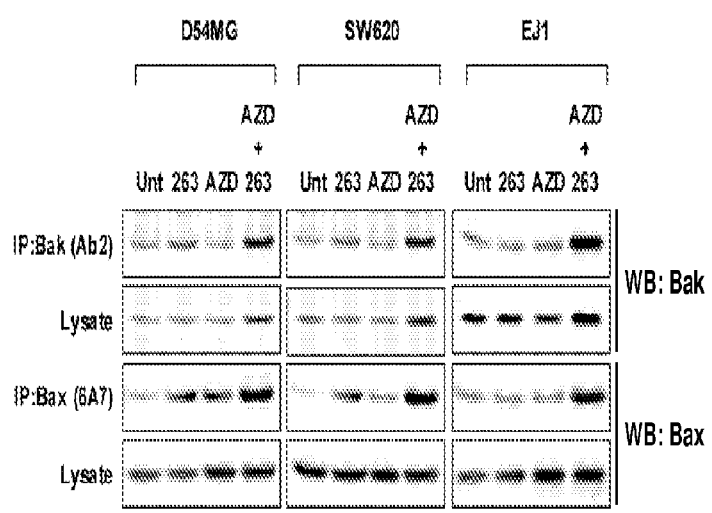
FIG. 14 BAK and BAX activation in tumor cell lines. D54MG, SW620, and EJ1 cells were treated as in FIG. 17B. Conformationally active BAK and BAX was immunoprecipitated and detected by immunoblotting.

The multidomain apoptotic proteins BAX and BAK together constitute an obligatory portal to apoptosis (See, Wei, M. C. et al., "Proapoptotic BAX and BAK: a requisite gateway to mitochondrial dysfunction and death," *Science* 292, 727-30 (2001) and Zong, W. X., Lindsten, T., Ross, A. J., MacGregor, G. R. & Thompson, C. B., "BH3-only proteins that bind pro-survival Bcl-2 family members fail to induce apoptosis in the absence of BAX and BAK," *Genes Dev* 15, 1481-6 (2001)). To begin to shed light on the mechanisms through which Bcl-$X_L$ neutralization elicits cell death in polyploid cells, the activation of BAX and BAK in cells rendered polyploid with AZD1152 using antibodies that selectively recognize the active BAX and BAK conformers was examined. Addition of ABT-263 to polyploid HCT116, D54MG, SW620, and EJ1 cells rapidly and synergistically induced BAX and BAK activation (FIG. 11A and FIG. 14). The activation of BAX and BAK was followed by mitochondrial release of cytochrome C into the cytosol, a decisive event in the commitment to apoptosis (FIG. 11B).

Figure 15:
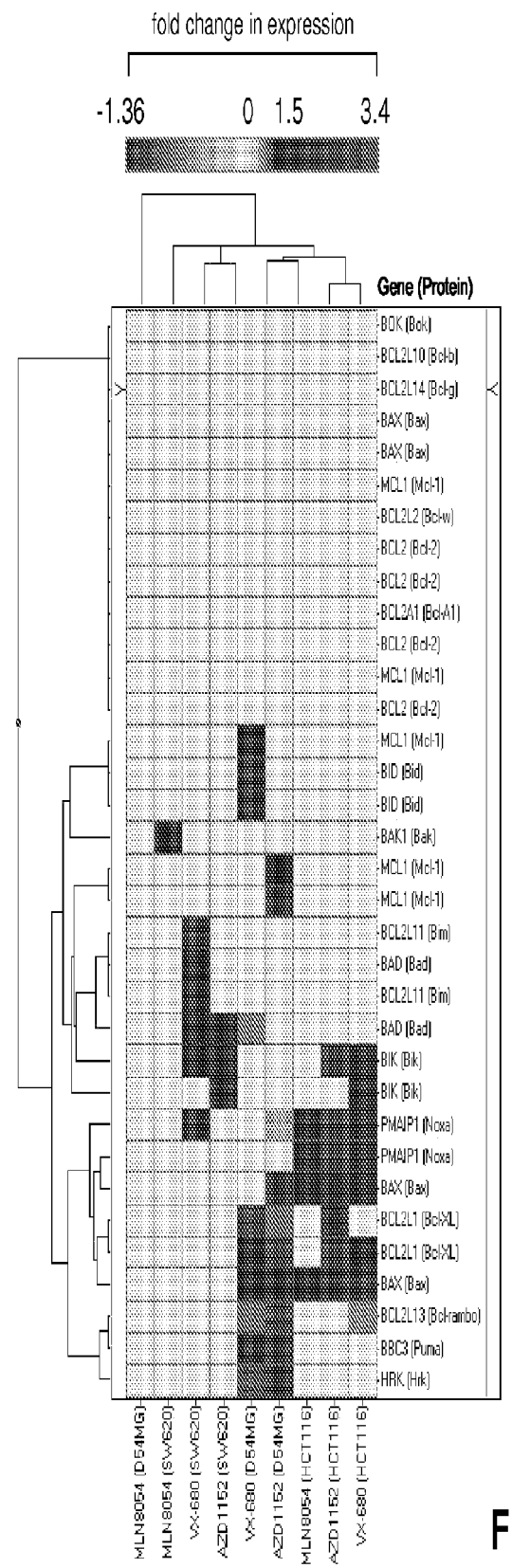
FIG. 15 shows gene expression changes in the Bcl-2 network. D54MG, SW620, and HCT116 cells were treated for 72 hours with 200 nM AZD1152, 250 nM MLN8054, or 1 µM VX-680. These treatments result in the following cellular Aurora selectivities: Aurora B, Aurora A, or pan-Aurora, respectively. Gene expression changes in the Bcl-2 network were detected by microarray. These data were hierarchically clustered using a correlation similarity measure using SPOT-FIRE® (TIBCO®) data analysis software.

The pro-apoptotic function of BAX and BAK is normally inhibited by anti-apoptotic members of the Bcl-2 family such as Bcl-$X_L$ and Mcl-1, and it is the balance of interactions between BH3-only and multidomain proteins that sets the threshold for apoptosis through the intrinsic pathway (See, Kim, H. et al., "Hierarchical regulation of mitochondrion-dependent apoptosis by BCL-2 subfamilies," *Nat Cell Biol* 8, 1348-58 (2006) and Willis, S, N. et al., "Apoptosis initiated when BH3 ligands engage multiple Bcl-2 homologs, not BAX or BAK," *Science* 315, 856-9 (2007)). In contrast to what was observed in polyploid cells, neutralization of Bcl-$X_L$ is not normally sufficient to trigger apoptosis in diploid or aneuploid cells (FIG. 8C). To elucidate how polyploidization engages elements of the apoptotic machinery and renders polyploid cell survival Bcl-$X_L$-dependent, the Bcl-2 network was monitored at the mRNA and protein level in response to polyploidization. Hierarchical clustering of Bcl-2 network genes indicated that the transcriptional profiles of polyploidization (VX-680 and AZD1152) were consistently most similar compared to Aurora A inhibition (MLN8054), though they differed across cell lines (FIG. 15). At the protein level, a number of pro-apoptotic BH3-only proteins were upregulated following polyploidization (FIG. 11C). An increase in PUMA and NOXA was a conserved effect across cell lines; whereas, tBID, BIK, BIM, and BAX increased in a cell line-dependent manner. Though only subtle changes in expression were observed for Bcl-2 and Bcl-$X_L$, Mcl-1 was significantly reduced in HCT116, SW620, and EJ1 cells (FIG. 11C and data not shown). NOXA binds to and inhibits the anti-apoptotic function of Mcl-1 (See, Chen, L. et al., "Differential targeting of prosurvival Bcl-2 proteins by their BH3-only ligands allows complementary apoptotic function," *Mol Cell* 17, 393-403 (2005)). Therefore, the upregulation of NOXA in D54MG is predicted to antagonize Mcl-1, though the abundance of Mcl-1 in D54MG cells was not reduced (FIG. 11C). Collectively, polyploidization induced effectors of apoptosis while compromising Mcl-1 function. As cell viability is maintained during this period of polyploidization, it was inferred that the burden to support viability is shifted from Mcl-1 to Bcl-$X_L$.

Figure 16:
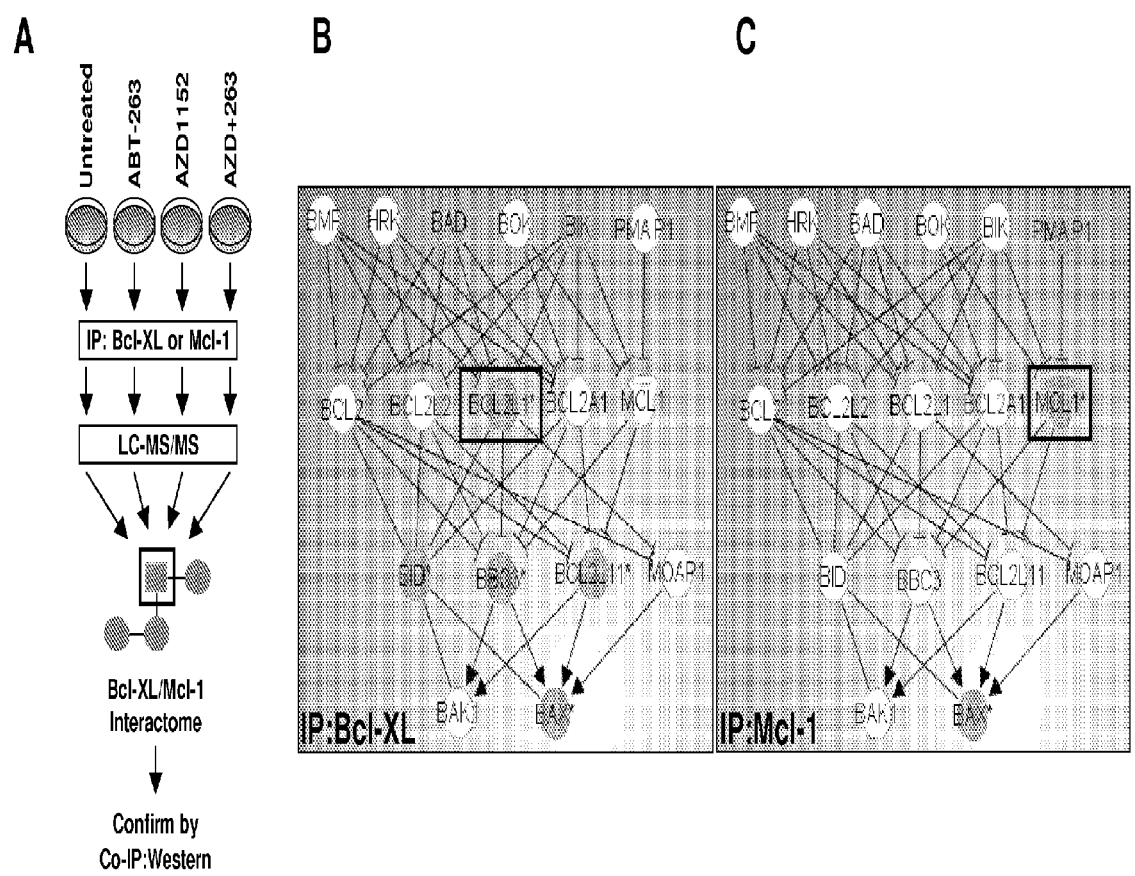
FIG. 16 shows the identification of Bcl-$X_L$ and Mcl-1 interactomes.

While gene expression represents one level at which the Bcl-2 network is regulated, the collection of binding events between pro- and anti-apoptotic proteins ultimately determines the balance between survival and apoptosis. The Bcl-$X_L$ and Mcl-1 interactomes were empirically defined and monitored the effect of polyploidization on these interactions. HCT116 cells were treated with DMSO, ABT-263, AZD1152, or AZD1152 and ABT-263. Endogenous Bcl-$X_L$ or Mcl-1 was then immunoprecipitated, and the immune complexes were analyzed by in-gel tryptic digestion and LC-MS/MS. The protein identifications were compiled from all treatments yielding a composite interactome that represents all Bcl-$X_L$ and Mcl-1 interactions detected (FIG. 16). Interactions were subsequently confirmed by co-immunoprecipitation and immunoblotting under each treatment condition (FIG. 11D-E). None of the coimmunoprecipitated proteins were detected in anti-S6K1 immunoprecipitates using an IgG isotype-matched antibody (FIG. 11D-E), highlighting the specificity of these interactions. In polyploid cells (AZD1152), the interactions of Bik and tBid with Bcl-$X_L$ were increased while the binding of BAD, BIM, BAX, and PUMA was unchanged (FIG. 11E) indicating that Bcl-$X_L$ was increasingly burdened by pro-apoptotic proteins upon polyploidization. Consistent with the reduction of Mcl-1 protein level, a reduced amount of Mcl-1 was captured by immunoprecipitation in polyploid cells (FIG. 11E). In addition, there was a stoichiometric increase in NOXA binding during polyploidization (FIG. 11E). Furthermore, the association of Mcl-1 with Bim and Puma was significantly attenuated in polyploid cells (FIG. 11E), suggesting that the reduction of Mcl-1 and concomitant increase of NOXA was sufficient to partially neutralize Mcl-1.

Figure 12:
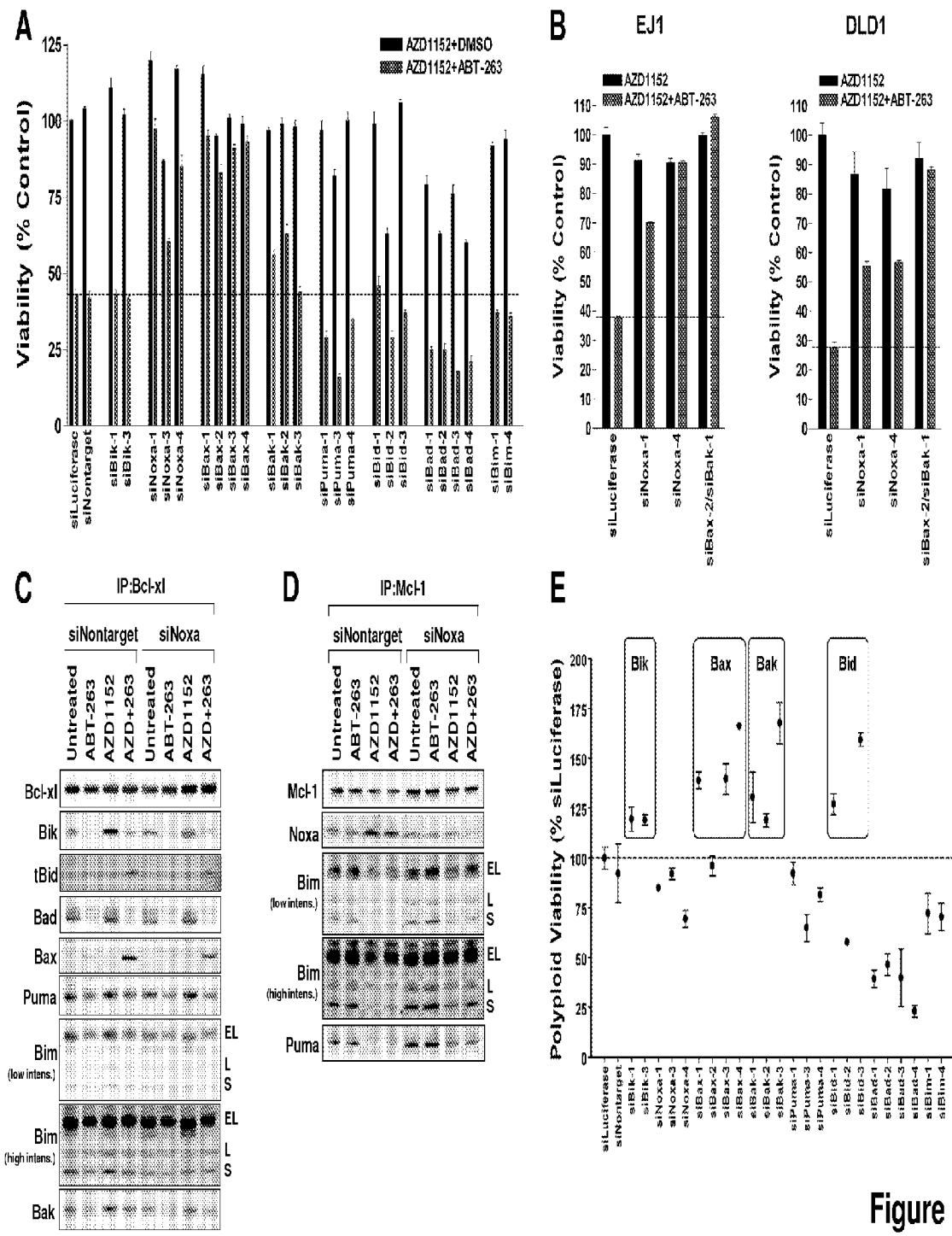
FIG. 12 shows that elements of Bcl-2 network are required for Bcl-$X_L$ "addiction" in polyploid cells and for polyploidization-mediated apoptosis.
Figure 17:
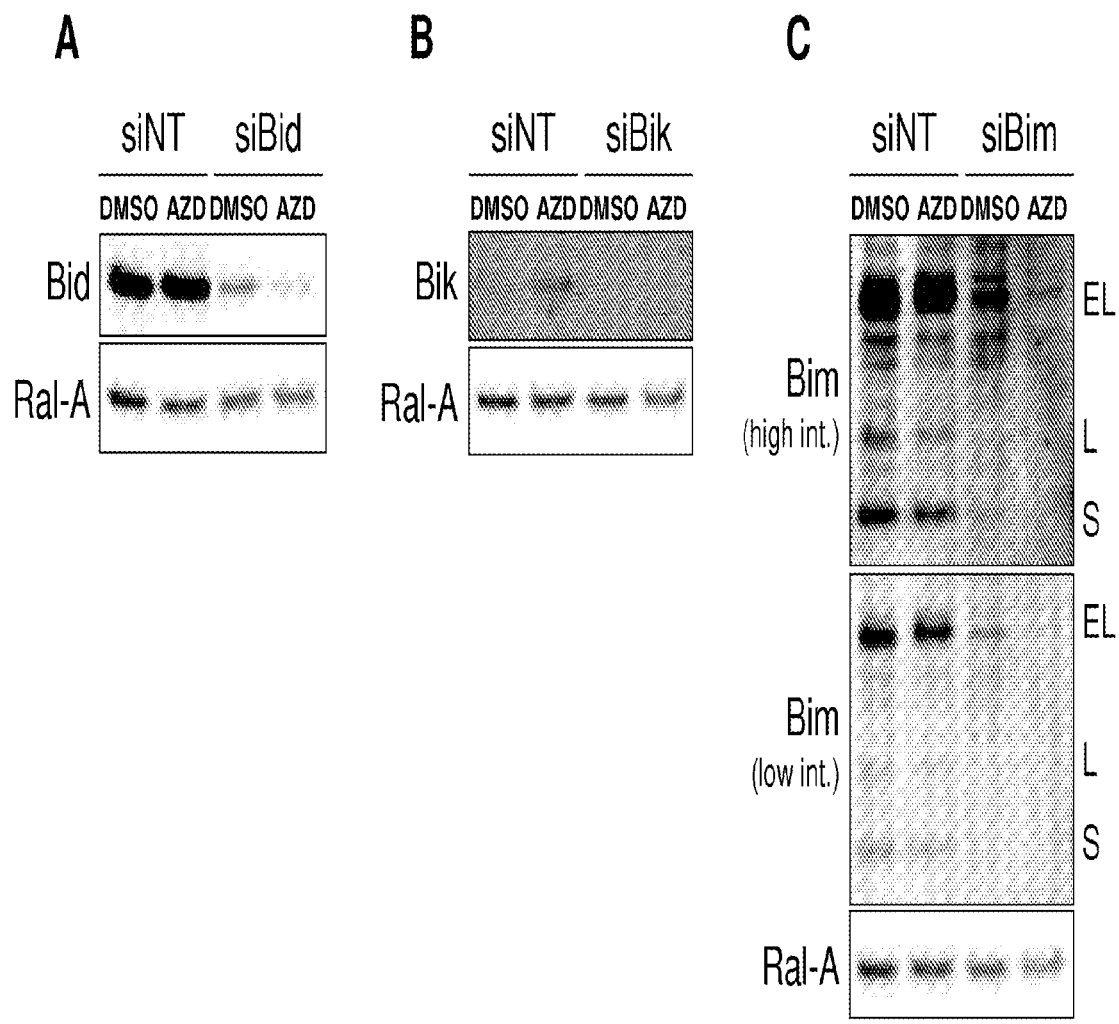
FIG. 17A shows a schematic of the workflow to identify Bcl-$X_L$ and Mcl-1 interactors is shown. HCT116 cells are either untreated or treated with 200 nM AZD1152, 1 µM ABT-263 or the combination. Endogenous Bcl-$X_L$ and Mcl-1 is immunoprecipitated, and immunoprecipitated proteins are subjected to in-gel tryptic digestion and LC-MS/MS. The protein identified from all treatment conditions were consolidated into a single list as Bcl-$X_L$ and Mcl-1 interactomes and applied to a manually constructed Bcl-2 network map. Interactions are indicated in green. Interactome components were subsequently confirmed by co-immunoprecipitation and immunoblotting (FIG. 17B and FIG. 17C) Bcl-$X_L$ and Mcl-1 interactomes.

Identification of Bcl-2 Network Components Required for Bcl-$X_L$/Aurora B Inhibitor Synergy Although multiple Bcl-2 family proteins were modulated by polyploidization at the levels of expression and/or protein-protein interaction, it was unclear which, if any, were essential for sensitization of polyploid cells to Bcl-$X_L$ inhibition. An siRNA screen was carried out emphasizing the Bcl-$X_L$ and Mcl-1 interactomes, to identify elements of the Bcl-2 network that, upon knockdown, could rescue viability in the presence of dual inhibition of Aurora B and Bcl-$X_L$. Multiple siRNAs targeting NOXA, BAX, and to a lesser extent, those targeting BAK were found to rescue polyploid cells from ABT-263-mediated cell death (FIG. 12A and FIG. 17). In fact, siRNA-mediated depletion of NOXA and BAX in several cell lines rendered polyploid cells resistant to Bcl-$X_L$ inhibition (FIG. 12B and FIG. 17). These data imply causal roles for NOXA and BAX in the synergistic activity of Bcl-$X_L$ inhibition in polyploid cells.

Figure 19:
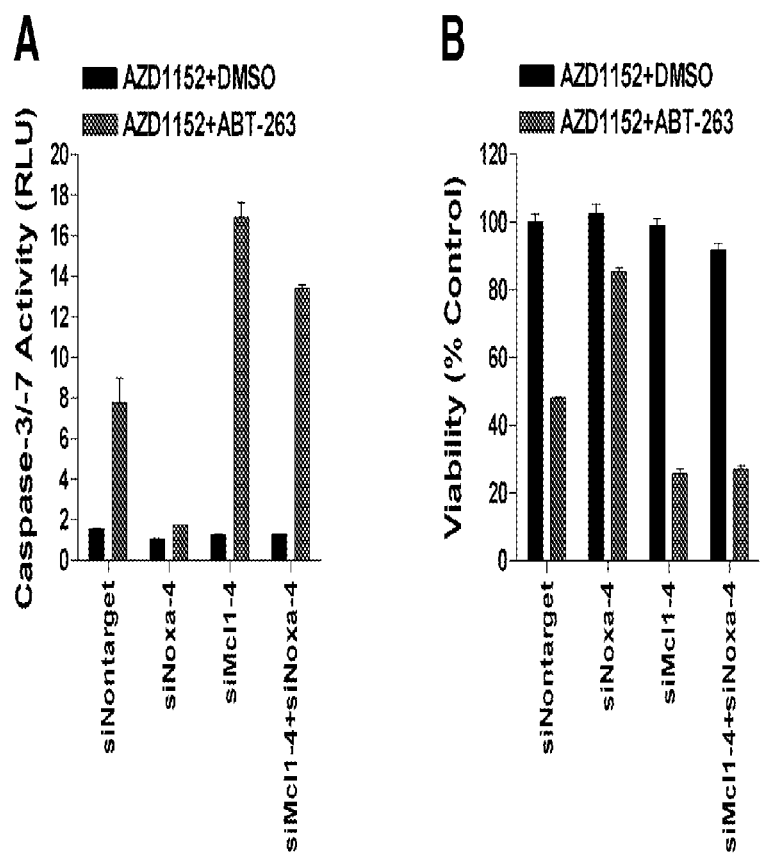
FIG. 19 shows that time-course of polyploidization-mediated apoptosis. HCT116 cells were treated with 200 nM AZD1152, and cell viability was determined over indicated time course.

To further understand how Noxa inhibition protects polyploid cells from ABT-263-mediated apoptosis, the Bcl-$X_L$ and Mcl-1 interactomes were compared before and after polyploidization in cells transfected with a control or NOXA siRNA. As before, a reduction of Mcl-1 protein and a stoichiometric increase in NOXA binding to Mcl-1 was observed in cells made polyploid using AZD1152 (FIG. 12D). Depletion of NOXA restored the binding of Puma and Bim to Mcl-1 in polyploid cells indicating that the capacity of Mcl-1 to bind pro-apoptotic effectors had been restored. Though it is sufficient to cause Bcl-$X_L$ dependence, the inhibition of Mcl-1 during polyploidization appears incomplete, as apoptosis induced by AZD1152/ABT-263 is augmented by Mcl-1 knockdown (FIG. 19).

Figure 18:
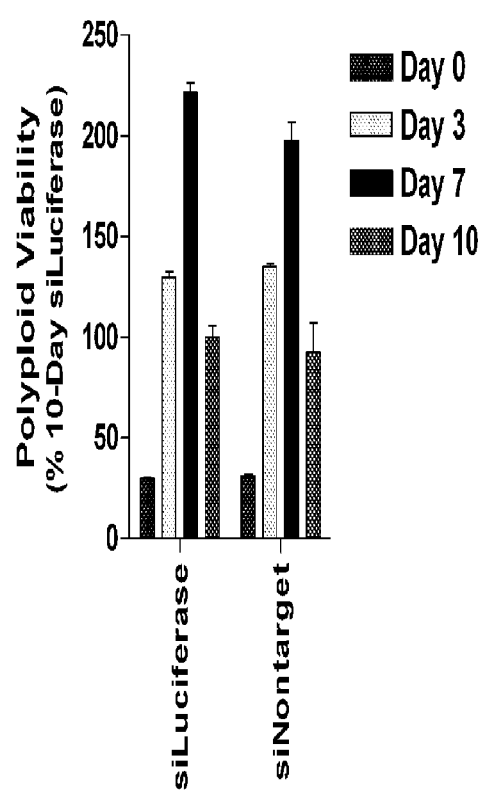
FIG. 18 shows that siRNA-mediated knockdown of Bcl-2 network components. HCT116 cells were transfected with siRNAs as indicated. 24 hours post-transfection, cells were treated with 200 nM AZD1152, and lysates were prepared 72 hours later and analyzed by immunoblotting. Ral-A serves as a loading control and siNT, non-targeted, control siRNA.

Polyploidization-Mediated Apoptosis Involves a Mechanism Distinct from Dual Aurora B/Bcl-$X_L$ Inhibition Cancer cells accumulate viable cell mass during polyploidization and continue to do so for up to a week after the addition of AZD1152. However, 10 days after the onset of polyploidy, viability sharply declines as cells succumb to the polyploidization process (FIG. 18). To determine whether apoptosis secondary to prolonged polyploidization engages the same, albeit delayed, apoptotic program as dual inhibition of Aurora B/Bcl-$X_L$, an additional siRNA rescue screen were performed to identify components of the Bcl-2 network that, when functionally disrupted, would preserve the long-term viability of polyploid cells (FIG. 12E). In contrast to the predominant requirement of BAX and NOXA for acute apoptosis induced by the AZD1152/ABT-263 combination, siRNAs against BAX and BAK confer similar degrees of protection, and siRNAs against BIK and BID, which were ineffective in the earlier rescue screen, protected cells from polyploidization-mediated loss of viability (FIG. 12E). Furthermore, depletion of NOXA failed to provide any protective effect in this setting (FIG. 12E).

ABT-263 Enhances the Efficacy of Aurora Kinase Inhibitors In Vivo

Figure 13:
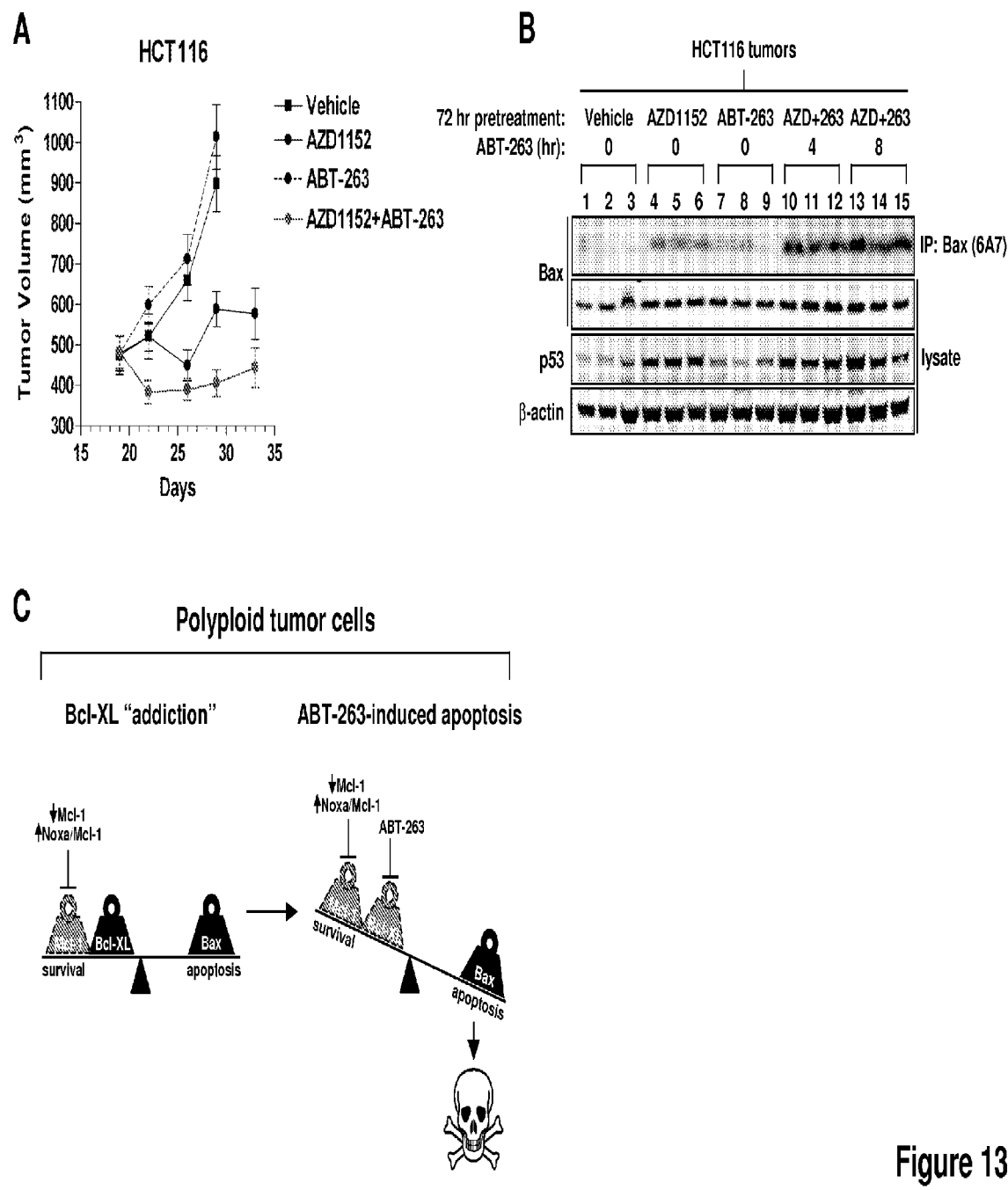
FIG. 13 shows that ABT-263 and AZD1152 produce synergistic tumor growth inhibition in vivo.

Although Aurora Kinase inhibitors have been shown to be efficacious in preclinical studies, targeting Bcl-$X_L$ in polyploid tumor cells may produce efficacy superior to Aurora Kinase inhibitors as monotherapy. This was assessed by comparing the antitumor efficacy of single agent AZD1152 treatment to the combination of AZD1152/ABT-263 in a stringent and therapeutically relevant setting: well-established, large tumors (~0.5 gram) and with the maximum tolerated dose of AZD1152 AZD1152 as a single agent produced significant tumor growth inhibition in the HCT116 colon carcinoma model, though tumors started to recover from therapy within one week (as evidenced by tumor regrowth). In contrast, the combination regimen of AZD1152/ABT-263 resulted in a rapid and more sustained tumor regression that persisted for at least 2 weeks (FIG. 13A). In tumors that were pretreated for 3 days with AZD1152, an induction in p53 was observed, a surrogate marker of polyploidization (FIG. 13B). The active BAX conformer was detected within 4 hours of ABT-263 treatment in tumors from AZD1152-treated mice, but not in naive tumors, reflecting the rapid onset of ABT-263-mediated apoptosis in polyploid tumor cells (FIG. 13B).

One skilled in the art would readily appreciate that the present disclosure is well adapted to carry out the objects and obtain the ends and advantages mentioned, as well as those inherent therein. The molecular complexes and the methods, procedures, treatments, molecules, specific compounds described herein are presently representative of preferred aspects, are exemplary, and are not intended as limitations on the scope of the disclosure. It will be readily apparent to one skilled in the art that varying substitutions and modifications may be made to the disclosure disclosed herein without departing from the scope and spirit of the disclosure.

All patents and publications mentioned in the specification are indicative of the levels of those skilled in the art to which the disclosure pertains. All patents and publications are herein incorporated by reference to the same extent as if each individual publication was specifically and individually indicated to be incorporated by reference. The disclosure illustratively described herein suitably may be practiced in the absence of any element or elements, limitation or limitations which is not specifically disclosed herein. Thus, for example, in each instance herein any of the terms "comprising," "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the disclosure claimed. Thus, it should be understood that although the present disclosure has been specifically disclosed by preferred aspects and optional features, modification and variation of the concepts herein disclosed may be resorted to by those skilled in the art, and that such modifications and variations are considered to be within the scope of this disclosure as defined by the appended claims.

What is claimed is:

1. A combination of therapeutic agents for use in treating a patient suffering from cancer, wherein said combination comprises:
   a) at least one polyploidy inducing agent for use in inducing polyploidization in one or more cancer cells in the patient; and
   b) at least one Bcl-2 family protein inhibitor having the following structure (II):

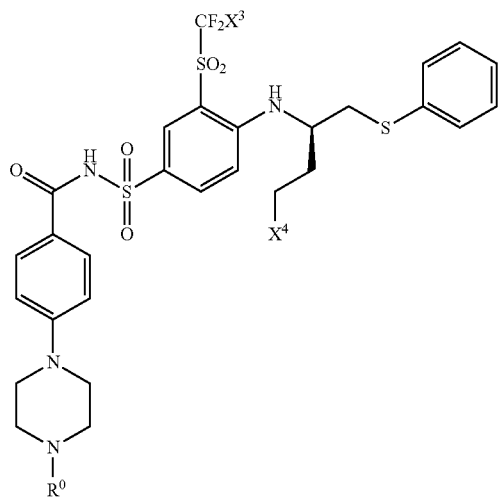

(II)

or a therapeutically acceptable salt thereof; wherein
$X^3$ is chloro or fluoro; and
(1) $X^4$ is azepan-1-yl, morpholin-1-yl, 1,4-oxazepan-4-yl, pyrrolidin-1-yl, $N(CH_3)_2$, $N(CH_3)(CH(CH_3)_2)$, 7-azabicyclo[2.2.1]heptan-1-yl or 2-oxa-5-azabicyclo[2.2.1]hept-5-yl; and
$R^0$ is

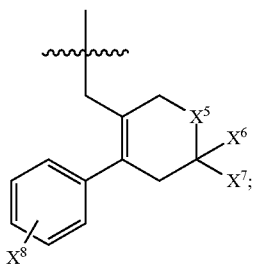

wherein $X^5$ is $CH_2$, $C(CH_3)_2$ or $CH_2CH_2$; $X^6$ and $X^7$ are both hydrogen or both methyl; and $X^8$ is fluoro, chloro, bromo or iodo; or, (2) $X^4$ is azepan-1-yl, morpholin-1-yl, pyrrolidin-1-yl, $N(CH_3)(CH(CH_3)_2)$, or 7-azabicyclo[2.2.1]heptan-1-yl; and
$R^0$ is

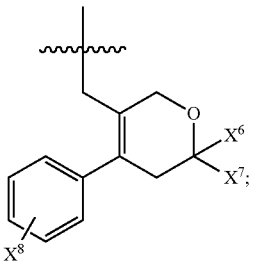

wherein $X^6$ and $X^7$ are both hydrogen or both methyl; and $X^8$ is fluoro, chloro, bromo or iodo; or,
(3) $X^4$ is $N(CH_3)_2$ or morpholin-1-yl; and
$R^0$ is

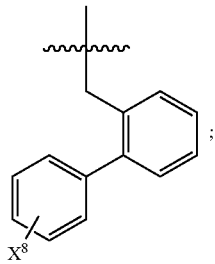

wherein $X^8$ is fluoro, chloro, bromo or iodo.

2. The combination of claim 1, wherein the at least one polyploidy inducing agent is an Aurora Kinase inhibitor.

3. The combination of claim 2, wherein the Aurora Kinase inhibitor is an Aurora Kinase B inhibitor.

4. The combination of claim 3, wherein the Aurora Kinase B inhibitor is VX-680 or AZD1152.

5. The combination of claim 1, wherein the Bcl-2 family protein inhibitor is ABT-263.

6. A method of treating a patient suffering from cancer, the method comprising the steps of:
   a) administering to a patient suffering from cancer a therapeutically effective amount of at least one polyploidy inducing agent; and
   b) administering to the patient a therapeutically effective amount of at least one Bcl-2 family protein inhibitor having the structure (11) of claim 1,
   wherein the cancer is a lymphoid malignancy of B-cell origin or a small cell lung cancer.

7. The method of claim 6, wherein the at least one polyploidy inducing agent is an Aurora Kinase inhibitor.

8. The method of claim 7, wherein the Aurora Kinase inhibitor is an Aurora Kinase B inhibitor.

9. The method of claim 8, wherein the Aurora Kinase B inhibitor is VX-680 or AZD1152.

10. The method of claim 6, wherein the Bcl-2 family protein inhibitor is ABT-263.

* * * * *

SEQUENCE LISTING

```
<160> NUMBER OF SEQ ID NOS: 10

<210> SEQ ID NO 1
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide probe
<220> FEATURE:
<221> NAME/KEY: MOD_RES
<222> LOCATION: 1
<223> OTHER INFORMATION: Gly is modified with acetyl
<220> FEATURE:
<221> NAME/KEY: MOD_RES
<222> LOCATION: 13
<223> OTHER INFORMATION: Lys is modified with 6-FAM
<220> FEATURE:
<221> NAME/KEY: MOD_RES
<222> LOCATION: 16
<223> OTHER INFORMATION: Arg is modified with NH2

<400> SEQUENCE: 1

Gly Gln Val Gly Arg Gln Leu Ala Ile Ile Gly Asp Lys Ile Asn Arg
1               5                   10                  15

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gatggacggg tccggaga                                                 18

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ctcagcccat cttcttccag                                               20

<210> SEQ ID NO 4
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tggttatggg atgggtgagg                                              20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5 ctgcttttc tcgcccttcc                                               20

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tccgaggtgc tccagttgga ggc                                          23

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gcccggcctg ggtctttcgc                                              20

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 8 cttcaattt caaatcaaac tgatc                                         25

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 9
tgaatgcttt gatttcctca cgttt                                        25

<210> SEQ ID NO 10
<211> LENGTH: 25
<212> TYPE: DNA
```

```
<213> ORGANISM: Artificial Sequence
<220> FEATURE:
<223> OTHER INFORMATION: Description of Artificial Sequence: Synthetic
      probe

<400> SEQUENCE: 10
ttgcctgaac atcttggaca ttttt                                         25
```